US 6,642,392 B1

(12) United States Patent
Basarab et al.

(10) Patent No.: US 6,642,392 B1
(45) Date of Patent: *Nov. 4, 2003

(54) FUNGICIDAL CARBOXAMIDES

(75) Inventors: Gregory Steven Basarab, Hockessin, DE (US); Douglas Brian Jordan, Wilmington, DE (US); Thomas Arend Lessen, Lincoln University, PA (US); Stephen L. Hansen, Frazer, PA (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/798,421

(22) Filed: Mar. 2, 2001

Related U.S. Application Data

(62) Division of application No. 09/355,785, filed as application No. PCT/US98/01668 on Jan. 27, 1998, now Pat. No. 6,251,947.
(60) Provisional application No. 60/037,207, filed on Feb. 4, 1997.

(51) Int. Cl.[7] ................ C07D 207/30; A01N 43/36
(52) U.S. Cl. ................ 548/561; 548/542; 514/424; 514/427
(58) Field of Search ................ 548/542, 561; 514/424, 427

(56) References Cited

U.S. PATENT DOCUMENTS

| | | | | |
|---|---|---|---|---|
| 4,946,867 A | * | 8/1990 | Manabe et al. | 514/521 |
| 5,034,408 A | * | 7/1991 | Wollweber et al. | 514/423 |
| 6,251,947 B1 | * | 6/2001 | Basarab et al. | 514/624 |

* cited by examiner

Primary Examiner—Shailendra Kumar
(74) Attorney, Agent, or Firm—Gilbreth & Associates, P.C.; J. M. (Mark) Gilbreth; Mary A. Gilbreth

(57) ABSTRACT

Compounds of Formula I are disclosed which are useful as fungicides

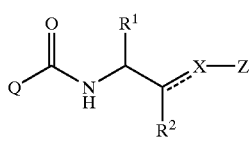

wherein

Q is

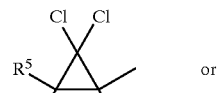

Q-1 or

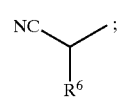

Q-2

Z is

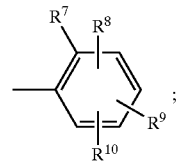

Z-1

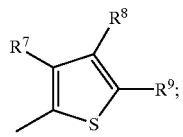

Z-2

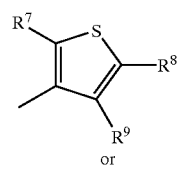

Z-3 or

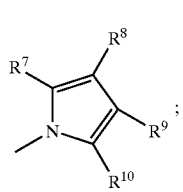

Z-4

X is —O—, —CH($R^{11}$)— or =C($R^{11}$)—;
$R^1$ is H or $C_1$–$C_2$ alkyl;
$R^2$ is H; $C_1$–$C_6$ alkyl; $C_3$–$C_6$ cycloalkyl; or phenyl optionally substituted with halogen, cyano, $C_1$–$C_2$ alkyl or $C_1$–$C_2$ alkoxy;
and $R^3$–$R^{11}$ are as defined in the disclosure.

Also disclosed are compositions containing the compounds of Formula I and a method for controlling plant diseases caused by fungal plant pathogens which involves applying an effective amount of a compound of Formula I.

10 Claims, No Drawings

FUNGICIDAL CARBOXAMIDES

This application is a divisional of Ser. No. 09/355,785, filed Aug. 4, 1999, now U.S. Pat. No. 6,251,947, which is a 371 of PCT/US98/01668, filed Jan. 27, 1998, and also claims priority from Ser. No. 60/037,207, filed Feb. 4, 1997.

BACKGROUND OF THE INVENTION

This invention relates to certain N-(arylpropyl), N-(aryloxyethyl), and N-(arylallyl)-carboxamides, their agriculturally suitable salts and compositions, and methods of their use as fungicides.

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different modes of action.

U.S. Pat. No. 4,710,518 discloses compounds of Formula i and compositions thereof as fungicides:

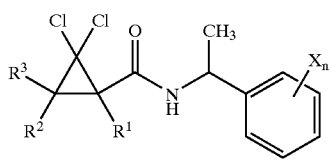

wherein

X is halogen;

n is 1 or 2;

$R^1$ is hydrogen, halogen or lower alkyl;

$R^2$ is lower alkyl, halogen-substituted lower alkyl or hydrogen; and $R^3$ is hydrogen or lower alkyl.

U.S. Pat. No. 4,946,867 discloses compounds of Formula ii, and compositions and method of use thereof, as fungicides:

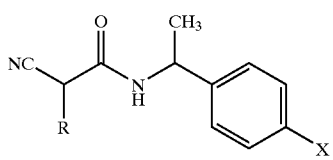

wherein

R is $C_2$–$C_6$ alkyl, $C_2$–$C_6$ alkenyl, $C_2$–$C_6$ alkynyl or $C_3$–$C_6$ cycloalkyl; and X is Cl, Br, $CF_3$ or lower fluoroalkoxy group.

SUMMARY OF THE INVENTION

This invention is directed to compounds of Formula I (including all geometric and stereoisomers), agricultural compositions containing them and their use as fungicides:

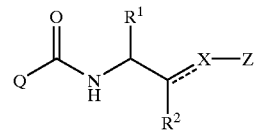

wherein

Q is

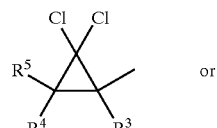 or

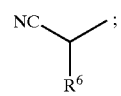

Z is

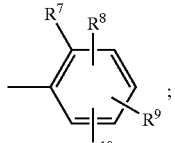

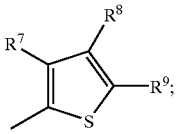

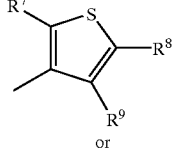 or

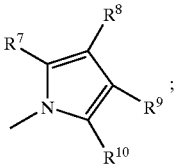

X is —O—, —CH($R^{11}$)— or =C($R^{11}$)—;

$R^1$ is H or $C_1$–$C_2$ alkyl;

$R^2$ is H; $C_1$–$C_6$ alkyl; $C_3$–$C_6$ cycloalkyl; or phenyl optionally substituted with halogen, cyano, $C_1$–$C_2$ alkyl or $C_1$–$C_2$ alkoxy;

$R^3$ is H, $C_1$–$C_3$ alkyl optionally substituted with halogen or CN;

$R^4$ is H or $C_1$–$C_2$ alkyl; or $R^3$ and $R^4$ can be taken together as —$CH_2CH_2CH_2$— or —$CH_2CH_2CH_2CH_2$—;

$R^5$ is H, $C_{1-C2}$ alkyl optionally substituted with halogen or CN;

$R^6$ is $C_2$–$C_8$ alkyl, $C_2$–$C_8$ alkenyl, $C_2$–$C_8$ alkynyl, $C_2$–$C_8$ alkynylalkenyl or $C_3$–$C_8$ cycloalkyl, each optionally substituted with halogen;

$R^7$ is H, CN, halogen, $C_1$–$C_2$ haloalkoxy or $C_1$–$C_2$ haloalkylthio; or $C_1$–$C_4$ alkyl $C_2$–$C_4$ alkenyl or $C_2$–$C_4$ alkynyl, each optionally, substituted with halogen or CN;

$R^8$, $R^9$ and $R^{10}$ are each independently H, halogen, $C_1$–$C_3$ alkyl, $C_1$–$C_3$ haloalkyl, or $Si(CH_3)_3$; and $R^{11}$ is H, $C_1$–$C_5$ alkyl, $C_2$–$C_5$ alkenyl or $C_2$–$C_5$ alkynyl.

DETAILS OF THE INVENTION

In the above recitations, the term "alkyl", used in compound words such as "haloalkyl" includes straight-chain or branched alkyl, such as, methyl, ethyl, n-propyl or i-propyl. The term "alkyl", used alone includes straight-chain or branched alkyl, such as, methyl, ethyl, n-propyl, i-propyl, or the different butyl, pentyl, hexyl, heptyl or octyl isomers. "Alkenyl" includes straight-chain or branched alkenes such as vinyl, 1-propenyl, 2-propenyl and the different butenyl, pentenyl, hexenyl, heptenyl and octenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl, hexynyl, heptynyl and octynyl isomers. "Alkynyl" can also include moieties comprised of multiple triple bonds such as 2,5-hexadiynyl. "Cycloalkyl" includes, for example, cyclopropyl, cyclobutyl, cyclopentyl and cyclohexyl. "Alkynylalkenyl" is a compound word and includes straight-chain or branched alkyne substituted on a straight-chain or branched alkene. Examples of "alkynylalkenyl" include $H_2C=CHC(CH_3)(C\equiv CH)$ and $HC\equiv CCH=CHC(CH_3)_2$.

In the above recitations, the term "alkoxy", used in compound words such as "haloalkoxy" or "haloalkylthio" includes methyl and ethyl. Examples of "haloalkoxy" include $CF_3CH_2O$, $CF_3O$, $CHF_2CF_2O$, $HF_2CO$ and $CCl_3CCl_2O$. Examples of "haloalkyl" include $CF_3S$, $HF_2CS$, $CCl_3S$, $CHF_2CF_2S$ and $CF_3CH_2S$.

The term "halogen", either alone, when a group is "optionally substituted with halogen" or in compound words such as "haloalkyl", "haloalkoxy" or "haloalkylthio"; includes fluorine, chlorine, bromine or iodine. Further, when used in compound words such as "haloalkyl" or when a group is "optionally substituted with halogen", said alkyl or group may be partially or fully substituted with halogen atoms which may be the same or different. Examples of "haloalkyl" include $F_3C$, $ClCH_2$, $CF_3CH_2$ and $CF_3CCl_2$. Examples of an alkyl group "optionally substituted with halogen" include $CH(F)=CHC(CH_3)(CH_2F)$ and $CH_2=CHC(CH_3)(CH_2F)$.

The total number of carbon atoms in a substituent group is indicated by the "$C_i$–$C_j$" prefix where i and j are numbers from 1 to 6. For example, $C_1$–$C_3$ alkyl designates methyl through propyl. When a group contains a substituent which can be hydrogen, for example $R^1$ or $R^3$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula I. The compounds of the invention may be present as a mixture of stereoisomers, individual stereoisomers, or as an optically active form.

Of note are compounds where $R^7$ is other than H, especially when Z is Z-1. Also of note are compounds where $R^7$ is hydrogen and $R^8$ is other than hydrogen and when Z is Z-1 is attached to the carbon adjacent to the $R^7$ substituted carbon. Further of note are compounds where the carbon attached to $R^1$ has the (R) configuration.

Also of note are compounds wherein $R^1$ is H or $CH_3$; $R^2$ is H or $CH_3$; $R^6$ is $C_2$–$C_6$ alkyl, $C_2$–$C_6$ alkenyl, $C_2$–$C_6$ alkynyl or $C_3$–$C_6$ cycloalkyl each optionally substituted with halogen; and $R^7$ is H, CN, halogen, $C_1$–$C_4$ haloalkyl, $C_1$–$C_4$ alkyl, $C_2$–$C_4$ alkenyl or $C_2$–$C_4$ alkynyl each optionally substituted with halogen or CN.

Compounds of the invention include compounds of Formula Ia, Ib and Ic.

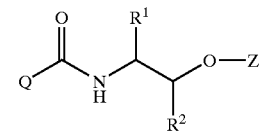

Ia

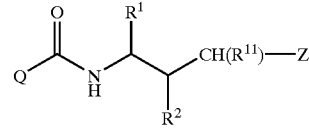

Ib

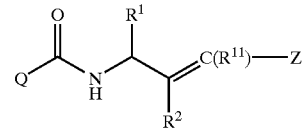

Ic

Preferred compounds for reasons of better activity and/or ease of synthesis are:

Preferred 1. Compounds of Formula I above and agriculturally suitable salts thereof, wherein:
Q is Q-1;
$R^1$ is $CH_3$;
$R^2$ is H;
$R^3$ is $CH_2CH_3$; and
$R^4$ is $CH_3$.

Preferred 2. Compounds of Preferred 1 wherein:
Z is Z-1 or Z-4;
$R^7$ is H, halogen, CN, $C_1$–$C_4$ alkyl or $C_2$–$C_4$ alkenyl;
$R^8$ is H or F and is in the para position with respect to X when Z is Z-1; and
$R^9$ is in the para position with respect to $R^7$ when Z is Z-1.

Preferred 3. Compounds of Preferred 1 wherein:
Z is Z-2 or Z-3; and
$R^7$ is H, halogen; CN, $C_1$–$C_3$ alkyl or $C_2$–$C_4$ alkenyl.

Preferred 4. Compounds of Formula I above and agriculturally suitable salts thereof, wherein:
Q is Q-2;
$R^1$ is $CH_3$;
$R^2$ is H or phenyl optionally substituted with halogen, cyano, $C_1$–$C_2$ alkyl or $C_1$–$C_2$ alkoxy; and
$R^6$ is $C_2$–$C_6$ alkyl or $C_2$–$C_6$ alkenyl each optionally substituted with halogen.

Preferred 5. Compounds of Preferred 4 wherein:
Z is Z-1 or Z-4;
$R^7$ is H, halogen, $C_1$–$C_3$ alkyl, $C_2$–$C_4$ alkenyl or $C_2$–$C_4$ alkynyl;

$R^8$ is H or F and is in the para position with respect to X when Z is Z-1; and $R^9$ is in the para position with respect to $R^7$ when Z is Z-1.

Preferred 6. Compounds of Preferred 4 wherein:

Z is Z-2 or Z-3; and $R^7$ is H, halogen, $C_1$–$C_4$ alkyl, $C_2$–$C_4$ alkenyl or $C_2$–$C_4$ alkynyl.

This invention also relates to fungicidal compositions comprising fungicidally effective amounts of the compounds of the invention and at least one of a surfactant, a solid diluent or a liquid diluent. The preferred compositions of the present invention are those which comprise the above preferred compounds.

This invention also relates to a method for controlling plant diseases caused by fungal plant pathogens comprising applying to the plant or portion thereof, or to the plant seed or seedling, a fungicidally effective amount of the compounds of the invention (e.g., as a composition described herein). The preferred methods of use are those involving the above preferred compounds.

DETAILS OF THE SYNTHESIS

The compounds of Formula I can be prepared by one or more of the following methods and variations as described in Schemes 1. The definitions of Q, $R^1$, $R^2$, $R^3$, $R^4$, $R^5$, $R^6$, $R^7$, $R^8$.

$R^9$, $R^{10}$, $R^{11}$, X and Z in the compounds of Formulae I–XXXIII below are as defined above in the Summary of the Invention.

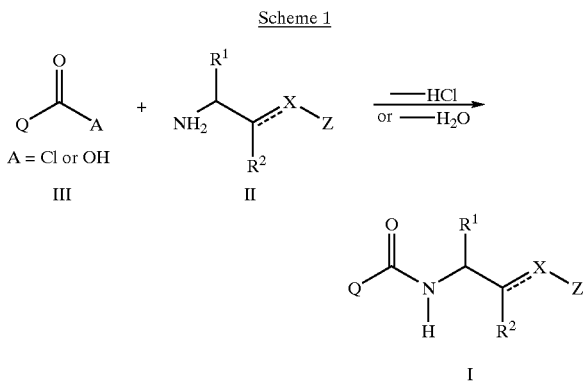

Scheme 1

When A is OH, the amine of Formula II is condensed with the carboxylic acid of Formula III in the presence of a dehydrating reagent, such as N,N'-dicyclohexylcarbodiimide (DCC) or carbonyl diimidazole (CDI), in the presence of an inert solvent. The process can be carried out over a wide temperature range in a wide variety of solvents. Generally, the condensation is carried out at a temperature between 20° C. and the boiling point of the reaction mixture, preferably about 100° C., for 0.1 to 72 h. Examples of suitable solvents include methylene chloride, toluene, diethyl ether, tetrahydrofuran, acetone and acetonitrile.

When A is chlorine, the amine of Formula II is condensed with the carboxylic acid chloride of Formula III in the presence of an acid acceptor such as triethylamine, in an inert solvent. Suitable reaction temperatures, times, solvents, and pressures are the same as described for the condensation wherein A is OH.

The amines of Formula II are known or can be prepared by a variety of methods. Formula II amines can be prepared from carbamates IV wherein $R^{12}$ is typically t-butyl or benzyl or from V in which Y is typically phenyl (forming a phthalimide ring) or bis-t-butoxycarbonyl (forming a bis-t-butoxycarbonyl protecting group). The removal of the carbamate and phthalimide protecting groups of IV and V to form II can be effected by methods set out in the literature such as those referenced in Greene, T. W. *Protective Groups in Organic Synthesis*; John Wiley & Sons, New York, N.Y., (1991), Chapter 7.

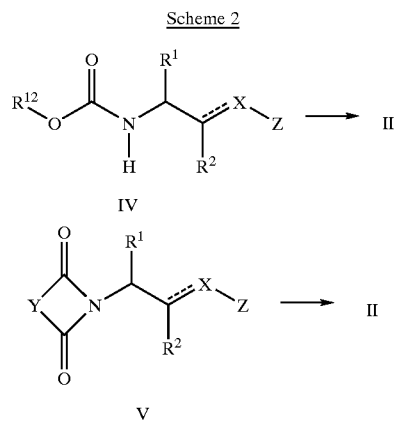

Scheme 2

The compounds of Formulas IVa and Va in which X is carbon with a double bond attachment are subsets of Formula IV and V compounds and can be prepared by treatment of protected amines of Formulas VIa and VIb, respectively, with aromatic bromides or iodides (for the cases in which Z is phenyl or thiophene) of Formula VII and 1–10 mole % of an appropriate Pd (II) catalyst. Appropriate catalysts include $PdCl_2$ and $Pd(OAc)_2$ complexed with a 2–4 fold excess of a phosphine ligand such as triphenylphosphine. The reactions are performed between 0° C. and 100° C. with a 1–3 molar equivalents of a base such as $K_2CO_3$ or triethylamine. Oftentimes 10–50 mole % of an ammonium phase transfer catalyst is used in the reaction mixture. Typical solvents include acetonitrile or dimethylformamide.

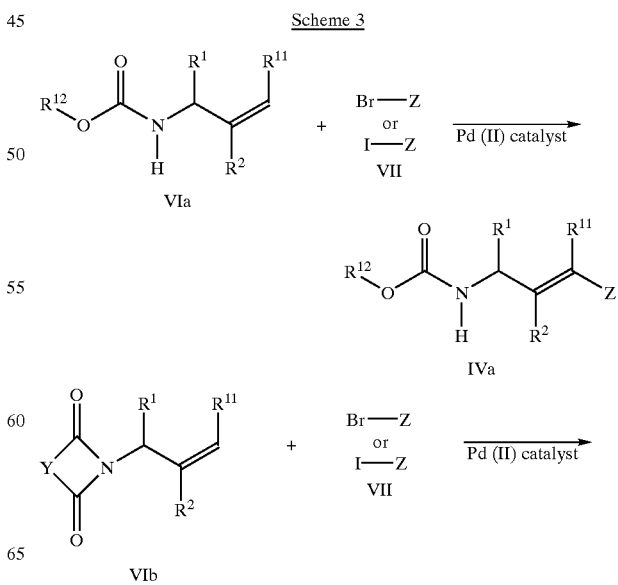

Scheme 3

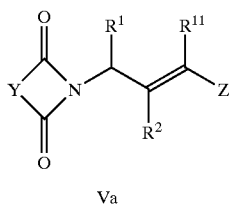

Va

Formula VI compounds are made from the corresponding unprotected amines by methods set out in the literature such as those referenced in Greene, T. W., *Protective Groups in Organic Synthesis*; John Wiley & Sons, New York, N.Y., (1991), Chapter 7. Alternatively, they may be prepared by displacement of a leaving group LG from compounds of Formula VIII with carbamates or diimides of Formula IXa or IXb in the presence of a base such as alkoxide salts as potassium t-butoxide, hydride salts as sodium hydride, or amine bases as diisopropyl ethylamine. Typical leaving groups LG includes chloride, bromide, iodide, (methylsulfonyl)oxy or [(4-methylphenyl)sulfonyl]oxy.

Scheme 4

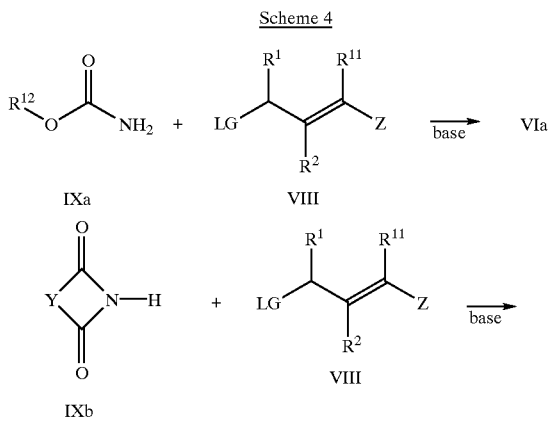

Formula VII, VIII and IX compounds are commercially available or are synthesized by procedures set out in the literature.

Alternatively, compounds of Formula IVa (for the cases in which Z is phenyl or thiophene) can be made from compounds of Formula XXXV by treatment with a phosphine such as triphenylphosphine in the presence of aromatic aldehydes and ketones of Formula XXXVI. The reactions are run in ethereal solvents such as glyme or tetrahydrofuran, hydrocarbon solvents such as toluene or protic solvents such as isopropyl alcohol or ethanol at temperatures ranging between 20° C. and 150° C. Formula XXXV and XXXVI are either commercially available or easily synthesized by methods set out in the literature.

Scheme 5

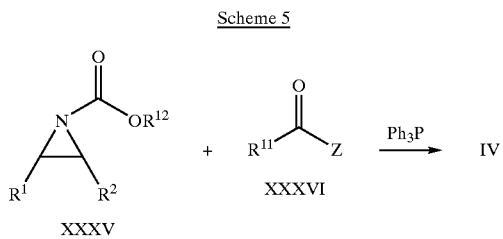

Compounds of Formulas IVb and Vb are a subset of Formula IV and Formula V compounds in which X is carbon with a single bond attachment and can be prepared from compounds of Formulas IVa and Va, respectively, by hydrogenation over an appropriate transition metal catalyst such as palladium, platinum or rhodium. Typically the catalyst is deposited over an inert support such as carbon, alumina or calcium carbonate. The hydrogenations are carried out in protic solvents such as ethanol or non-protic solvents such as tetrahydrofuran or ethyl acetate. Pressures of 1–10 torr of hydrogen are required. The hydrogenations are run at 25° C. but may be run at temperatures up to 100° C.

Scheme 6

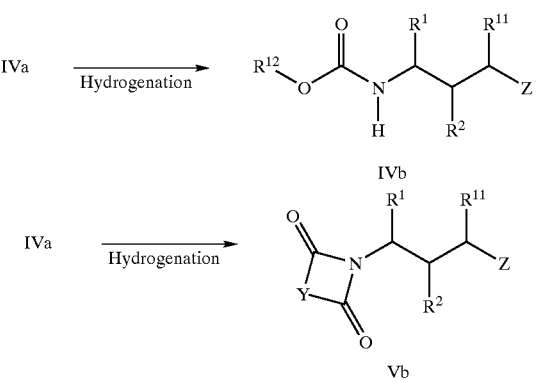

Alternatively, compounds of Formula IIb in which Z is phenyl or thiophene and X is carbon with a single bond attachment can be prepared from compounds of Formula X by reductive amination with an excess of an ammonium halide or acetate salt in the presence of a 1–10 equivalents of hydride reducing reagent such as sodium or tetrabutyl cyanoborohydride or sodium triacetoxyborohydride. The reaction can be run in protic solvents such as methanol or in aprotic solvents such as tetrahydrofuran or dichloromethane. An acid catalyst such as HCl or p-toluenesulfonic acid is often added portionwise so as to maintain a pH of 3–5 as determined by a pH meter or an indicator dye such as bromocresol green or methyl orange. Typical temperatures for the reductive aminations range from –5° C. to 60° C.

Scheme 7

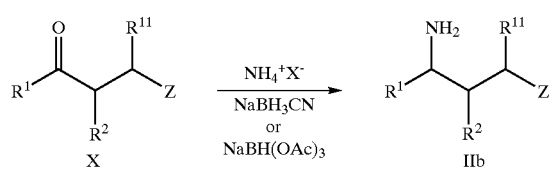

Compounds of Formula X can be prepared from compounds of Formula XI in which Z is phenyl or thiophene by hydrogenation under the conditions described for the conversion of compounds IVa and Va to compounds IVb and Vb. Compounds of Formula XI can be prepared by olefination of compounds of Formula XII in which Z is phenyl or thiophene with an appropriate triphenylphosphonium ylide or an appropriate phophonate anion. The olefination reactions are typically carried out in ethereal solvents such as tetrahydrofuran or dimethoxyethane or in polar aprotic solvents such as dimethylsulfoxide or dimethylformamide at temperatures ranging from 0 to the 100° C. The ylides and phosphonate anions are generated with alkoxide or hydride bases respectively and by methods set out otherwise in the literature (see March J. *Advanced Organic Chemistry*; John Wiley & Sons: New York, (1992); 4th Ed., pp 956–963).

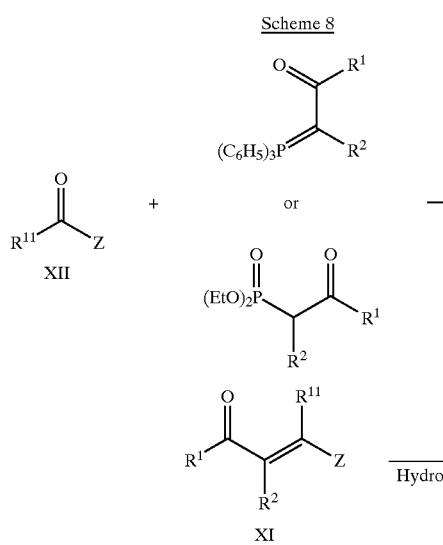

Scheme 8

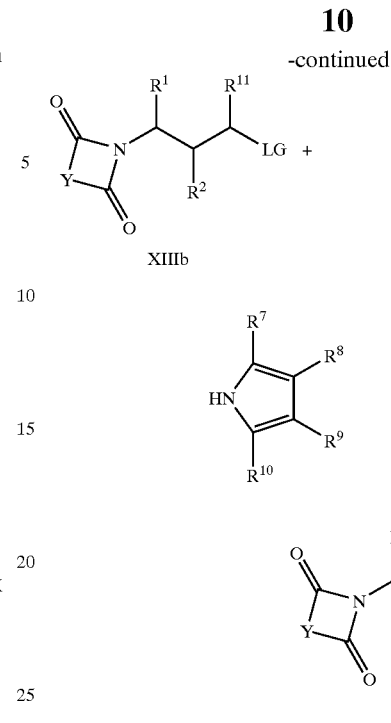

Compounds of Formula IVb or Vb in which Z is pyrrolyl can be prepared by displacement of the leaving group LG of compounds of Formulas XIIIa or XIIIb in the presence of an acid acceptor which can be a tertiary amine such as triethylamine, an alkoxide such as potassium t-butoxide or a carbonate such as potassium carbonate. The leaving group LG is as described for Formula VIII compounds. The displacements can be carried out in polar aprotic solvents such as dimethylformamnide or dimethylsulfoxide, ethereal solvents such as tetrahydrofuran or dioxane, or in protic solvents such as ethanol. Reaction temperatures can vary from 20° C. to 150° C.

Compounds of Formula XIII can be prepared from the compounds of Formulas XIVa or XIVb by standard methods for the conversion of alcohols to halides (March, J. *Advanced Organic Chemistry*; John Wiley & Sons: New York, (1992); 4th Ed., pp 431–433) and for the conversion of alcohols to sulfonates (March, J. *Advanced Organic Chemistry*; John Wiley & Sons: New York, (1992); 4th Ed., pp 498–499). Compounds XIV can, in turn, be prepared from the aminoalcohol by methods set out in the literature such as those referenced in Greene, T. W. *Protective Groups in Organic Synthesis*; John Wiley & Sons, New York, N.Y., (1991), Chapter 7.

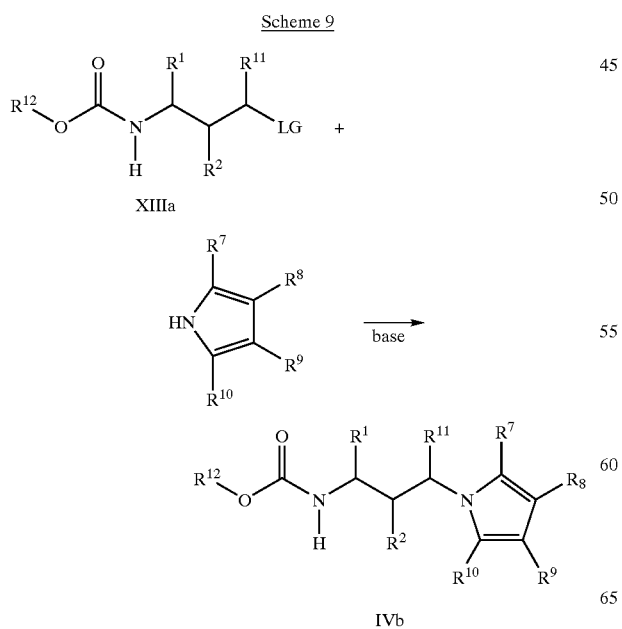

Scheme 9

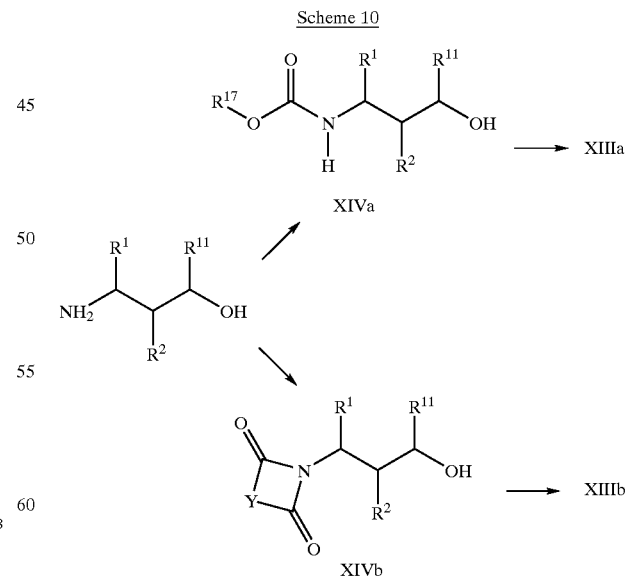

Scheme 10

Compounds of Formula IVc and Vc are a subset of compounds of Formula IV in which X is O and can be prepared from compounds of Formula XVa and XVb, respectively, by displacement of the leaving group LG with compounds of Formula XVI under conditions as described for the conversion of XIII to IVb and Vb. The leaving group LG is as described for Formula VIII compounds. Formula XVa and XVb compounds can be prepared from the corresponding alcohols XVIIa and XVIIb as described for Formula XIII compounds. Alternatively, IVc and Vc can be prepared directly from XVIIa and XVIIb, respectively, and XVI in the presence of 1–2 equivalents of triphenylphosphine and 1–2 equivalents of diethylazodicarboxylate. The reaction is generally run in an inert solvent such as methylene chloride or tetrahydrofuran at a temperature range of 0° C. to 100° C. Compounds of Formula XVI are generally commercially available or can be prepared by methods set out in the literature. For a review of literature methods for when Z is pyrrolyl, see Achesson, R. M. *Adv. Heterocycl. Chem.* (1990), 51, 115–119. Compounds of Formula XVII are prepared from the corresponding aminoalcohol as described for the preparation of compounds of Formula XIV.

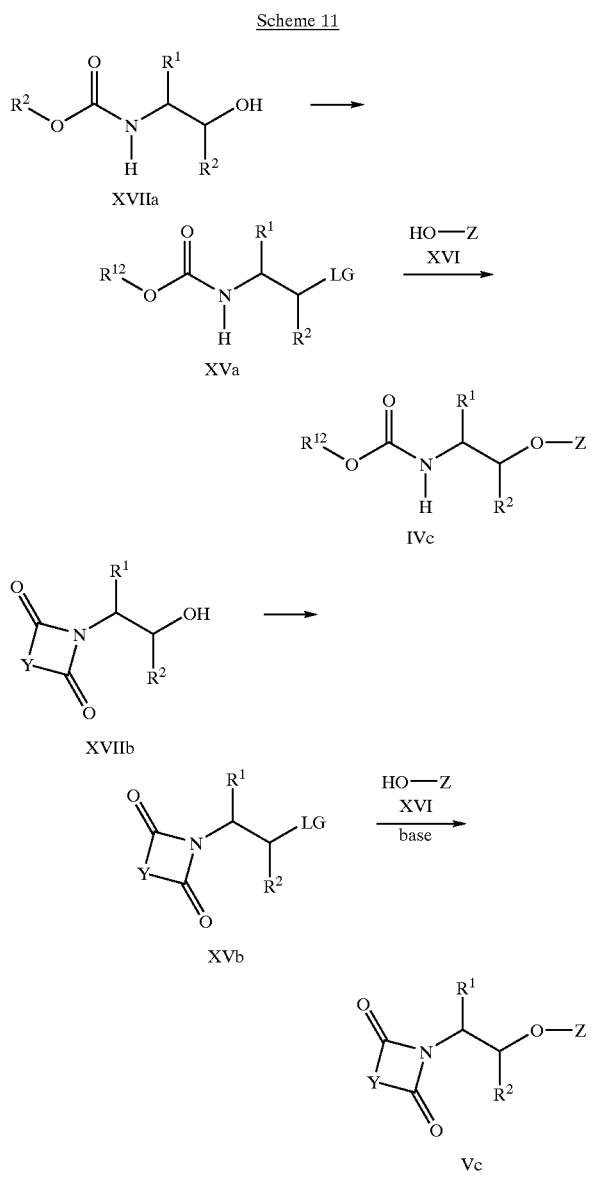

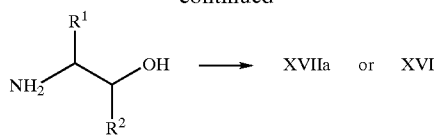

Alternatively, compounds of Formula IVc in which Z is phenyl or thiophene can be prepared by reaction of compounds XVIIa with base and an activated aryl fluoride of Formula XVIII. Appropriate bases include hydride salts such as sodium hydride, amine salts such as lithium diisopropylamine and alkoxide salts such as potassium t-butoxide. Solvents for the reaction can include ethereal solvents such as tetrahydrofuran or polar aprotic solvents such as dimethylformamide. Reaction temperatures can vary from −20° C. to 150° C. The reaction is facilitated for the cases in XVIII wherein at least one of $R^7$, $R^8$, $R^9$, or $R^{10}$ is an electron withdrawing group such as CN or halogen.

Scheme 12

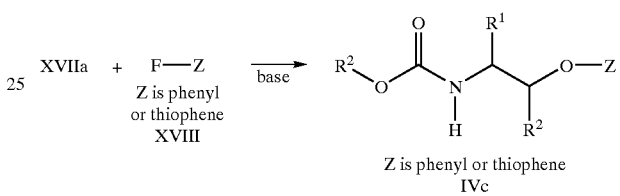

Compounds of Formula IIIa, a subset of Formula II compounds wherein A is OH, can be prepared from the corresponding esters of Formula XIX wherein $R^{13}$ is $C_1$–$C_5$ alkyl or optionally substituted benzyl via standard methods for ester hydrolysis (see Greene, T. W. *Protective Groups in Organic Synthesis*; John Wiley & Sons, New York, N.Y., (1991), pp 227–260).

Scheme 13

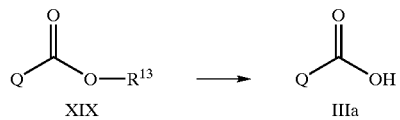

Compounds of Formula XIXa, a subset of Formula XIX compounds, can be prepared from compounds of Formula XX by treatment with excess dichlorocarbene. Dichlorocarbene can be generated in chloroform solvent and reacted with XX in a biphasic mixture with 5–20 equivalents of sodium or potassium hydroxide facilitated by 1–20 mole % of a tetraalkyl ammonium halide or a crown ether phase transfer catalyst. The reaction is run at temperatures ranging from 0° C. to 60° C. The conversion of XX to XIXa can also be effected by treatment with 1–5 equivalents of the alkali metal salts of trichloroacetic acid in ethereal solvents such as diglyme or dioxane or aromatic hydrocarbon solvents such as benzene or toluene or under neat conditions. The reaction temperatures can vary from 60° C. to 150° C. Addition of 1–20 mole % of a phase transfer catalyst such as 18-crown-6 or tetrabutyl ammonium chloride can enhance the reaction. Alternatively, the conversion of XX to XIX can be effected by treatment with 1–5 equivalents of methyl or ethyl esters of trichloroacetic acid in the presence of 1–5 equivalents of sodium methoxide or sodium ethoxide. Appropriate solvents include hydrocarbons such as pentane or cyclohexane, ethers such as tetrahydrofuran or dimethoxyethane or aromatic hydrocarbons such as benzene or toluene. The temperature of the reaction can vary from −20° C. to 120° C.

Scheme 14

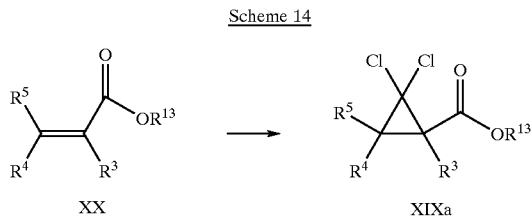

Compounds of Formula XX are prepared via condensation of compounds of Formula XXI and XXII. The conditions for such condensations are described in the references contained in March, J. *Advanced Organic Chemistry*; John Wiley Sons: New York, (1992,; 4th Ed., pp 944–945.

Scheme 15

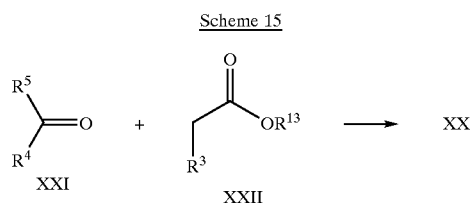

Alternatively, compounds of Formula IIIb, a subset of Formula IIIa compounds, can be prepared by oxidation of compounds of Formula XXIII via a variety of methods set out in the literature for the oxidation of alcohols to acids (see Larock, R. C. *Comprehensive Organic Transformations*; VCH Publishers: New York, (1989), pp 834–837). The dichlorocyclopropane of XXIII can be introduced by reaction of compounds of Formula XXIV via conditions described for the conversion of XX to XIXa.

Scheme 16

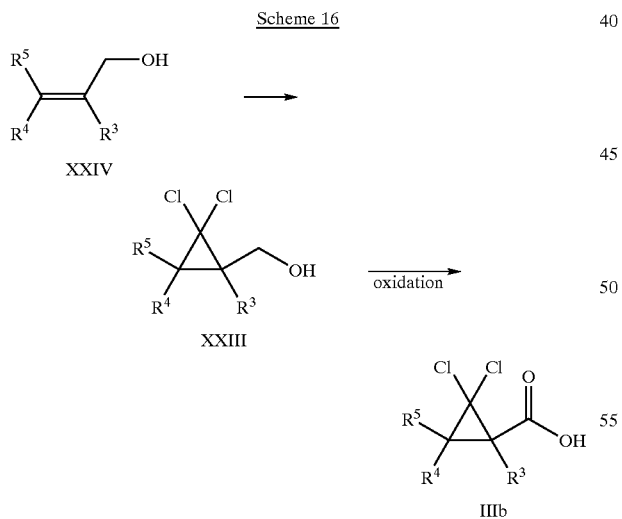

The conversion of XXIV to XXIII can sometimes be more efficiently mediated by the use of protecting group chemistry. Thus the alcohol of XXIV can be converted to an ether XXV in which PG can be an alkyl, benzyl or silyl protecting group. Conversion to XXIII is effected by subsequent cyclopropanation to XXVI via conditions described for the conversion of XIX to III followed by removal of the protecting group. Appropriate protecting groups PG and the condition for their introduction and removal are described in Greene, T. W. *Protective Groups in Organic Synthesis*; John Wiley & Sons, New York, N.Y., (1991), pp 10–86.

Scheme 17

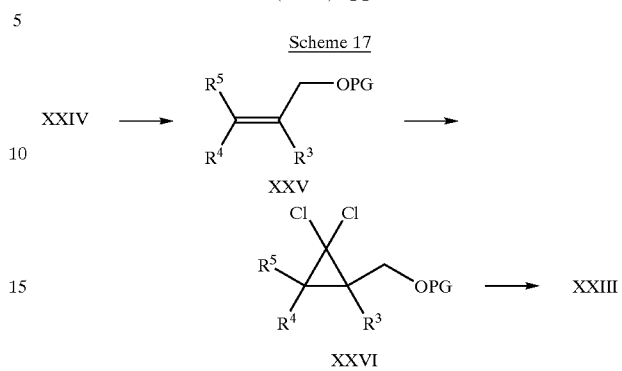

Compounds of Formula XXIV can be prepared from compounds of Formula XXVII by addition of 2–5 equivalents of Grignard reagents XXVIII and quenching via the dropwise addition of an excess of either a protic solvent such as water, methanol or acetic acid optionally containing a dissolved proton donor such as ammonium chloride or hydrogen chloride or a reagent of Formula XXIX in which LG is a leaving group as described for Formula VIII compounds. The reaction is performed in ethereal solvents such as diethyl ether or tetrahydrofuran at temperatures ranging from 0° C. to 60° C. with quenching carried out at temperatures ranging from −20° C. to 30° C.

Scheme 18

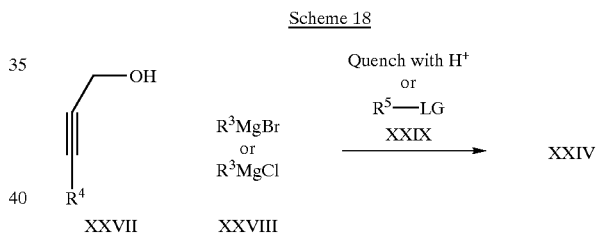

Alternatively, compounds of Formula XXIV can be prepared from compounds of Formula XXX by treatment with a 2–5 equivalents of a Grignard or zinc organometallic reagent of Formula XXXI (M is a magnesium halide or a zinc halide) in the presence of 1–10% of a transition metal catalyst such as $((C_6H_5)_3P)_2NiCl_2$ or $((C_6H_5)_3P)_4Pd$. The reaction is typically run in an ethereal solvent such as ethyl ether or tetrahydrofuran or a polar aprotic solvent such as dimethylformamide at temperatures ranging from −20° C. to 60° C.

Scheme 19

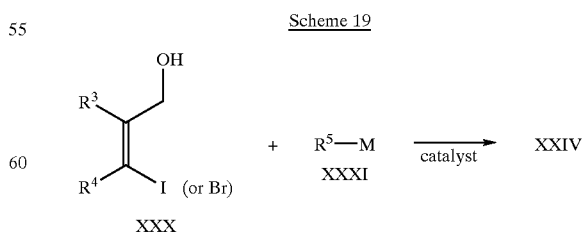

Compounds of Formula XXX can be prepared as described for the preparation of compounds of Formula XXIV with the modification that the reaction mixture is quenched with an excess of either I$_2$ or Br$_2$ added dropwise in the chosen reaction solvent.

Scheme 20

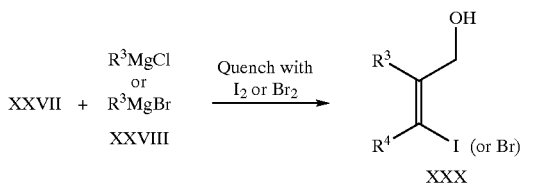

Compounds of Formula XIXb, as subset of Formula XIX compounds, are well known in the literature (see, for example, Alexander, E. R.; McCollum, J. D. and Pour, D. E. *J. Org. Chem.* (1950), 72, 4791–4972; Stevens, R. V.; Christenson, C. G.; Edmonson, W. L.; Kaplan, M.; Reid. E. B.; Wentlant, M. P. *J. Am. Chest. Soc.* (1971), 93, 6624–6637; and Anonymous, USA Res. Discl. (1985), 55, 249) and can be prepared by addition of a 1–2 equivalents of an alkyl magnesium, copper, zinc or lithium reagent of Formula XXXII in which R$^{16}$ is C$_1$–C$_4$ alkyl, C$_2$–C$_4$ alkenyl or C$_2$–C$_4$ alkynyl optionally substituted with CN to compounds of Formula XXXIII. R$^{14}$ and R$^{15}$ in XXXIII are independently H, C$_1$–C$_4$ alkyl, C$_2$–C$_4$ alkenyl, C$_2$–C$_4$ alkynyl or C$_3$–C$_6$ cycloalkyl each optionally substituted with halogen. The reaction is typically run in an ethereal solvent such as diethyl ether or tetrahydrofuran at temperatures ranging from −20° C. to 60° C. Optionally, a Cu (I) catalyst (1–10 mole %) such as copper (I) halide can be added to facilitate the reaction. Alternatively, XXXIII can be hydrogenated to XIXb under the conditions described for the conversion of IVa and Va to IVb and Vb. Compounds of Formula XXXIII are well known in the literature and are prepared by Knoevenagle condensation of cyanoacetic esters with aldehydes and ketones (see Jones, G. *Organic Reactions* John Wiley & Sons: New York, (1967); Vol. 15 pp 238–244).

Scheme 21

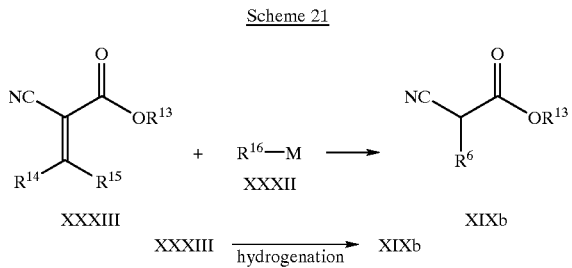

Compounds of Formula IIIc, a subset of Formula IIIa compounds in which Q is Q-2; R$^{14}$ and R$^{15}$ are as described previously; and R$^{17}$; R$^{18}$, R$^{19}$ are independently halogen, C$_1$–C$_2$ alkyl, C$_2$ alkenyl, C$_2$ alkynyl each optionally substituted with halogen can be prepared from compounds of Formula XXXIV. The rearrangement of Formula XXXIV compounds to Formula IIIc compounds can be carried out by procedures set out in the literature (see March, J. *Advanced Organic Chemistry*; John Wiley & Sons: New York, (1992); 4th Ed., pp 1136–1141). Typically XXXIV is treated with 1 equivalent of a lithium or potassium amide or alkoxide base such as lithium diisopropyl amine or potassium t-butoxide in an inert solvent such as tetrahydrofuran or toluene at temperatures ranging from −78° C. to 150° C. Additionally, the intermediacy of silyl ketene acetals can be involved for the conversion by heating XXXIV to reflux in a solvent such as hexamethyldisilazane or in an inert solvent such as benzene or toluene in the presence of 1–10 equivalents of hexamethyldisilazane. The product of the silyl ketene acetal mediated rearrangement is a silyl ester which can be converted to the acid by acid or base hydrolysis.

Scheme 22

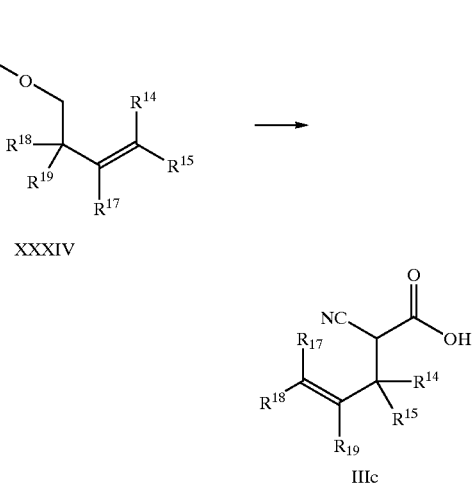

Compounds of Formula XXXIV can be prepared from compounds of Formula XXXV by standard conditions of esterification (see March, J. *Advanced Organic Chemistry*; John Wiley & Sons: New York, (1992); 4th Ed., pp 392–401). Formula XXXV compounds are generally commercially available or readily synthesized by methods set out in the literature.

Scheme 23

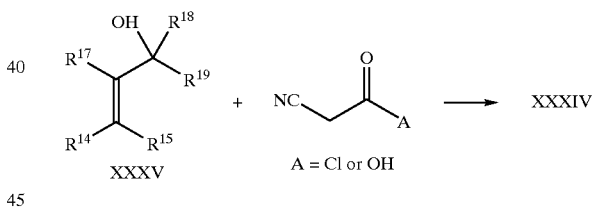

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane s=singlet, d=doublet, t=triplet, q=quartet, m=multiplet, dd=doublet of doublets, dt=doublet of triplets, br s=broad singlet.

EXAMPLE 1

Step A: Preparation of (cis)-2-ethyl-2-buten-1-ol

A solution of 800 mL of 3.0 M ethylmagesium bromide in ether was added dropwise to a solution of 40 ml (690 mmol) propargyl alcohol and 13.1 g (69 mmol) of copper iodide in 1 L ether cooled to 0° C. The mixture was allowed to warm to room temperature and stirred for 3 days. After cooling to 0° C., 295 g of iodine was added portionwise. The mixture was acidified with concentrated HCl and partitioned between ether and water. The ether was separated and washed with saturated aqueous $NaHSO_3$, water and brine. Drying ($MgSO_4$) and removal of solvent gave an oil which was distilled at 5 torr. The fraction boiling from 74–81° C. was the product, (trans)-2-(iodomethylene)-1-butanol, 49 g. This fraction was dissolved in 500 mL ether along with 7.8 g (12 mmol) of bis-triphenylphospine nickel(II) chloride and cooled to 0° C. A solution of 231 mL of 3.0 M methylmagnesium bromide in ether was added dropwise. The mixture was allowed to warm to room temperature and stirred overnight. Quenching first with IN HCl and then with concentrated HCl was followed by partitioning between ether and water. The ether was separated and washed with water, aqueous $NaHSO_3$, water and brine. Drying ($MgSO_4$) and removal of solvent gave an oil which was distilled at 0.5 torr. The fraction boiling from 83–96° C. was the product, (cis)-2-ethyl-2-buten-1-ol, 9.6 g.

Step B: Preparation of (cis)-2,2-dichloro-1-ethyl-3-methylcyclopropanecarboxylic acid A solution of 9.6 g (96 mmol) of (cis)-2-ethyl-2-buten-1-ol, and 0.44 g benzyltriethyl ammonium chloride in 200 mL of chloroform was cooled to 0° C. and a solution of 95.5 mL of 50% sodium hydroxide was added dropwise. After stirring 2 h, the mixture was diluted with water and extracted 3 times with ether. The ether was dried ($MgSO_4$) and stripped to give 19.4 g of an oil that was used further without purification. A solution of 16.7 g (91.7 mmol) of the oil was dissolved in 100 mL acetone and cooled to 0° C. A solution of 18.3 g (183 mmol) of $CrO_3$ in 125 mL of 25% $H_2SO_4$ was added dropwise. After stirring 5 min, a solution of saturated aqueous $NaHSO_3$ was added dropwise. The mixture was extracted with ether. The ether was washed with water and 3 times with 1N sodium hydroxide. The base extracts were acidified and extracted 3 times with ether. The ether was dried ($MgSO_4$) and stripped to give 9.32 g of product (cis)-2,2-dichloro-1-ethyl-3-methylcyclopropanecarboxylic acid as an oil that slowly solidified, mp 68–70° C., $^1$H NMR ($CDCl_3$): δ1.0 (t, 3H), 1.25 (d, 3H), 1.25 (m, 1H), 2.25 (m, 1H), 2.35 (q, 1H).

Step C: Preparation of (cis)-2,2-dichloro-1-ethyl-3-methyl-N-(3-phenylpropyl)cyclopropanecarboxamide A solution of 2.06 g (10.5 mmol) of (cis)-2,2-dichloro-1-ethyl-3-methyl 1-cyclopropane carboxylic acid in 10 mL thionyl chloride was heated at reflux for 30 min. Solvent was removed in vacuo. The residue was dissolved in 18 mL of dichloromethane. A portion (5 mL, 2.55 mmol) of this solution was added to a solution of 0.4 mL (2.8 mmol) 3-phenyl-1-propylamine and 0.33 mL (3.05 mmol) triethylamine in 25 mL dichloromethane. After stirring at room temperature overnight, the mixture was diluted with ethyl acetate and washed with water and brine. Drying ($MgSO_4$) and removal of solvent gave an oil which was chromatographed on silica gel (2:1 hexanes/ether) to give 260 mg of the title compound, mp 66–70° C., $^1$H NMR ($CDCl_3$) 1.05 (t, 3H), 1.3(d, 3H), 1.5 (m, 1H), 1.8–2.0 (m, 4H), 2.65 (t, 2H), 3.3–3.5 (m, 2H), 5.6 (br s, 1H), 7.2–7.4 (m, 5H).

EXAMPLE 2

Step A: Preparation of (trans)-2-ethyl-2-buten-1-ol

A solution 1070 mL (2.15 mol) of 2.0 M ethylmagnesium chloride in ether was added dropwise to a solution of 50 mL (720 mmol) of 2-butyn-1-ol and 14.9 g (78 mmol) of copper iodide in 1 L of 4:1 ether/tetrahydrofuran at 0° C. under an argon atmosphere. The solution was heated at reflux for 6 days. A solution of 65 mL of 25% by weight ethylmagnesium chloride in tetrahydrofuran was added. Heating at reflux was continued for another day. The reaction was quenched by dropwise addition of saturated aqueous $NH_4Cl$ and the mixture was partitioned between water and ether. The ether layer was separated and washed with water. Drying ($MgSO_4$) and removal of solvent gave 53.5 g of (trans)-2-ethyl-2-buten-1-ol as a mobile oil.

Step B: Preparation of (trans)-2,2-dichloro-1-ethyl-3-methylcyclopropanemethanol Imidazole (13.6 g, 200 mmol) was added portionwise to a solution of 8.0 g (80 mmol) of (trans)-2-ethyl-2-buten-1-ol and 14.5 g (96 mmol) of t-butyldimethylsilyl chloride in 20 mL of DMF and the mixture was stirred at room temperature overnight. The solution was poured into water and extracted with ethyl acetate. The ethyl acetate was washed 4 times with water and with brine. Drying ($MgSO_4$) and removal of solvent gave 17 g of (trans)-(1,1-dimethylethyl)[(2-ethyl-2-butenyl)oxy]dimethylsilane as a mobile oil. A solution of 10 g (46.6 mmol) of the oil and 0.21 g of benzyl triethylammonium chloride in 100 mL $CHCl_3$ was cooled to −5° C. A solution of 45 mL (85 mmol) of 50% sodium hydroxide was added dropwise and the mixture was warmed to room temperature and stirred for 3 h. The mixture was diluted with methylene chloride and washed with 3 times with water, 1N HCl and brine. Drying ($MgSO_4$) and removal of solvent gave 14 g of (trans)-[(2,2-dichloro-1-ethyl-3-methylcyclopropyl)methoxy](1,1-dimethylethyl) dimethylsilane as a viscous oil. This oil was dissolved in 200 mL of ethanolic 1% HCl which was heated at reflux for 2.5 h. Solvent was removed and the residue was diluted with methylene chloride and washed with water and brine. Drying ($MgSO_4$) and removal of solvent gave 8.95 g of (trans)-2,2-dichloro-1-ethyl-3-methylcyclopropanemethanol.

Step C: Preparation of (trans)-2,2-dichloro-1-ethyl-3-methylcyclopropanecarboxylic acid Sodium periodate (21 g, 98 mmol) was added portionwise to a solution of 8.91 g (4.92 mmol) of (trans)-2,2-dichloro-1-ethyl-3-methyl-cyclopropanemethanol and 0.22 g (1 mmol) of $RuCl_3.H_2O$ in 100 mL of 1:1 acetonitrile/carbon tetrachloride and 70 mL of water. After stirring 3 h, the mixture was diluted with methylene chloride and washed with water and brine, dried ($MgSO_4$) and stripped. The residue was dissolved in ether and washed 2 times with 1N sodium hydroxide and with water. The combined aqueous layers were acidified and extracted 2 times with ether. The ether was washed with water and dried ($MgSO_4$). Removal of solvent gave 6.1 g of (trans)-2,2-dichloro-1-ethyl-3-methylcyclopropanecarboxylic acid as an oil that slowly solidified, mp 61–63° C.

Step D: Preparation of (R)-2-[1-methyl-2-[(methylsulfonyl)oxy]ethyl]-1H-isoindole-1,3(2H)-dione Methanesulfonyl chloride (9.4 mL, 68 mmol) was added to a solution of 12.6 g (61.5 mmol) of (R)-2-(2-hydroxy-1-methylethyl)-1H-isoindole-1,3(2H)-dione (Becker, Y. *J. Org. Chem.* (1980), 45 (11), pp 2145–2151) and 5.23 mL (67.6 mmol) of methanesulfonyl chloride, and the mixture was stirred at room temperature overnight. Solvent was removed, and the residue was dissolved in ethyl acetate which was washed with water and brine. Drying (MgSO$_4$) and removal of solvent gave 17 g of a tan oil which slowly solidified. Recrystallization from n-butylchloride gave (R)-2-[1-methyl-2-[(methylsulfonyl)oxy]ethyl]-1H-isoindole-1,3(2H)-dione as a white solid, mp 75–77° C.

Step E: Preparation of 5-chloro-6-methyl-2-pyridinamine 1-oxide, hydrochloride

To a solution of 110 g (666 mmol) of 5-chloro-6-methyl-pyridineamine (Kress, T. J.; Moore, L. L.; Costantino, S. M. *J Org. Chem.* (1976) 41(1), pp 93–96) in 1 L of dichloromethane was added 164 g (666 mmol) of m-chloroperoxybenzoic acid. The mixture was stirred at room temperature overnight and 20 g more of m-chloroperoxybenzoic acid was added. The mixture was stirred 1 h and 50 mL of saturated aqueous NaHSO$_3$ were added. The solvent was removed and the residue was taken up in 1 L of 1N HCl. The insoluble solids were filtered and washed with 3N HCl. Solvent was removed from the aqueous filtrate to give a solid which was recrystallized from ethanol affording 56.9 g of 5-chloro-6-methyl-2-pyridinamine 1-oxide, hydrochloride as a white solid, mp>250° C.

Step F: Preparation of 4-chloro-1-hydroxy-5-methyl-1H-pyrrole-2-carbonitrile

A solution of 55.9 g (287 mmol) of 5-chloro-6-methyl-2-pyridinamine-1-oxide, hydrochloride in 1 L 10% aq HCl was cooled to 0° C. An aqueous solution of 25.5 g (365 mmol) of sodium nitrite was added dropwise. After stirring 15 min, an aqueous solution of 23.7 g (365 mmol) sodium azide was added dropwise. The mixture was stirred at room temperature overnight then extracted 3 times with methylene chloride. Drying (MgSO$_4$) and removal of solvent gave 35 g of an orange solid which was dissolved in chloroform and heated at reflux for 4 days. Removal of solvent gave product which was purified by chromatography on silica gel (CH$_2$Cl$_2$ followed by ether) to isolate 2 components: 4.8 g of a higher R$_f$ material identified as 4-chloro-5-methyl-1H-pyrrole-2-carbonitrile. $^1$H NMR (CDCl$_3$) δ2.3 (s, 3H), 6.7 (s, 1H), 8.9 (br s, 1H) and 17.8 g of 4-chloro-1-hydroxy-5-methyl-1H-pyrrole-2-carbonitrile, mp 91–101° C., $^1$H NMR (CDCl$_3$) δ2.25 (s, 3H), 6.5 (s, 1H).

Step G: Preparation of (R)-4-chloro-1-[2-(1,3-dihydro-1,3-dioxo-2H-isoindol-2-yl)propoxy]-5-methyl-1H-pyrrole-2-carbonitrile A solution of 3.0 g (10.6 mmol) of (R)-2-[1-methyl-2-[(methylsulfonyl)oxy]ethyl]-1H-isoindole-1,3(2H)-dione, 2.0 g (12.7 mmol) of N-chloro-1-hydroxy-5-methyl-1H-pyrrole-2-carbonitrile and 1.76 g (12.7 mmol) of K$_2$CO$_3$ in 60 mL acetonitrile was heated at reflux overnight. Solvent was removed and the residue was taken up in ethyl acetate which was washed with water and brine. Drying (MgSO$_4$) and removal of solvent gave an oil which was chromatographed on silica gel (35% ether in hexanes) to give 2.55 g of (R)-4-chloro-1-[2-(1,3-dihydro-1,3-dioxo-2H-isoindol-2-yl)propoxy]-5-methyl-1H-pyrrole-2-carbonitrile as a white solid, $^1$H NMR (CDCl$_3$) δ1.55 (d, 3H), 2.15 (s, 3H), 4.45 (m, 1H), 4.8 (m, 2H), 6.5 (s, 1H), 7.75 (m, 2H), 7.85 (m, 2H).

Step H: Preparation of (R)-1-(2-aminopropoxy)-4-chloro-5-methyl-1-1H-pyrrole-2-carbonitrile A solution of 0.6 g (1.75 mmol) of (R)-4-chloro-1-[2-(1,3-dihydro-1,3-dioxo-2H-isoindol-2-yl)propoxy]-5-methyl-1H-pyrrole-2-carbonitrile and 0.42 mL (8.7 mmol) of hydrazine was heated at reflux for 50 min and cooled to room temperature. Precipitated solids were filtered and rinsed with ether. Solvent from the filtrate was removed and the residue was taken up in ether. The insoluble solids were filtered and rinsed with ether. The filtrate was stripped to afford 0.43 g of (R)-1-(2-aminopropoxy)-4-chloro-5-methyl-1-1H-pyrrole-2-carbonitrile as an oil.

Step I: Preparation of [1R-[1α(R*),3α]]-2,2-dichloro-N-[2-[(3-chloro-5-cyano-2-methyl-1H-pyrrol-1-yl)oxy]-1-methylethyl]-1-ethyl-3-methylcyclopropanecarboxamide mixed 1:1 with [1S-[1α(S*),3β]]-2,2-dichoro-N-[2-[(3-chloro-5cyano-2-methyl-1H-pyrrol-1-yl)oxy]-1-methylethyl]-1-ethyl-3-methylcyclopropanecarboxamide In a separate flask, 0.34 g (1.75 mmol) of (trans)-2,2-dichloro-1-ethyl-3-methylcyclopropanecarboxylic acid in 15 mL thionyl chloride was heated at reflux for 30 min. The thionyl chloride was stripped and the residue was dried in vacuo. The residue was dissolved in 20 mL methylene chloride and a solution of 0.43 g of (R)-1-(2-aminopropoxy)-4-chloro-5-methyl-1H-pyrrole-2-carbonitrile and 0.25 mL (1.8 mmol) triethylamine was added dropwise. The mixture was stirred at room temperature overnight. Solvent was stripped and the residue was taken up in ethyl acetate which was washed with water and brine. Drying (MgSO$_4$) and removal of solvent gave an oil which was chromatographed (40% ether in hexanes) on silica gel to give the title compounds as a 1:1 mixture of diastereomers as an oil, $^1$H NMR (CDCl$_3$) δ1.0 (m, 3H), 1.2 (d, 3H), 1.4 (2d, 3H, 1:1 ratio), 1.5–1.65 (m, 1H), 2.0–2.2 (m, 1H), 2.2 (s, 3H), 2.2–2.3 (m, 1H), 4.2–4.4 (m, 2H), 4.4–4.6 (m, 1H), 6.05 and 6.15 (2d, 1H, 1:1 ratio), 6.55 (2s, 1H, 1:1 ratio).

EXAMPLE 3

Step A: Preparation of 1,1-dimethylethyl[2-(2-cyano-4-fluorophenoxy)-1-methylethyl]carbonate Sodium hydride (1.26 g of a 60% dispersion in oil, 31.5 mmol) was rinsed 3 times with hexanes and suspended in 30 mL DMF at 5° C. Added was 4.5 mL (49.6 mmol) of 2,5-difluorobenzonitrile followed by 5.0 g (28.6 mmol) of (2-hydroxy-1-methylethyl)-carbamic acid-1,1-dimethylethyl ester portionwise. The mixture was stirred at room temperature overnight before being quenched with saturated aqueous NH$_4$Cl. After partitioning between ether and water, the ether was separated and washed 2 times with water and with brine. Drying (MgSO$_4$) and removal of solvent gave a solid which was triturated with hexanes to give 6.3 g of 1,1-dimethylethyl[2-(2-cyano-4-fluorophenoxy)-1-methylethyl]carbamate as a white solid, mp 77–78° C.

Step B: Preparation of 2-(2-aminopropoxy)-5-fluorobenzonitrile

A solution of 1.0 mL trifluoroacetic acid and 1.2 g (4.08 mmol) of 1,1-dimethylethyl[2-(2-cyano-4-fluorophenoxy)-1-methylethyl]carbamate in 10 mL methylene chloride was stirred at ambient temperature for 3 days. Solvent was removed and the residue was taken up in aqueous Na$_2$CO$_3$ and ethyl acetate. The organic layer was separated and washed with water and brine. Drying (MgSO$_4$)and removal of solvent gave 650 mg of 2-(2-aminopropoxy)-5-fluorobenzonitrile as an oil.

Step C: Preparation of (trans)-2 2-dichloro-N-[2-(2-cyano-4-fluorophenoxy-1-methylethyl]-1-ethyl-3-methylcyclopropanecarboxamide In a separate flask, 750 mg (3.8 mmol) of (trans)-2,2-dichloro-1-ethyl-3-methylcyclopropanecarboxylic acid in 20 mL thionyl chloride was heated at reflux for 30 min. The thionyl chloride was stripped and the residue was dried in vacuo. The residue was then dissolved in 2 mL methylene chloride and a solution of 0.67 g (3.45 mmol) 2-(2-aminopropoxy)-5-fluorobenzonitrile and 0.55 mL (3.95 mmol) triethylamine was added dropwise. The mixture was stirred at room temperature overnight. Solvent was stripped and the residue was taken up in ethyl acetate which was washed with water and brine. Drying (MgSO$_4$) and removal of solvent gave an oil which was chromatographed (50% ether in hexanes) on silica gel to give the title compound as a 1:1 mixture of diastereomers, mp 119–123° C. $^1$H NMR (CDCl$_3$) δ0.9 and 0.95 (2t, 3H, 1:1 ratio), 1.2 (d, 3H), 1.45 (m, 3H), 1.5–1.6 (m, 1H), 2.0–2.1 (m, 1H), 2.2 (m, 1H), 4.0–4.2 (m, 2H), 4.45 (m, 1H), 6.95 (m, 1H), 7.3 (m, 2H).

EXAMPLE 4

Step A: Preparation of 2-[1-methyl-2-[(methylsulfonyl)oxy]propyl]-1H-isoindole-1,3(2H)-dione Methanesulfonyl chloride (9.7 mL, 56 mmol) was added to a solution of 10.5 g (48 mmol) of 2-(2-hydroxy-1-methylpropyl)-1H-isoindole-1,3(2H)-dione (JP 01242569 A2) and 8.1 mL (58 mmol) of triethylamine and the mixture was stirred at room temperature overnight. The mixture was diluted with ether and washed with water and brine. Drying (MgSO$_4$) and removal of solvent gave an oil which slowly solidified. Trituration with hexanes gave 11.8 g of 2-[1-methyl-2-[(methylsulfonyl)oxy]propyl]-1H-isoindole-1,3(2H)-dione as a white solid, mp 67–73° C.

Step B: Preparation of 4-chloro-1-[3-(1,3-dihydro-1,3-dioxo-2H-isoindol-2-yl)butyl]-5-methyl-1H-pyrrole-2-carbonitrile A solution of 4.23 g (14.2 mmol) of 2-[1-methyl-2-[(methylsulfonyl)oxy]propyl]-1H-isoindole-1,3(2H)-dione, 2.05 g (14.2 mmol) of 4-chloro-5-methyl-1H-pyrrole-2-carbonitrile and 2.35 g (14.2 mmol) of K$_2$CO$_3$ in 60 mL DMF was heated at 60° C. overnight. The mixture was diluted with ether and washed 4 times with water. Drying (MgSO$_4$) and removal of solvent gave an oil which was chromatographed on silica gel (15% ethyl acetate in hexanes) to give 3.2 g of 4-chloro-1-[3-(1,3-dihydro-1,3-dioxo-2H-isoindol-2-yl)butyl]-5-methyl-1H-pyrrole-2-carbonitrile as a solid, $^1$NMR (CDCl$_3$) δ1.5 (d, 3H), 2.2 (s, 3H and m, 1H), 2.7 (m, 1H), 3.9 (m, 1H), 4.05 (m, 1H), 4.4 (m, 1H), 6.6 (s, 1H), 7.85 (m, 2H), 7.9 (m, 2H).

Step C: Preparation of 1-(3-aminobutyl)-4-chloro-5-methyl-1H-pyrrole-2-carbonitrile A solution of 3.2 g (9.4 mmol) of 4-chloro-1-[3-(1,3-dihydro-1,3-dioxo-2H-isoindol-2-5 yl)butyl]-5-methyl-1H-pyrrole-2-carbonitrile and 4.8 mL (94 mmol) of hydrazine in ethanol was heated at reflux for 60 min and cooled to room temperature. Precipitated solids were filtered and rinsed with ethyl acetate and the filtrate was concentrated to afford 1-(3-aminobutyl)-4-chloro-5-methyl-1H-pyrrole-2-carbonitrile as an oil.

Step D: Preparation of 2-cyano-3 4,4-trimethylpentanoic acid

A solution of 10 g (50 mmol) of ethyl 2-cyano-3,4,4-trimethylpentanote (Clarke, N. C.; Runciman, P. J. I.; Utley, J. H. P.; Landquist, J. K. *J. Chem. Soc., Perkin Trans. 2* (1987) (4), pp 435–439) and 2.93 g (52 mmol) of potassium hydroxide in 50 mL ethanol was heated at reflux for 3 h and stirred at room temperature overnight. The mixture was diluted with water and extracted twice with ether. The aqueous layer was acidified with concentrated HCl and extracted twice with ether which was washed with brine, dried (MgSO$_4$) and concentrated to afford 9.6 g of 2-cyano-3,4,4-trimethylpentanoic acid as a mixture of diastereomers, mp 68–78° C.

Step E: Preparation of N-[3-(3-chloro-5-cyano-2-methyl-1H-pyrrol-1-yl-1-methylpropyl]-2-cyano-3,4,4-trimethylpentanamide A solution of 0.54 g (3.5 mmol) 2-cyano-3,4,4-trimethylpentanoic acid in 15 mL thionyl chloride was heated at reflux for 30 min. The thionyl chloride was stripped and the residue was dried in vacuo. The residue was then dissolved in 20 mL methylene chloride and a solution of 0.66 g (3.13 mmol) of 1-(3-aminobutyl)-4-chloro-5-methyl-1H-pyrrole-2-carbonitrile and 0.59 mL (4.2 mmol) triethylamine was added dropwise. The mixture was stirred at room temperature overnight. Solvent was stripped and the residue was taken up in ethyl acetate which was washed with water and brine. Drying (MgSO$_4$) and removal of solvent gave an oil which was chromatographed (40% ether in hexanes) on silica gel to give the title compound as a mixture of diastereomers, mp 111–118° C. $^1$H NMR (CDCl$_3$) δ1.0 (m, 3H), 1.2–1.3 (2m, 6H), 1.4 (d, 1H), 1.6 (m, 2H), 1.9 (m, 2H), 2.2 (m, 3H), 4.1 (2m, 2H), 5.7 (m, 1H), 6.65 (2s, 1H).

EXAMPLE 5

Step A: Preparation of bis(1,1-dimethylethyl)-1-propenylimidodicarbonate

A solution of commercially available di-tert-butyliminodicarboxylate (25.0 g, 0.115 mol) in 100 mL of tetrahydrofuran was added to hexanes rinsed sodium hydride (5.0 g of 60% oil suspension, 0.125 mol) and stirred for 3 h at 20° C. A solution of allyl bromide (12.0 mL, 0.139 mol) in 30 mL tetrahydrofuran was added dropwise and the mixture was stirred 20 h. The reaction was quenched dropwise with 10 mL water, evaporated to a paste, treated with 200 mL water and extracted twice with ethyl acetate. The organic layers were combined, washed with saturated solution of ammonium chloride then concentrated to give an oil. The oil was purified by flash silica chromatography using 5% ethyl acetate/hexanes solution as eluent to give 26.0 g (88%) of bis(1,1-dimethylethyl)-1-propenylimidodicarbonate as colorless crystals: mp 44–46° C.; $^1$H NMR (300 MHz, CDCl$_3$) δ1.50 (s, 18H), 4.18 (m, 2H), 5.14 (m, 2H), 6.85 (m, 1H).

Step B: Preparation of bis(1,1-dimethylethyl)-2-propenyl-3-(2-fluorophenyl)imidodicarboxylate A solution of bis(1,1-dimethylethyl)-2-propenylimidodicarbonate (7.00) g, 27 mmol) and o-fluoroiodobenzene (8.10 g, 36.5 mmol) in 40 mL) acetonitrile was treated with triphenylphosphine (2.2 g, 8.4 mmol), tetrabutylanmmonium chloride (5.30 g, 18.3 mmol), potassium carbonate (12.4 g, 89.7 mmol) and palladium acetate (0.640 g, 2.85 mmol). The reaction mixture was heated at 65° C. for 4 h then treated with more palladium acetate (0.320 g, 1.43 mmol). The reaction mixture was stirred an additional 20 h at 65° C. The solvent was evaporated and the residue was purified by flash chromatography using 5% ethyl acetate/hexanes solution as eluent to give 4.0 g (42%) of bis(1,1-dimethylethyl)-2-propenyl-3-(2-fluorophenyl)imidodicarboxylate as a light yellow oil: $^1$H NMR (CDCl$_3$) δ1.52 (s, 18H), 4.36 (d, 2H), 6.30 (dt, 1H), 6.70 (d, 1H), 7.10 (m, 2H), 7.20 (m, 1H), 7.40 (t, 1H).

Step C: Preparation of (trans)-3-(2-fluorophenyl)-2-propen-1-amine hydrochloride A solution of bis(1,1dimethylethyl)-2-propenyl-3-(2-fluorophenyl)imidodicarboxylate (4.0 g, 11 mmol) in 30 mL of methylene chloride and 15 mL of trifluoroacetic acid was stirred at 20° C. for 18 h. The reaction mixture was evaporated and the residue diluted in ethyl acetate and washed twice with 1 N sodium hydroxide solution. Organic layer was evaporated to give the crude amine. Free amine was precipitated with hydrogen chloride (1 N in diethyl ether) and filtered through a fritted funnel to give 2.42 g (91%) of (trans)-3-(2-fluorophenyl)-2-propen-1-amine hydrochloride as a white powder: mp 205–208° C.; $^1$H NMR (Me$_2$SO-d$_6$) δ3.66 (d, 2H), 6.40 (dt, 1H), 6.81 (d, 1H), 7.24 (m, 2H), 7.40 (m, 1H), 7.60 (m, 1H), 8.20 (br s, 3H).

Step D: Preparation of (trans)-2,2-dichloro-1-ethyl-N-[3-(2-fluorophenyl)-2-propenyl]-3-methylcyclopropanecarboxamide A solution of (trans)-2,2-dichloro-1-ethyl-3-methylcyclopropanecarboxylic acid (see above) (5.1 g, 25.9 mmol) and 40 mL of toluene was treated with thionyl chloride (5.0 mL, 69 mmol) and warmed at 65° C. for 3 h. The solvent was evaporated and the residue was diluted in 5% toluene/Hexanes and treated with activated carbon. The suspension was filtered and the filtrate was concentrated in vacuo to give 5.05 g (91%) of the (trans)-2,2-dichloro-1-ethyl-3-methylcyclopropanecarbonyl chloride as a clear oil. A solution of acid chloride (0.33 g, 1.53 mmol) in 10 mL methylene chloride was added dropwise to a solution of amine of (trans)-3-(2-fluorophenyl)-2-propen-1-amine hydrochloride (0.40 g, 2.1 mmol), triethyl amine (1.0 mL, 7.2 mmol) in 30 mL methylene chloride. The reaction mixture was stirred for 2 h then concentrated in vacuo. The residue was purified by flash chromatography using 10% ethyl acetate/hexanes as eluent to give 0.480 g (95%) of the title compound as white solid: mp 103–105° C., $^1$H NMR (CDCl$_3$) δ1.01 (t, 3H), 1.25 (m, 3H), 1.60 (m, 1H), 2.00 (m, 1H), 2.22 (m, 1H), 4.11 (m, 2H), 5.90 (br s, 1H), 6.30 (dt, 1H), 6.75 (d, 1H), 7.07 (m, 2H), 7.20 (m, 1H), 7.40 (t, 1H).

EXAMPLE 6

Step A: Preparation of 2-[2-(2-ethylphenoxy)-1-methylethyl]-1H-isoindole-1,3(2H)-dione A solution of 5.0 g (24.4 mmol) of 2-(2-hydroxy-1-methylethyl)-1H-isoindole-1,3(2H)-dione (Y. Becker, A. Eisenstadt, J. K. Stille, *J. Org. Chem.*, 1980, 45, 2145) and triphenylphosphine (7.00 g, 27.0 mmol) in 40 mL of dry tetrahydrofuran was stirred at 20° C. for 1 h. To the solution was added 2-ethylphenol (3.90 g, 32.0 mmol) and diethyl azodicarboxylate (5.0 mL, 32.0 mmol) and the solution was stirred an additional 40 h. The reaction mixture was concentrated in vacuo and the residue was diluted in diethyl ether and washed with water and brine. The organic layer was concentrated in vacuo and the crude product was purified by flash silica chromatography using 5% ethyl acetate/hexanes solution as eluent to give 3.0 g (40%) of 2-[2-(2-ethylphenoxy)-1-methylethyl]-1H-isoindole-1,3 (2H)-dione as a colorless oil: $^1$H NMR (CDCl$_3$) δ0.96 (t, 3H), 1.60 (d, 3H), 2.40 (m, 2H), 4.18 (dd, 1H), 4.48 (t, 1H), 4.84 (m, 1H), 6.80 (m, 1H), 6.90 (m, 1H), 7.10 (m, 2H), 7.70 (m, 2H), 7.84 (m, 2H).

Step B: Preparation of 1-(2-ethylphenoxy)propanamine hydrochloride

2-[2-(2-Ethylphenoxy)-1-methylethyl]-1H-isoindole-1,3 (2H)-dione (3.0 g, 9.7 mmol) was dissolved in 300 mL of absolute ethanol and treated with anhydrous hydrazine (3.0 mL, 96 mmol) at reflux for 2 h. Reaction mixture was cooled and filtered through a fritted funnel and then the filtrate was concentrated. The residue was diluted in ethyl acetate and filtered mixture through a fritted funnel. The organic layer was extracted twice with 1 N hydrogen chloride solution. Aqueous layer was treated with 1 N sodium hydroxide solution (until solution pH=8–10), and was then extracted with ethyl acetate. The final organic layer was concentrated in vacuo to give 1-methyl-2-(2-fluorophenoxy)ethylamine as an oil. Free amine was precipitated with hydrogen chloride (1 N in diethyl ether) and filtered via a fritted funnel to give 1.30 g (62%) of 1-(2-ethylphenoxy)propanamine hydrochloride as a white powder: mp 131–133° C.; $^1$H NMR (Me$_2$SO-d$_6$) δ1.18 (t, 3H), 1.40 (d, 3H), 2.75 (m, 1H), 3.62 (m, 1H), 4.10 (m, 2H), 6.95 (m, 2H), 7.20 (m, 2H), 8.25 (br s, 3H).

Step C: Preparation of 2-cyano-N-[2-(2-ethylphenoxy)-1-methylethyl]-3,3-dimethylbutanamide A solution of 2-cyano-3,3-dimethylbutanoyl chloride (E. Schaumann, H. Mrotzek; *J. Org. Chem.*, 1979, 35, 1965.) (0.364 g, 2.28 mmol) in 10 mL methylene chloride was added dropwise to a solution of 1-(2-ethylphenoxy) propanamine hydrochloride (0.56 g, 2.6 mmol), triethyl amine (1.0 mL, 7.2 mmol) in 30 mL methylene chloride. The reaction mixture was stirred for 2 h then concentrated in vacuo. The residue was purified by flash chromatography using 20% ethyl acetate/hexanes as eluent to give 0.290 g (42%) of the title compound as a white solid: mp 94–97° C., $^1$H NMR (CDCl$_3$) δ1.20 (m, 12H), 1.40 (m, 3H), 2.65 (q, 2H) 3.16 (dd, 1H), 3.98 (m, 1H), 4.05 (m, 1H), 4.40 ((m, 1H), 6.00 (d, 1H), 6.25 (dd, 1H), 6.95 (t, 1H), 7.18 (t, 2H).

EXAMPLE 7

Step A: Preparation of 2-fluoro-3-methyl-2-butenyl cyanoacetate

A solution of cyano acetic acid (2.25 g, 26.4 mmol) in 30 mL dry CH$_2$Cl$_2$ was cooled in ice water before 2.3 mL (26.4 mmol) of oxalyl chloride and 3 drops of DMF were added. The mixture was warmed to room temperature with stirring overnight before being added dropwise to an ice-cooled solution of 2.5 g (24 mmol) of 2-fluoro-4-methyl-2-buten-1-ol (Cane, D. E.; Yang, G.; Xue, Q.; Shin, J. H. *Biochemistry* (1995), 3418, 2471–9) and 3.7 mL (26.4 mmol) triethylamine. After stirring 3 h at room temperature, solvent was removed and the residue was partitioned between water and ether. The ether layer was separated and washed with brine. The combined aqueous washings were extracted with ether which was washed with brine. The combined ether extracts were dried (MgSO$_4$), and solvent was removed to afford 3.5 g of the title compound of Step A as an oil, $^1$H NMR (CDCl$_3$) δ1.7 (m, 6H), 3.5 (s, 2H), 4.85 (d, J=22 Hz, 2H).

Step B: Preparation of 2-cyano-4-fluoro-3,3-dimethyl-4-pentenoic acid

A solution of (3.5 g, 20.5 mmol) the product from Example 7, Step A in 25 mL hexamethyldisilazane was heated at reflux for 2 h. Solvent was removed and the residue was dissolved in 50 mL 1N HCl. The mixture was heated at reflux for 20 min. After cooling, the mixture was extracted with ether which was washed with brine and dried (MgSO$_4$). Removal of solvent gave 3.2 g of the title compound of Step B as an oil, $^1$H NMR (CDCl$_3$) δ1.4 (s, 3H), 1.45 (s, 3H), 3.8 (s, 1H), 4.55 (d of d, J=50, 4 Hz, 1H), 4.75 (d of d, J=25, 1 Hz, 1H), 6.5 (br s, 1H).

Step C: Preparation of (R)-2-[2-(2,5-difluorophenoxy)-1-methylethyl]-1H-isoindole-1,3(2H)-dione A solution of 15.8 g (77 mmol) of (R)-2-(2-hydroxy-1-methylethyl)-1H-isoindole-1,3(2H)-dione, 24.2 g (92 mmol) of triphenylphosphine and 10.0 g (77 mmol) of 2,5-difluorophenol was stirred while 18.2 mL (116 mmol) of diethylazodicarboxylate was added dropwise. After stirring at ambient temperature overnight, solvent was removed and the residue was dissolved in ethyl acetate. The ethyl acetate was washed with water and brine. Drying (MgSO$_4$) and removal of solvent gave an oil which was chromatographed on silica gel to give 15.6 g of the title compound of Step C as an oil, $^1$H NMR (CDCl$_3$) δ1.55 (d, 3H), 4.25 (m, 1H), 4.8 (m, 1H), 6.55 (m, 1H), 6.65 (m, 1H), 6.9 (m, 1H), 7.7 (m, 2H), 7.85 (m, 2H).

Step D: Preparation of 1-(2,5-difluorophenoxy)proponamine hydrochloride

A solution of 15.6 g (44.2 mmol) of (R)-2-[2-(2,5-difluorophenoxy-1-methylethyl]-1H-isoindole-1,3(2H)- dione and 7.7 mL of anhydrous hydrazine in 400 mL ethanol was heated at reflux for 2 h. Solids were filtered and rinsed with ethyl acetate. Solvent was removed and the residue was partitioned between ether and 1N HCl (aq). The aqueous layer was separated, basified with 50% sodium hydroxide and extracted with ether. The ether was washed with brine and dried (MgSO$_4$). After removal of solvent, the residue was redissolved in ether and 45 mL of 1N HCl in ether was added to form the hydrochloride salt precipitate. The precipitate was filtered and rinsed with ether affording 8.5 g of the title compound of Step D as a white solid, mp 127–129° C.

Step E: Preparation of [R-(R*,R*)]-2-cyano-N-[2-(2,5-difluorophenoxy)-1-methylethyl]-4-fluoro-3,3-dimethyl-4-pentenamide mixed 1:1 with [R-(R*,S*)]-2-cyano-N-[2-(2,5-difluorophenoxy)-1-methylethyl]-4-fluoro-3,3-dimethyl-4-pentenamide A solution of 370 mg (2.16 mmol) of the acid from Step A, 0.19 mL (2.15 mmol) oxalyl chloride and 2 drops DMF in 10 mL CH$_2$Cl$_2$ was stirred at room temperature overnight. This mixture was added to a solution of 400 mg (1.8 mmol) of the amine salt of Step D and 0.52 mL (3.7 mmol) triethylamine in 10 mL CH$_2$Cl$_2$. After stirring overnight, 0.3 g Amberlite IRA-78 resin was added and the mixture was filtered through silica gel, rinsing through with ethyl acetate. The filtrate was concentrated to give 570 mg of the title compound of Step E as a solid, mp 106–110° C.

EXAMPLE 8

Step A: Preparation of [R-(E)]-phenylmethyl [3-(2,5-difluorophenyl)-1-methyl-2-propenyl]carbamate A solution of 4.0 g (21 mmol) of (R)-phenylmethyl 2-methyl-1-aziridinecarboxylate (Dellaria, J. F. Jr.; Sallin, K. J. *Tetrahedron Lett*. (1990), 31, 2661), 5.0 g (35 mmol) of 2,5-difluorobenzaldehyde (Aldrich) and 6.5 g (26 mmol) of triphenylphosphine (Aldrich) in 100 mL isopropyl alcohol was heated at reflux for 4 h. The mixture was cooled to 22° C. and stirred 20 h. The reaction mixture was concentrated to an oil then purified by flash silica chromatography (5% ethyl acetate in hexanes) to give 4.0 g of title compound of Step A as a 4 to 5 mixture of cis to trans isomers as a white solid mp 82–84° C., $^1$H NMR (CDCl$_3$) trans isomer: δ7.35 (m, 5H), 7.10 (m, 1H), 6.95 (m, 2H), 6.60 (d, 1H), 6.25 (dd, 1H), 5.12 (s, 2H), 4.80 (m, 1H), 4.60 (m, 1H), 1.36 (d, 3H); cis isomer: δ7.35 (m, 5H), 7.10 (m, 1H), 6.95 (m, 2H), 6.40 (d, 1H), 5.65 (dd, 1H), 5.07 (s, 2H), 4.80 (m, 1H), 4.60 (m, 1H), 1.27 (d, 3H).

Step B: Preparation of [R-(E)]-4-(2,5-difluorophenyl)-3-buten-2-amine hydrochloride In a small flask, 3.1 g (9.8 mmol) of the product of Example 8, Step A was treated with 8 mL of 30% hydrogen bromide in acetic acid. The reaction mixture was stirred at 22° C. for 8 h. Diluted reaction mixture with 200 mL ethyl acetate then washed twice with 100 mL of 1N sodium hydroxide, then once with 50 mL brine. Extracted the ethyl acetate layer twice with 100 mL of 1N HCl. Treated the acidic aqueous layer with 250 mL of 1N sodium hydroxide. Then extracted this solution with ethyl acetate. Concentrated this final organic layer to give the free amine as an oil. Diluted the free amine oil in 100 mL of dry ether then treated with 20 mL of 1N HCl in ether. A white precipitate was filtered and dried to give 1.0 g of title compound of Step B as a 3 to 7 mixture of cis to trans isomers. Amine salt is a white solid, mp 133–136° C., $^1$H NMR ((CH$_3$)$_2$SO-d$_6$) trans isomer: δ8.30 (br s, 3H), 7.50 (m, 1H), 7.30 (m, 2H), 6.80 (d, 1H), 6.50 (dd, 1H), 4.00 (m, 1H), 1.39 (d, 3H); cis isomer: δ8.30 (br s, 3H), 7.50 (m, 1H), 7.30 (m, 2H), 6.62 (d, 1H), 5.90 (t, 1H), 4.00 (m, 1H), 1.31 (d, 3H).

Step C: Preparation of [1[R-(E)]-trans]-2,2-dichloro-N-[3-(2,5-difluorophenyl)-1-methyl-2-propenyl]-1-ethyl-3-methylcyclopropanecarboxamide In a separate flask 0.50 g (2.5 mmol) of (trans)-2,2-dichloro-1-ethyl-3-methylcyclopropanecarboxlic acid in 20 mL thionyl chloride was heated at reflux for 30 min. The reaction mixture was concentrated and the residue was dried in vacuo. The crude acid chloride was diluted in 20 mL of methylene chloride and added dropwise to a solution of 0.42 g (1.9 mmol) of [R-(E)]-4-(2,5-difluorophenyl)-3-buten-2-amine hydrochloride and 1.0 mL (7.1 mmol) of triethylamine in 20 mL of methylene chloride. The reaction mixture was stirred at 22° C. for 2 h then diluted with 100 mL methylene chloride and washed with 100 mL in HCl. The organic layer was concentrated to an oil. The crude amide was purified by flash silica chromatography using 20% ethyl acetate in hexanes as eluent to give 130 mg of a less polar trans isomer as an oil. $^1$H NMR (CDCl$_3$) δ7.10 (m, 1H), 6.95 (m, 2H), 6.65 (d, 1H), 6.30 (dd, 1H), 5.80 (br s, 1H), 4.05 (m, 1H), 2.20 (q, 1H), 2.00 (m, 1H), 1.60 (m, 1H), 1.40 (d, 3H), 1.20 (d, 3H), 1.00 (t, 3H) and 140 mg of a more polar trans isomer as a white solid, mp 102–105° C., $^1$H NMR (CDCl$_3$) δ7.10 (m, 1H), 6.95 (m, 2H), 6.70 (d, 1H), 6.28 (dd, 1H), 5.80 (br s, 1H), 4.85 (m, 1H), 2.23 (q, 1H), 2.00 (m, 1H), 1.60 (m, 1H), 1.40 (d, 3H), 1.20 (d, 3H), 1.00 (t, 3H).

By the procedures described herein together with methods known in the art, the following compounds of Tables 1 to 9 can be prepared. The following abbreviations are used in the Tables which follow: t=tertiary, n=normal, i=iso, c=cyclo, F=fluorine, Br=bromine, Cl=chlorine, I=iodine, Me=methyl, Et=ethyl, Pr=propyl, i-Pr=isopropyl, Bu=butyl, Ph=phenyl, CF$_3$=trifluoromethyl, SCF$_3$=trifluoromethylthio, CN=cyano and SiMe$_3$=trimethylsilyl.

TABLE 1

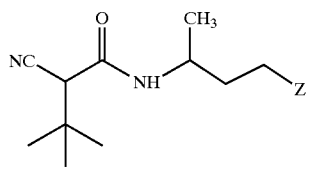

Z =

| Column 1 | Column 2 | Column 3 |
|---|---|---|
| 1 C$_6$H$_5$ | 2-n-Pr-6-CN—C$_6$H$_3$ | 2-CF$_3$-1H-pyrrol-1-yl |
| 2 2-F—C$_6$H$_4$ | 2-Cl-5-F—C$_6$H$_3$ | 2,3-diCl-1H-pyrrol-1-yl |
| 3 3-F—C$_6$H$_4$ | 2-F-3-Me—C$_6$H$_3$ | 2,4-diCl-1H-pyrrol-1-yl |
| 4 4-F—C$_6$H$_4$ | 2-F-5-Me—C$_6$H$_3$ | 3,4-diCl-1H-pyrrol-1-yl |

TABLE 1-continued

[Structure: NC-CH(t-Bu)-C(=O)-NH-CH(CH3)-CH2-CH2-Z]

Z =

| | Column 1 | Column 2 | Column 3 |
|---|---|---|---|
| 5 | 2-Cl—C$_6$H$_4$ | 3-F-6-Me—C$_6$H$_3$ | 2,3-diBr-1H-pyrrol-1-yl |
| 6 | 3-Cl—C$_6$H$_4$ | 2-thienyl | 2,4-diBr-1H-pyrrol-1-yl |
| 7 | 4-Cl—C$_6$H$_4$ | 3-F-2-thienyl | 4-F-5-Br-1H-pyrrol-1-yl |
| 8 | 2-Br—C$_6$H$_4$ | 4-F-2-thienyl | 2-Cl-3-Br-1H-pyrrol-1-yl |
| 9 | 3-Br—C$_6$H$_4$ | 5-Et-2-thienyl | 2-Cl-4-Br-1H-pyrrol-1-yl |
| 10 | 4-Br—C$_6$H$_4$ | 3-Cl-2-thienyl | 3-Cl-4-Br-1H-pyrrol-1-yl |
| 11 | 2-I—C$_6$H$_4$ | 4-Cl-2-thienyl | 3-Cl-5-Br-1H-pyrrol-1-yl |
| 12 | 3-I—C$_6$H$_4$ | 5-Cl-2-thienyl | 4-F-5-Me-1H-pyrrol-1-yl |
| 13 | 4-I—C$_6$H$_4$ | 3-(C≡CH)-2-thienyl | 2-Cl-3-Me-1H-pyrrol-1-yl |
| 14 | 2-Me—C$_6$H$_4$ | 4-Br-2-thienyl | 2-Cl-4-Me-1H-pyrrol-1-yl |
| 15 | 3-Me—C$_6$H$_4$ | 5-Br-2-thienyl | 2-Cl-5-Me-1H-pyrrol-1-yl |
| 16 | 4-Me—C$_6$H$_4$ | 3-(CH=CH$_2$)-2-thienyl | 3-Cl-4-Me-1H-pyrrol-1-yl |
| 17 | 2-Et—C$_6$H$_4$ | 3,4-diF-2-thienyl | 3-Cl-5-Me-1H-pyrrol-1-yl |
| 18 | 2-CN—C$_6$H$_4$ | 3-F-5-Br-2-thienyl | 4-Cl-5-Me-1H-pyrrol-1-yl |
| 19 | 2-CF$_3$—C$_6$H$_4$ | 4-F-5-Br-2-thienyl | 2-Br-3-Me-1H-pyrrol-1-yl |
| 20 | 2-n-Pr—C$_6$H$_4$ | 3-Br-4-F-2-thienyl | 2-Br-4-Me-1H-pyrrol-1-yl |
| 21 | 2-i-Pr—C$_6$H$_4$ | 3-Br-5-F-2-thienyl | 2-Br-5-Me-1H-pyrrol-1-yl |
| 22 | 2-n-Bu—C$_6$H$_4$ | 4-Br-5-F-2-thienyl | 3-Br-4-Me-1H-pyrrol-1-yl |
| 23 | 2-SiMe$_3$—C$_6$H$_4$ | 3-F-4-Me-2-thienyl | 3-Br-5-Me-1H-pyrrol-1-yl |
| 24 | 2-CH$_2$F—C$_6$H$_4$ | 3-F-5-Me-2-thienyl | 4-Br-5-Me-1H-pyrrol-1-yl |
| 25 | 3-CH$_2$F—C$_6$H$_4$ | 4-F-5-Me-2-thienyl | 2-n-Pr-3-F-1H-pyrrol-1-yl |
| 26 | 2-CH$_2$CN—C$_6$H$_4$ | 3-Me-4-F-2-thienyl | 2-n-Pr-4-F-1H-pyrrol-1-yl |
| 27 | 2-CH$_2$CH$_2$F—C$_6$H$_4$ | 3-Me-5-F-2-thienyl | 2-n-Pr-5-F-1H-pyrrol-1-yl |
| 28 | 2-(CH=CH$_2$)—C$_6$H$_4$ | 4-Me-5-F-2-thienyl | 2-n-Pr-3-Cl-1H-pyrrol-1-yl |
| 29 | 2-(CH$_2$CH=CH$_2$)—C$_6$H$_4$ | 3-Me-5-Cl-2-thienyl | 2-n-Pr-4-Cl-1H-pyrrol-1-yl |
| 30 | 2-(CH=CHCN)—C$_6$H$_4$ | 3-Br-5-Me-2-thienyl | 2-n-Pr-5-Cl-1H-pyrrol-1-yl |
| 31 | 2-(C≡CH)—C$_6$H$_4$ | 3-Me-5-Br-2-thienyl | 2-n-Pr-3-Br-1H-pyrrol-1-yl |
| 32 | 2-(CH$_2$C≡CH)—C$_6$H$_4$ | 4-Me-5-Br-2-thienyl | 2-n-Pr-4-Br-1H-pyrrol-1-yl |
| 33 | 2-(C≡CMe)—C$_6$H$_4$ | 3-n-Pr-4-F-2-thienyl | 2-n-Pr-5-Br-1H-pyrrol-1-yl |
| 34 | 2-(t-Bu)—C$_6$H$_4$ | 3-n-Pr-5-F-2-thienyl | 2-n-Pr-3-Me-1H-pyrrol-1-yl |
| 35 | 2-[CH(F)Me]—C$_6$H$_4$ | 3-CN-5-Br-2-thienyl | 2-n-Pr-4-Me-1H-pyrrol-1-yl |
| 36 | 2,3-diF—C$_6$H$_3$ | 3-thienyl | 2-n-Pr-5-Me-1H-pyrrol-1-yl |
| 37 | 2,4-diF—C$_6$H$_3$ | 2-F-3-thienyl | 2-CN-3-F-1H-pyrrol-1-yl |
| 38 | 2,5-diF—C$_6$H$_3$ | 4-F-3-thienyl | 2-CN-4-F-1H-pyrrol-1-yl |
| 39 | 2,6-diF—C$_6$H$_3$ | 5-F-3-thienyl | 2-CN-5-F-1H-pyrrol-1-yl |
| 40 | 3,4-diF—C$_6$H$_3$ | 2-Cl-3-thienyl | 2-CN-3-Cl-1H-pyrrol-1-yl |
| 41 | 3,5-diF—C$_6$H$_3$ | 4-Cl-3-thienyl | 2-CN-4-Cl-1H-pyrrol-1-yl |
| 42 | 2,3-diCl—C$_6$H$_3$ | 5-Cl-3-thienyl | 2-CN-5-Cl-1H-pyrrol-1-yl |
| 43 | 2,4-diCl—C$_6$H$_3$ | 2-CN-3-thienyl | 2-CN-3-Br-1H-pyrrol-1-yl |
| 44 | 2,5-diCl—C$_6$H$_3$ | 5-CN-3-thienyl | 2-CN-4-Br-1H-pyrrol-1-yl |
| 45 | 2,6-diCl—C$_6$H$_3$ | 2-Br-3-thienyl | 2-CN-5-Br-1H-pyrrol-1-yl |
| 46 | 3,4-diCl—C$_6$H$_3$ | 5-Br-3-thienyl | 2-CN-3-Me-1H-pyrrol-1-yl |
| 47 | 3,5-diCl—C$_6$H$_3$ | 2-n-Pr-3-thienyl | 2-CN-4-Me-1H-pyrrol-1-yl |
| 48 | 2,5-diBr—C$_6$H$_3$ | 2-(CH$_2$CN)-3-thienyl | 2-CN-5-Me-1H-pyrrol-1-yl |
| 49 | 2-Br-5-Cl—C$_6$H$_3$ | 2,5-diCl-3-thienyl | 2-CN-5-n-Pr-1H-pyrrol-1-yl |
| 50 | 3-Br-6-Cl—C$_6$H$_3$ | 2,5-diBr-3-thienyl | 2,3,4-triCl-1H-pyrrol-1-yl |
| 51 | 2-Br-5-Me—C$_6$H$_3$ | 2-F-5-Cl-3-thienyl | 2,3,5-triCl-1H-pyrrol-1-yl |
| 52 | 3-Br-6-Me—C$_6$H$_3$ | 2-Cl-5-F-3-thienyl | 2,3-diCl-4-Me-1H-pyrrol-1-yl |
| 53 | 2-CN-3-F—C$_6$H$_3$ | 2-F-5-Br-3-thienyl | 2,3-diCl-5-Me-1H-pyrrol-1-yl |
| 54 | 2-CN-5-F—C$_6$H$_3$ | 2-Br-5-F-3-thienyl | 2,4-diCl-3-Me-1H-pyrrol-1-yl |
| 55 | 2-CN-6-F—C$_6$H$_3$ | 2-Cl-5-Br-3-thienyl | 2,4-diCl-5-Me-1H-pyrrol-1-yl |
| 56 | 2-CN-3-Cl—C$_6$H$_3$ | 2-Br-5-Cl-3-thienyl | 2,5-diCl-3-Me-1H-pyrrol-1-yl |
| 57 | 2-CN-5-Cl—C$_6$H$_3$ | 2-n-Pr-5-F-3-thienyl | 2-CN-3,5-diMe-1H-pyrrol-1-yl |
| 58 | 2-CN-6-Cl—C$_6$H$_3$ | 2-CN-5-F-3-thienyl | 2-CN-4,5-diMe-1H-pyrrol-1-yl |
| 59 | 2-CN-5-Br—C$_6$H$_3$ | 2-CN-5-Cl-3-thienyl | 2-CN-3,4-diCl-1H-pyrrol-1-yl |
| 60 | 2-CN-3-CF$_3$—C$_6$H$_3$ | 2-CN-5-Br-3-thienyl | 2-CN-3,5-diCl-1H-pyrrol-1-yl |
| 61 | 2-CN-3-Me—C$_6$H$_3$ | 2-CN-5-Me-3-thienyl | 2-CN-4,5-diCl-1H-pyrrol-1-yl |
| 62 | 2-CN-5-Me—C$_6$H$_3$ | 1H-pyrrol-1-yl | 2-CN-3-Cl-4-Me-1H-pyrrol-1-yl |
| 63 | 2-CN-6-Me—C$_6$H$_3$ | 2-F-1H-pyrrol-1-yl | 2-CN-3-Cl-5-Me-1H-pyrrol-1-yl |
| 64 | 2-Br-4-F—C$_6$H$_3$ | 3-F-1H-pyrrol-1-yl | 2-CN-3-Me-4-Cl-1H-pyrrol-1-yl |
| 65 | 2-Br-5-F—C$_6$H$_3$ | 2-I-1H-pyrrol-1-yl | 2-CN-3-Me-5-Cl-1H-pyrrol-1-yl |
| 66 | 2-Cl-3-Me—C$_6$H$_3$ | 2-Cl-1H-pyrrol-1-yl | 2-CN-4-Me-5-Cl-1H-pyrrol-1-yl |
| 67 | 2-Cl-5-Me—C$_6$H$_3$ | 3-Cl-1H-pyrrol-1-yl | 2-CN-4-Cl-5-Me-1H-pyrrol-1-yl |
| 68 | 2-Cl-6-Me—C$_6$H$_3$ | 2-CN-1H-pyrrol-1-yl | 2-CN-4-Br-5-Me-1H-pyrrol-1-yl |
| 69 | 3-Cl-5-Me—C$_6$H$_3$ | 2-Br-1H-pyrrol-1-yl | 2,3,4,5-tetraCl-1H-pyrrol-1-yl |
| 70 | 2-n-Pr-3-F—C$_6$H$_3$ | 2-n-Pr-1H-pyrrol-1-yl | 2,3,5-triCl-4-Me-1H-pyrrol-1-yl |

TABLE 1-continued

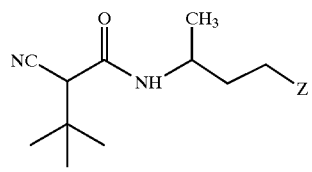

Z =

| | Column 1 | Column 2 | Column 3 |
|---|---|---|---|
| 71 | 2-n-Pr-4-F—$C_6H_3$ | 2-i-Pr-1H-pyrrol-1-yl | 2,5-diCl-3,4-diMe-1H-pyrrol-1-yl |
| 72 | 2-n-Pr-5-F—$C_6H_3$ | 2-n-Bu-1H-pyrrol-1-yl | 2,3,4-triCl-5-CN-1H-pyrrol-1-yl |
| 73 | 2-n-Pr-3-Cl—$C_6H_3$ | 2-$CH_2CN$-1H-pyrrol-1-yl | 2,3,4-triMe-5-CN-1H-pyrrol-1-yl |
| 74 | 2-n-Pr-5-Cl—$C_6H_3$ | 2-t-Bu-1H-pyrrol-1-yl | 2,3-Cl-4-Me-5-CN-1H-pyrrol-1-yl |
| 75 | 2-n-Pr-5-Br—$C_6H_3$ | 5-Et-1H-pyrrol-1-yl | 2,4-Cl-3-Me-5-CN-1H-pyrrol-1-yl |
| 76 | 2-n-Pr-5-Me—$C_6H_3$ | 2-(C≡CH)-1H-pyrrol-1-yl | 3,4-Cl-2-Me-5-CN-1H-pyrrol-1-yl |

TABLE 2

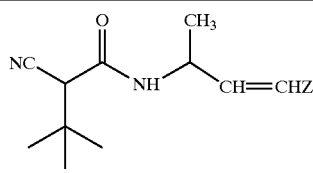

Z =

| | Column 1 | Column 2 | Column 3 |
|---|---|---|---|
| 1 | $C_6H_5$ | 2-CN-5-I—$C_6H_3$ | 3-$CH_2Cl$-2-thienyl |
| 2 | 2-F—$C_6H_4$ | 2-CN-6-Me—$C_6H_3$ | 3-$CH_2Br$-2-thienyl |
| 3 | 3-F—$C_6H_4$ | 2-Br-4-F—$C_6H_3$ | 3-($CH_2CN$)-2-thienyl |
| 4 | 4-F—$C_6H_4$ | 2-Br-5-F—$C_6H_3$ | 5-$SiMe_3$-2-thienyl |
| 5 | 2-Cl—$C_6H_4$ | 3-Br-6-F—$C_6H_3$ | 3-(CH=$CH_2$)-2-thienyl |
| 6 | 3-Cl—$C_6H_4$ | 2-Cl-3-Me—$C_6H_3$ | 3-(CH=CHMe)-2-thienyl |
| 7 | 4-Cl—$C_6H_4$ | 2-Cl-5-Me—$C_6H_3$ | 3-($CH_2CH$=$CH_2$)-2-thienyl |
| 8 | 2-Br—$C_6H_4$ | 2-Cl-6-Me—$C_6H_3$ | 3-($CH_2C$≡CH)-2-thienyl |
| 9 | 3-Br—$C_6H_4$ | 3-Cl-5-Me—$C_6H_3$ | 3-(C≡CMe)-2-thienyl |
| 10 | 4-Br—$C_6H_4$ | 3-Cl-6-Me—$C_6H_3$ | 3-(CH=CHCN)-2-thienyl |
| 11 | 2-I—$C_6H_4$ | 2-n-Pr-3-F—$C_6H_3$ | 3,5-diF-2-thienyl |
| 12 | 3-I—$C_6H_4$ | 2-n-Pr-5-F—$C_6H_3$ | 3,5-diCl-2-thienyl |
| 13 | 4-I—$C_6H_4$ | 2-n-Pr-6-F—$C_6H_3$ | 3-F-5-Cl-2-thienyl |
| 14 | 2-Me—$C_6H_4$ | 2-n-Pr-3-Cl—$C_6H_3$ | 3-Cl-5-F-2-thienyl |
| 15 | 3-Me—$C_6H_4$ | 2-n-Pr-5-Cl—$C_6H_3$ | 3-F-5-Br-2-thienyl |
| 16 | 4-Me—$C_6H_4$ | 2-n-Pr-5-Br—$C_6H_3$ | 3-Br-4-F-2-thienyl |
| 17 | 2-Et—$C_6H_4$ | 2-n-Pr-5-Me—$C_6H_3$ | 3-Br-5-F-2-thienyl |
| 18 | 3-Et—$C_6H_4$ | 2-n-Pr-6-CN—$C_6H_3$ | 3-F-5-Me-2-thienyl |
| 19 | 2-CN—$C_6H_4$ | 2-Cl-3-F—$C_6H_3$ | 3-Me-5-F-2-thienyl |
| 20 | 2-$CF_3$—$C_6H_4$ | 2-Cl-5-F—$C_6H_3$ | 3-Br-5-Cl-2-thienyl |
| 21 | 2-n-Pr—$C_6H_4$ | 2-Cl-6-F—$C_6H_3$ | 3-Cl-5-Me-2-thienyl |
| 22 | 3-n-Pr—$C_6H_4$ | 3-Cl-2-F—$C_6H_3$ | 3-Me-5-Cl-2-thienyl |
| 23 | 2-i-Pr—$C_6H_4$ | 3-Cl-6-F—$C_6H_3$ | 3-Br-5-Me-2-thienyl |
| 24 | 3-i-Pr—$C_6H_4$ | 4-Cl-2-F—$C_6H_3$ | 3-Me-5-Br-2-thienyl |
| 25 | 3-$SCF_3$—$C_6H_4$ | 2-F-3-Me—$C_6H_3$ | 3-n-Pr-5-Cl-2-thienyl |
| 26 | 2-n-Bu—$C_6H_4$ | 2-F-5-Me—$C_6H_3$ | 3-CN-5-F-2-thienyl |
| 27 | 3-$SiMe_3$—$C_6H_4$ | 2-F-6-Me—$C_6H_3$ | 3-CN-5-Cl-2-thienyl |
| 28 | 3-$SCF_2H$—$C_6H_4$ | 3-F-6-Me—$C_6H_3$ | 3-CN-5-Br-2-thienyl |
| 29 | 2-$CH_2F$—$C_6H_4$ | 2,3,4-triF—$C_6H_2$ | 3-CN-5-Me-2-thienyl |
| 30 | 3-$CH_2F$—$C_6H_4$ | 2,3,5-triF—$C_6H_2$ | 3-thienyl |
| 31 | 2-$CH_2Cl$—$C_6H_4$ | 2,3,6-triF—$C_6H_2$ | 2-F-3-thienyl |
| 32 | 2-$CH_2Br$—$C_6H_4$ | 2,4,5-triF—$C_6H_2$ | 4-F-3-thienyl |
| 33 | 2-$CH_2CN$—$C_6H_4$ | 2,3,5-triCl—$C_6H_2$ | 5-F-3-thienyl |
| 34 | 2-$CH_2CH_2F$—$C_6H_4$ | 2,3,6-triCl—$C_6H_2$ | 2-I-3-thienyl |
| 35 | 2-$CH_2CH_2Cl$—$C_6H_4$ | 2,4,6-triCl—$C_6H_2$ | 5-I-3-thienyl |
| 36 | 2-$CH_2CH_2CN$—$C_6H_4$ | 2,5-diF-3-Cl—$C_6H_2$ | 2-Me-3-thienyl |
| 37 | 2-(CH=$CH_2$)—$C_6H_4$ | 2,5-diF-6-Cl—$C_6H_2$ | 5-Me-3-thienyl |
| 38 | 2-(CH=CHMe)—$C_6H_4$ | 2,3-diCl-5-F—$C_6H_2$ | 2-Et-3-thienyl |
| 39 | 2-($CH_2CH$=$CH_2$)—$C_6H_4$ | 2,3-diCl-6-F—$C_6H_2$ | 2-Cl-3-thienyl |
| 40 | 2-(CH=CHCN)—$C_6H_4$ | 2,5-diCl-3-F—$C_6H_2$ | 4-Cl-3-thienyl |
| 41 | 2-(C≡CH)—$C_6H_4$ | 2,5-diCl-6-F—$C_6H_2$ | 5-Cl-3-thienyl |
| 42 | 2-($CH_2C$≡CH)—$C_6H_4$ | 2,6-diCl-3-F—$C_6H_2$ | 2-CN-3-thienyl |

TABLE 2-continued

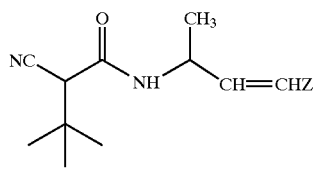

Z =

| | Column 1 | Column 2 | Column 3 |
|---|---|---|---|
| 43 | 2-(C≡CMe)—$C_6H_4$ | 2,3-diF-5-Me—$C_6H_2$ | 2-(C≡CH)-3-thienyl |
| 44 | 2-(t-Bu)—$C_6H_4$ | 2,5-diF-3-Me—$C_6H_2$ | 2-Br-3-thienyl |
| 45 | 2-($CH_2$C≡CMe)—$C_6H_4$ | 2,5-diF-6-Me—$C_6H_2$ | 5-Br-3-thienyl |
| 46 | 2-[CH(F)Me]—$C_6H_4$ | 2-CN-3,5-diF—$C_6H_2$ | 2-n-Pr-3-thienyl |
| 47 | 2-[CH(Cl)Me]—$C_6H_4$ | 2-CN-3,6-diF—$C_6H_2$ | 2-i-Pr-3-thienyl |
| 48 | 2-[CH(Br)Me]—$C_6H_4$ | 2-CN-5,6-diF—$C_6H_2$ | 2-n-Bu-3-thienyl |
| 49 | 2-[CH(CN)Me]—$C_6H_4$ | 2-CN-3-F-5-Cl—$C_6H_2$ | 2-$CH_2$F-3-thienyl |
| 50 | 2-[CH(CN)$CH_2$Me]—$C_6H_4$ | 2-CN-3-Me-5-Cl—$C_6H_2$ | 2-($CH_2$CN)-3-thienyl |
| 51 | 2-($CH_2CH_2$C≡CH)—$C_6H_4$ | 2-CN-3-Me-5-F—$C_6H_2$ | 2-t-Bu-3-thienyl |
| 52 | 2,3-diF—$C_6H_3$ | 2-CN-5-F-6-Cl—$C_6H_2$ | 2-($CH_2CH_2$CN)-3-thienyl |
| 53 | 2,4-diF—$C_6H_3$ | 2-Cl-3-F-5-Me—$C_6H_2$ | 2-(CH=$CH_2$)-3-thienyl |
| 54 | 2,5-diF—$C_6H_3$ | 2-F-3-Cl-5-Me—$C_6H_2$ | 2-(CH=CHMe)-3-thienyl |
| 55 | 2,6-diF—$C_6H_3$ | 2,3,4,5-tetraF—$C_6$H | 2-($CH_2$CH=$CH_2$)-3-thienyl |
| 56 | 3,4-diF—$C_6H_3$ | 2,3,4,6-tetraF—$C_6$H | 2-($CH_2$C≡CH)-3-thienyl |
| 57 | 3,5-diF—$C_6H_3$ | 2,3,5,6-tetraF—$C_6$H | 2-(C≡CMe)-3-thienyl |
| 58 | 2,5-diCl—$C_6H_3$ | 2-thienyl | 2-(CH=CHCN)-3-thienyl |
| 59 | 2,6-diCl—$C_6H_3$ | 3-F-2-thienyl | 2,4-diF-3-thienyl |
| 60 | 3,5-diCl—$C_6H_3$ | 4-F-2-thienyl | 2,5-diF-3-thienyl |
| 61 | 2,5-diBr—$C_6H_3$ | 5-F-2-thienyl | 4,5-diF-3-thienyl |
| 62 | 2-Br-5-Cl—$C_6H_3$ | 5-I-2-thienyl | 2,5-diCl-3-thienyl |
| 63 | 2-Br-5-Me—$C_6H_3$ | 3-Me-2-thienyl | 2,5-diBr-3-thienyl |
| 64 | 2-CN-3-F—$C_6H_3$ | 5-Me-2-thienyl | 2-Cl-5-Br-3-thienyl |
| 65 | 2-CN-4-F—$C_6H_3$ | 3-Cl-2-thienyl | 2-Br-5-Cl-3-thienyl |
| 66 | 2-CN-5-F—$C_6H_3$ | 4-Cl-2-thienyl | 2-Br-5-Me-3-thienyl |
| 67 | 2-CN-6-F—$C_6H_3$ | 5-Cl-2-thienyl | 2-Me-5-Br-3-thienyl |
| 68 | 2-CN-3-Cl—$C_6H_3$ | 3-CN-2-thienyl | 2-n-Pr-5-Cl-3-thienyl |
| 69 | 2-CN-5-Cl—$C_6H_3$ | 5-(C≡CH)-2-thienyl | 2-n-Pr-5-Br-3-thienyl |
| 70 | 2-CN-6-Cl—$C_6H_3$ | 3-Br-2-thienyl | 2-CN-5-Cl-3-thienyl |
| 71 | 2-CN-5-Br—$C_6H_3$ | 5-Br-2-thienyl | 2-CN-5-Br-3-thienyl |
| 72 | 2-CN-3-I—$C_6H_3$ | 3-n-Pr-2-thienyl | 2-CN-5-Me-3-thienyl |
| 73 | 2-CN-3-Me—$C_6H_3$ | 5-n-Pr-2-thienyl | 2-CN-5-t-Bu—$C_6H_3$ |
| 74 | 2-CN-5-Me—$C_6H_3$ | 5-i-Pr-2-thienyl | |

TABLE 3

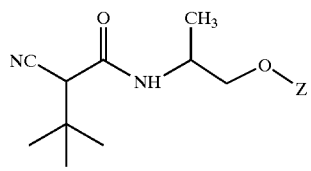

Z =

| | Column 1 | Column 2 | Column 3 |
|---|---|---|---|
| 1 | $C_6H_5$ | 2-CN-3-Cl—$C_6H_3$ | 2,3,5,6-tetraCl—$C_6$H |
| 2 | 2-F—$C_6H_4$ | 2-CN-4-Cl—$C_6H_3$ | 2,3,5-triCl-6-CN—$C_6$H |
| 3 | 3-F—$C_6H_4$ | 2-CN-5-Cl—$C_6H_3$ | 2,3,4-triF-6-CN—$C_6$H |
| 4 | 4-F—$C_6H_4$ | 2-CN-6-Cl—$C_6H_3$ | 2,5-diCl-3,6-diF—$C_6$H |
| 5 | 2-Cl—$C_6H_4$ | 2-CN-5-Br—$C_6H_3$ | 2,5-diF-3-Cl-6-CN—$C_6$H |
| 6 | 3-Cl—$C_6H_4$ | 2-CN-3-I—$C_6H_3$ | 1H-pyrrol-1-yl |
| 7 | 4-Cl—$C_6H_4$ | 2-CN-3-$CF_3$—$C_6H_3$ | 2-F-1H-pyrrol-1-yl |
| 8 | 2-Br—$C_6H_4$ | 2-CN-6-$CF_3$—$C_6H_3$ | 3-F-1H-pyrrol-1-yl |
| 9 | 3-Br—$C_6H_4$ | 2-CN-3-Me—$C_6H_3$ | 2-I-1H-pyrrol-1-yl |
| 10 | 4-Br—$C_6H_4$ | 2-CN-5-Me—$C_6H_3$ | 2-Cl-1H-pyrrol-1-yl |
| 11 | 2-I—$C_6H_4$ | 2-Br-4-F—$C_6H_3$ | 3-Cl-1H-pyrrol-1-yl |
| 12 | 3-I—$C_6H_4$ | 2-Br-5-F—$C_6H_3$ | 2-CN-1H-pyrrol-1-yl |
| 13 | 4-I—$C_6H_4$ | 3-Br-6-F—$C_6H_3$ | 2-Br-1H-pyrrol-1-yl |
| 14 | 2-Me—$C_6H_4$ | 2-Cl-3-Me—$C_6H_3$ | 2-n-Pr-1H-pyrrol-1-yl |
| 15 | 3-Me—$C_6H_4$ | 2-Cl-5-Me—$C_6H_3$ | 2-n-Bu-1H-pyrrol-1-yl |
| 16 | 4-Me—$C_6H_4$ | 3-Cl-5-Me—$C_6H_3$ | 2-t-Bu-1H-pyrrol-1-yl |

TABLE 3-continued

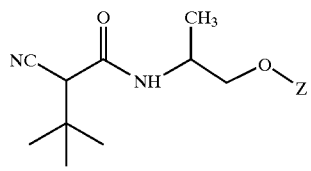

Z =

| | Column 1 | Column 2 | Column 3 |
|---|---|---|---|
| 17 | 2-Et—$C_6H_4$ | 2-n-Pr-3-F—$C_6H_3$ | 2,3-diCl-1H-pyrrol-1-yl |
| 18 | 3-Et—$C_6H_4$ | 2-n-Pr-4-F—$C_6H_3$ | 2,4-diCl-1H-pyrrol-1-yl |
| 19 | 2-CN—$C_6H_4$ | 2-n-Pr-5-F—$C_6H_3$ | 2,5-diCl-1H-pyrrol-1-yl |
| 20 | 2-$CF_3$—$C_6H_4$ | 2-n-Pr-6-F—$C_6H_3$ | 2,3-diBr-1H-pyrrol-1-yl |
| 21 | 2-n-Pr—$C_6H_4$ | 2-n-Pr-3-Cl—$C_6H_3$ | 2,4-diBr-1H-pyrrol-1-yl |
| 22 | 3-n-Pr—$C_6H_4$ | 2-n-Pr-5-Cl—$C_6H_3$ | 2,5-diBr-1H-pyrrol-1-yl |
| 23 | 2-i-Pr—$C_6H_4$ | 2-n-Pr-5-Br—$C_6H_3$ | 2-Cl-3-Br-1H-pyrrol-1-yl |
| 24 | 3-i-Pr—$C_6H_4$ | 2-n-Pr-5-Me—$C_6H_3$ | 2-Cl-4-Br-1H-pyrrol-1-yl |
| 25 | 2-n-Bu—$C_6H_4$ | 2-Cl-3-F—$C_6H_3$ | 2-Cl-5-Br-1H-pyrrol-1-yl |
| 26 | 3-$SiMe_3$—$C_6H_4$ | 2-Cl-4-F—$C_6H_3$ | 3-Cl-5-Br-1H-pyrrol-1-yl |
| 27 | 2-$CH_2F$—$C_6H_4$ | 2-Cl-5-F—$C_6H_3$ | 4-Cl-5-Br-1H-pyrrol-1-yl |
| 28 | 3-$CH_2F$—$C_6H_4$ | 2-Cl-6-F—$C_6H_3$ | 2-Cl-3-Me-1H-pyrrol-1-yl |
| 29 | 2-$CH_2Cl$—$C_6H_4$ | 3-Cl-2-F—$C_6H_3$ | 2-Cl-4-Me-1H-pyrrol-1-yl |
| 30 | 2-$CH_2Br$—$C_6H_4$ | 3-Cl-6-F—$C_6H_3$ | 2-Cl-5-Me-1H-pyrrol-1-yl |
| 31 | 2-$CH_2CN$—$C_6H_4$ | 2-F-3-Me—$C_6H_3$ | 2-Br-3-Me-1H-pyrrol-1-yl |
| 32 | 2-$CH_2CH_2F$—$C_6H_4$ | 2-F-5-Me—$C_6H_3$ | 2-Br-4-Me-1H-pyrrol-1-yl |
| 33 | 2-$CH_2CH_2Cl$—$C_6H_4$ | 2-F-6-Me—$C_6H_3$ | 2-Br-5-Me-1H-pyrrol-1-yl |
| 34 | 2-$CH_2CH_2CN$—$C_6H_4$ | 3-F-6-Me—$C_6H_3$ | 3-Br-4-Me-1H-pyrrol-1-yl |
| 35 | 2-(CH=$CH_2$)—$C_6H_4$ | 2,3,4-triF—$C_6H_2$ | 2-CN-3-Cl-1H-pyrrol-1-yl |
| 36 | 2-(CH=CHMe)—$C_6H_4$ | 2,3,5-triF—$C_6H_2$ | 2-CN-4-Cl-1H-pyrrol-1-yl |
| 37 | 2-($CH_2CH$=$CH_2$)—$C_6H_4$ | 2,3,6-triF—$C_6H_2$ | 2-CN-5-Cl-1H-pyrrol-1-yl |
| 38 | 2-(C≡CH)—$C_6H_4$ | 2,4,5-triF—$C_6H_2$ | 2-CN-3-Br-1H-pyrrol-1-yl |
| 39 | 2-($CH_2C$≡CH)—$C_6H_4$ | 2,4,6-triF—$C_6H_2$ | 2-CN-4-Br-1H-pyrrol-1-yl |
| 40 | 2-(C≡CMe)—$C_6H_4$ | 2,3,5-triCl—$C_6H_2$ | 2-CN-5-Br-1H-pyrrol-1-yl |
| 41 | 2-(C≡$CCH_2Me$)—$C_6H_4$ | 2,3,6-triCl—$C_6H_2$ | 2-CN-3-Me-1H-pyrrol-1-yl |
| 42 | 2-(t-Bu)—$C_6H_4$ | 2,3-diF-5-Cl—$C_6H_2$ | 2-CN-4-Me-1H-pyrrol-1-yl |
| 43 | 2-[CH(F)Me]—$C_6H_4$ | 2,3-diF-6-Cl—$C_6H_2$ | 2-CN-5-Me-1H-pyrrol-1-yl |
| 44 | 2-[CH(Cl)Me]—$C_6H_4$ | 2,5-diF-3-Cl—$C_6H_2$ | 2-CN-5-n-Pr-1H-pyrrol-1-yl |
| 45 | 2-[CH(Br)Me]—$C_6H_4$ | 2,5-diF-6-Cl—$C_6H_2$ | 2,3,4-triCl-1H-pyrrol-1-yl |
| 46 | 2-[CH(CN)Me]—$C_6H_4$ | 2,6-diF-3-Cl—$C_6H_2$ | 2,3,5-triCl-1H-pyrrol-1-yl |
| 47 | 2-[CH=C(Me)$_2$]—$C_6H_4$ | 2,3-diCl-5-F—$C_6H_2$ | 2,3-diCl-4-Me-1H-pyrrol-1-yl |
| 48 | 2-[CH(Me)CH=$CH_2$]—$C_6H_4$ | 2,5-diCl-3-F—$C_6H_2$ | 2,3-diCl-5-Me-1H-pyrrol-1-yl |
| 49 | 2-($CH_2C(Me)$=$CH_2$)—$C_6H_4$ | 2,5-diCl-6-F—$C_6H_2$ | 2,4-diCl-3-Me-1H-pyrrol-1-yl |
| 50 | 2-($CH_2CH_2C$≡CH)—$C_6H_4$ | 2,3-diF-5-Me—$C_6H_2$ | 2,4-diCl-5-Me-1H-pyrrol-1-yl |
| 51 | 2,3-diF—$C_6H_3$ | 2,5-diF-3-Me—$C_6H_2$ | 2,5-diCl-3-Me-1H-pyrrol-1-yl |
| 52 | 2,4-diF—$C_6H_3$ | 2,5-diF-6-Me—$C_6H_2$ | 2-CN-3,5-diMe-1H-pyrrol-1-yl |
| 53 | 2,5-diF—$C_6H_3$ | 2,5-diCl-3-Me—$C_6H_2$ | 2-CN-4,5-diMe-1H-pyrrol-1-yl |
| 54 | 2,6-diF—$C_6H_3$ | 2,5-diCl-6-Me—$C_6H_2$ | 2-CN-3,5-diCl-1H-pyrrol-1-yl |
| 55 | 3,4-diF—$C_6H_3$ | 2-CN-3,5-diMe—$C_6H_2$ | 2-CN-4,5-diCl-1H-pyrrol-1-yl |
| 56 | 3,5-diF—$C_6H_3$ | 2-CN-3,5-diCl—$C_6H_2$ | 2-CN-3-Cl-4-Me-1H-pyrrol-1-yl |
| 57 | 2,3-diCl—$C_6H_3$ | 2-CN-3,5-diF—$C_6H_2$ | 2-CN-3-Cl-5-Me-1H-pyrrol-1-yl |
| 58 | 2,4-diCl—$C_6H_3$ | 2-CN-5,6-diF—$C_6H_2$ | 2-CN-3-Me-4-Cl-1H-pyrrol-1-yl |
| 59 | 2,5-diCl—$C_6H_3$ | 2-CN-3-F-5-Cl—$C_6H_2$ | 2-CN-3-Me-5-Cl-1H-pyrrol-1-yl |
| 60 | 2,6-diCl—$C_6H_3$ | 2-CN-3-Me-5-Cl—$C_6H_2$ | 2-CN-4-Me-5-Cl-1H-pyrrol-1-yl |
| 61 | 3,4-diCl—$C_6H_3$ | 2-CN-3-Me-5-F—$C_6H_2$ | 2-CN-4-Cl-5-Me-1H-pyrrol-1-yl |
| 62 | 3,5-diCl—$C_6H_3$ | 2-CN-5-F-6-Cl—$C_6H_2$ | 2-CN-4-Br-5-Me-1H |
| 63 | 2,5-diBr—$C_6H_3$ | 2-Cl-3-F-5-Me—$C_6H_2$ | 2,3,4,5-tetraCl-1H-pyrrol-1-yl |
| 64 | 2-Br-5-Cl—$C_6H_3$ | 2-Cl-3-F-6-Me—$C_6H_2$ | 2,3,5-triCl-4-Me-1H-pyrrol-1-yl |
| 65 | 3-Br-6-Cl—$C_6H_3$ | 2-F-3-Cl-5-Me—$C_6H_2$ | 2,5-diCl-3,4-diMe-1H-pyrrol-1-yl |
| 66 | 2-Br-5-Me—$C_6H_3$ | 2,3,4,5-tetraF—$C_6H$ | 2,3,4-triCl-5-CN-1H-pyrrol-1-yl |
| 67 | 3-Br-6-Me—$C_6H_3$ | 2,3,4,6-tetraF—$C_6H$ | 2,3,4-triMe-5-CN-1H-pyrrol-1-yl |
| 68 | 2-CN-3-F—$C_6H_3$ | 2,3,5,6-tetraF—$C_6H$ | 2,3-Cl-4-Me-5-CN-1H-pyrrol-1-yl |
| 69 | 2-CN-4-F—$C_6H_3$ | 2,3,4,5-tetraCl—$C_6H$ | 2,4-Cl-3-Me-5-CN-1H-pyrrol-1-yl |
| 70 | 2-CN-5-F—$C_6H_3$ | 2,3,4,6-tetraCl—$C_6H$ | 3,4-Cl-2-Me-5-CN-1H-pyrrol-1-yl |
| 71 | 2-CN-6-F—$C_6H_3$ | | |

TABLE 4

| R¹ | R² | R⁶ | X | | Column 1 | Column 2 |
|---|---|---|---|---|---|---|
| H | H | t-Bu | O | Z = | $C_6H_5$ | 2,5-diF—$C_6H_3$ |
| H | H | t-Bu | O | Z = | 2-F—$C_6H_4$ | 2,5-diCl—$C_6H_3$ |
| H | H | t-Bu | O | Z = | 2-Cl—$C_6H_4$ | 2-F-5-Cl—$C_6H_3$ |
| H | H | t-Bu | O | Z = | 2-CN—$C_6H_4$ | 2-Cl-5-F—$C_6H_3$ |
| H | H | t-Bu | O | Z = | 3-Cl—$C_6H_4$ | 2-CN-5-F—$C_6H_3$ |
| H | H | t-Bu | O | Z = | 3-F—$C_6H_4$ | 2-CN-5-Cl—$C_6H_3$ |
| H | H | t-Bu | $CH_2$ | Z = | $C_6H_5$ | 2,5-diF—$C_6H_3$ |
| H | H | t-Bu | $CH_2$ | Z = | 2-F—$C_6H_4$ | 2,5-diCl—$C_6H_3$ |
| H | H | t-Bu | $CH_2$ | Z = | 2-Cl—$C_6H_4$ | 2-F-5-Cl—$C_6H_3$ |
| H | H | t-Bu | $CH_2$ | Z = | 2-CN—$C_6H_4$ | 2-Cl-5-F—$C_6H_3$ |
| H | H | t-Bu | $CH_2$ | Z = | 3-C—$C_6H_4$ | 2-CN-5-F—$C_6H_3$ |
| H | H | t-Bu | $CH_2$ | Z = | 3-F—$C_6H_4$ | 2-CN-5-Cl—$C_6H_3$ |
| H | H | t-Bu | =CH | Z = | $C_6H_5$ | 2,5-diF—$C_6H_3$ |
| H | H | t-Bu | =CH | Z = | 2-F—$C_6H_4$ | 2,5-diCl—$C_6H_3$ |
| H | H | t-Bu | =CH | Z = | 2-Cl—$C_6H_4$ | 2-F-5-Cl—$C_6H_3$ |
| H | H | t-Bu | =CH | Z = | 2-CN—$C_6H_4$ | 2-Cl-5-F—$C_6H_3$ |
| H | H | t-Bu | =CH | Z = | 3-Cl—$C_6H_4$ | 2-CN-5-F—$C_6H_3$ |
| H | H | t-Bu | =CH | Z = | 3-F—$C_6H_4$ | 2-CN-5-Cl—$C_6H_3$ |
| Me | Me | t-Bu | O | Z = | $C_6H_5$ | 2,5-diF—$C_6H_3$ |
| Me | Me | t-Bu | O | Z = | 2-F—$C_6H_4$ | 2,5-diCl—$C_6H_3$ |
| Me | Me | t-Bu | O | Z = | 2-Cl—$C_6H_4$ | 2-F-5-Cl—$C_6H_3$ |
| Me | Me | t-Bu | O | Z = | 2-CN—$C_6H_4$ | 2-Cl-5-F—$C_6H_3$ |
| Me | Me | t-Bu | O | Z = | 3-Cl—$C_6H_4$ | 2-CN-5-F—$C_6H_3$ |
| Me | Me | t-Bu | O | Z = | 3-F—$C_6H_4$ | 2-CN-5-Cl—$C_6H_3$ |
| Me | Et | t-Bu | O | Z = | $C_6H_5$ | 2,5-diF—$C_6H_3$ |
| Me | Et | t-Bu | O | Z = | 2-F—$C_6H_4$ | 2,5-diCl—$C_6H_3$ |
| Me | Et | t-Bu | O | Z = | 2-Cl—$C_6H_4$ | 2-F-5-Cl—$C_6H_3$ |
| Me | Et | t-Bu | O | Z = | 2-CN—$C_6H_4$ | 2-Cl-5-F—$C_6H_3$ |
| Me | Et | t-Bu | O | Z = | 3-Cl—$C_6H_4$ | 2-CN-5-F—$C_6H_3$ |
| Me | Et | t-Bu | O | Z = | 3-F—$C_6H_4$ | 2-CN-5-Cl—$C_6H_3$ |
| Me | H | t-Bu | CH(Me) | Z = | $C_6H_5$ | 2,5-diF—$C_6H_3$ |
| Me | H | t-Bu | CH(Me) | Z = | 2-F—$C_6H_4$ | 2,5-diCl—$C_6H_3$ |
| Me | H | t-Bu | CH(Me) | Z = | 2-Cl—$C_6H_4$ | 2-F-5-Cl—$C_6H_3$ |
| Me | H | t-Bu | CH(Me) | Z = | 2-CN—$C_6H_4$ | 2-Cl-5-F—$C_6H_3$ |
| Me | H | t-Bu | CH(Me) | Z = | 3-Cl—$C_6H_4$ | 2-CN-5-F—$C_6H_3$ |
| Me | H | t-Bu | CH(Me) | Z = | 3-F—$C_6H_4$ | 2-CN-5-Cl—$C_6H_3$ |
| Me | H | t-Bu | CH(Et) | Z = | $C_6H_5$ | 2,5-diF—$C_6H_3$ |
| Me | H | t-Bu | CH(Et) | Z = | 2-F—$C_6H_4$ | 2,5-diCl—$C_6H_3$ |
| Me | H | t-Bu | CH(Et) | Z = | 2-Cl—$C_6H_4$ | 2-F-5-Cl—$C_6H_3$ |
| Me | H | t-Bu | CH(Et) | Z = | 2-CN—$C_6H_4$ | 2-Cl-5-F—$C_6H_3$ |
| Me | H | t-Bu | CH(Et) | Z = | 3-Cl—$C_6H_4$ | 2-CN-5-F—$C_6H_3$ |
| Me | H | t-Bu | CH(Et) | Z = | 3-F—$C_6H_4$ | 2-CN-5-Cl—$C_6H_3$ |
| Me | H | t-Bu | CH(n-Pr) | Z = | $C_6H_5$ | 2,5-diF—$C_6H_3$ |
| Me | H | t-Bu | CH(n-Pr) | Z = | 2-F—$C_6H_4$ | 2,5-diCl—$C_6H_3$ |
| Me | H | t-Bu | CH(n-Pr) | Z = | 2-Cl—$C_6H_4$ | 2-F-5-Cl—$C_6H_3$ |
| Me | H | t-Bu | CH(n-Pr) | Z = | 2-CN—$C_6H_4$ | 2-Cl-5-F—$C_6H_3$ |
| Me | H | t-Bu | CH(n-Pr) | Z = | 3-Cl—$C_6H_4$ | 2-CN-5-F—$C_6H_3$ |
| Me | H | t-Bu | CH(n-Pr) | Z = | 3-F—$C_6H_4$ | 2-CN-5-Cl—$C_6H_3$ |
| Me | H | t-Bu | =C(Me) | Z = | $C_6H_5$ | 2,5-diF—$C_6H_3$ |
| Me | H | t-Bu | =C(Me) | Z = | 2-F—$C_6H_4$ | 2,5-diCl—$C_6H_3$ |
| Me | H | t-Bu | =C(Me) | Z = | 2-Cl—$C_6H_4$ | 2-F-5-Cl—$C_6H_3$ |
| Me | H | t-Bu | =C(Me) | Z = | 2-CN—$C_6H_4$ | 2-Cl-5-F—$C_6H_3$ |
| Me | H | t-Bu | =C(Me) | Z = | 3-Cl—$C_6H_4$ | 2-CN-5-F—$C_6H_3$ |
| Me | H | t-Bu | =C(Me) | Z = | 3-F—$C_6H_4$ | 2-CN-5-Cl—$C_6H_3$ |
| Me | H | t-Bu | =C(Et) | Z = | $C_6H_5$ | 2,5-diF—$C_6H_3$ |
| Me | H | t-Bu | =C(Et) | Z = | 2-F—$C_6H_4$ | 2,5-diCl—$C_6H_3$ |
| Me | H | t-Bu | =C(Et) | Z = | 2-Cl—$C_6H_4$ | 2-F-5-Cl—$C_6H_3$ |
| Me | H | t-Bu | =C(Et) | Z = | 2-CN—$C_6H_4$ | 2-Cl-5-F—$C_6H_3$ |
| Me | H | t-Bu | =C(Et) | Z = | 3-Cl—$C_6H_4$ | 2-CN-5-F—$C_6H_3$ |
| Me | H | t-Bu | =C(Et) | Z = | 3-F—$C_6H_4$ | 2-CN-5-Cl—$C_6H_3$ |
| H | H | t-Bu | $CH_2$ | Z = | 2-thienyl | 3,5-diF-2-thienyl |
| H | H | t-Bu | $CH_2$ | Z = | 3-F-2-thienyl | 3,5-diCl-2-thienyl |
| H | H | t-Bu | $CH_2$ | Z = | 3-Cl-2-thienyl | 3-Cl-5-F-2-thienyl |
| H | H | t-Bu | $CH_2$ | Z = | 3-CN-2-thienyl | 3-F-5-Cl-2-thienyl |
| H | H | t-Bu | $CH_2$ | Z = | 5-F-2-thienyl | 3-CN-5-F-2-thienyl |
| H | H | t-Bu | $CH_2$ | Z = | 5-Cl-2-thienyl | 3-CN-5-Cl-2-thienyl |
| H | H | t-Bu | =CH | Z = | 2-thienyl | 3,5-diF-2-thienyl |
| H | H | t-Bu | =CH | Z = | 3-F-2-thienyl | 3,5-diCl-2-thienyl |
| H | H | t-Bu | =CH | Z = | 3-Cl-2-thienyl | 3-Cl-5-F-2-thienyl |

TABLE 4-continued

| R¹ | R² | R⁶ | X | | Column 1 | Column 2 |
|---|---|---|---|---|---|---|
| H | H | t-Bu | =CH | Z = | 3-CN-2-thienyl | 3-F-5-Cl-2-thienyl |
| H | H | t-Bu | =CH | Z = | 5-F-2-thienyl | 3-CN-5-F-2-thienyl |
| H | H | t-Bu | =CH | Z = | 5-Cl-2-thienyl | 3-CN-5-Cl-2-thienyl |
| H | H | t-Bu | CH₂ | Z = | 3-thienyl | 2,5-diF-3-thienyl |
| H | H | t-Bu | CH₂ | Z = | 2-F-3-thienyl | 2,5-diCl-3-thienyl |
| H | H | t-Bu | CH₂ | Z = | 2-Cl-3-thienyl | 2-Cl-5-F-3-thienyl |
| H | H | t-Bu | CH₂ | Z = | 2-CN-3-thienyl | 2-F-5-Cl-3-thienyl |
| H | H | t-Bu | CH₂ | Z = | 5-F-3-thienyl | 2-CN-5-F-3-thienyl |
| H | H | t-Bu | CH₂ | Z = | 5-Cl-3-thienyl | 2-CN-5-Cl-3-thienyl |
| H | H | t-Bu | =CH | Z = | 3-thienyl | 2,5-diF-3-thienyl |
| H | H | t-Bu | =CH | Z = | 2-F-3-thienyl | 2,5-diCl-3-thienyl |
| H | H | t-Bu | =CH | Z = | 2-Cl-3-thienyl | 2-Cl-5-F-3-thienyl |
| H | H | t-Bu | =CH | Z = | 2-CN-3-thienyl | 2-F-5-Cl-3-thienyl |
| H | H | t-Bu | =CH | Z = | 5-F-3-thienyl | 2-CN-5-F-3-thienyl |
| H | H | t-Bu | =CH | Z = | 5-Cl-3-thienyl | 2-CN-5-Cl-3-thienyl |
| H | H | t-Bu | CH₂ | Z = | 1H-pyrrol-1-yl | 2,5-diF-1H-pyrrol-1-yl |
| H | H | t-Bu | CH₂ | Z = | 2-F-1H-pyrrol-1-yl | 2,5-diCl-1H-pyrrol-1-yl |
| H | H | t-Bu | CH₂ | Z = | 2-Cl-1H-pyrrol-1-yl | 2-Cl-5-F-1H-pyrrol-1-yl |
| H | H | t-Bu | CH₂ | Z = | 2-CN-1H-pyrrol-1-yl | 2-F-5-Cl-1H-pyrrol-1-yl |
| H | H | t-Bu | CH₂ | Z = | 5-F-1H-pyrrol-1-yl | 2-CN-5-Cl-1H-pyrrol-1-yl |
| H | H | t-Bu | CH₂ | Z = | 5-Cl-1H-pyrrol-1-yl | 2-CN-5-F-1H-pyrrol-1-yl |
| H | H | t-Bu | =CH | Z = | 1H-pyrrol-1-yl | 2,5-diF-1H-pyrrol-1-yl |
| H | H | t-Bu | =CH | Z = | 2-F-1H-pyrrol-1-yl | 2,5-diCl-1H-pyrrol-1-yl |
| H | H | t-Bu | =CH | Z = | 2-Cl-1H-pyrrol-1-yl | 2-Cl-5-F-1H-pyrrol-1-yl |
| H | H | t-Bu | =CH | Z = | 2-CN-1H-pyrrol-1-yl | 2-F-5-Cl-1H-pyrrol-1-yl |
| H | H | t-Bu | =CH | Z = | 5-F-1H-pyrrol-1-yl | 2-CN-5-Cl-1H-pyrrol-1-yl |
| H | H | t-Bu | =CH | Z = | 5-Cl-1H-pyrrol-1-yl | 2-CN-5-F-1H-pyrrol-l-yl |
| H | H | t-Bu | O | Z = | 1H-pyrrol-1-yl | 2,5-diF-1H-pyrrol-1-yl |
| H | H | t-Bu | O | Z = | 2-F-1H-pyrrol-1-yl | 2,5-diCl-1H-pyrrol-1-yl |
| H | H | t-Bu | O | Z = | 2-Cl-1H-pyrrol-1-yl | 2-Cl-5-F-1H-pyrrol-1-yl |
| H | H | t-Bu | O | Z = | 2-CN-1H-pyrrol-1-yl | 2-F-5-Cl-1H-pyrrol-1-yl |
| H | H | t-Bu | O | Z = | 5-F-1H-pyrrol-1-yl | 2-CN-5-Cl-1H-pyrrol-1-yl |
| H | H | t-Bu | O | Z = | 5-Cl-1H-pyrrol-1-yl | 2-CN-5-F-1H-pyrrol-1-yl |
| Me | H | CH(Me)C(Me)₃ | O | Z = | C₆H₅ | 2,5-diF—C₆H₃ |
| Me | H | CH(Me)C(Me)₃ | O | Z = | 2-F—C₆H₄ | 2,5-diCl—C₆H₃ |
| Me | H | CH(Me)C(Me)₃ | O | Z = | 2-Cl—C₆H₄ | 2-F-5-Cl—C₆H₃ |
| Me | H | CH(Me)C(Me)₃ | O | Z = | 2-CN—C₆H₄ | 2-Cl-5-F—C₆H₃ |
| Me | H | CH(Me)C(Me)₃ | O | Z = | 3-Cl—C₆H₄ | 2-CN-5-F—C₆H₃ |
| Me | H | CH(Me)C(Me)₃ | O | Z = | 3-F—C₆H₄ | 2-CN-5-Cl—C₆H₃ |
| Me | H | CH(Me)C(Me)₃ | =CH | Z = | C₆H₅ | 2,5-diF—C₆H₃ |
| Me | H | CH(Me)C(Me)₃ | =CH | Z = | 2-F—C₆H₄ | 2,5-diCl—C₆H₃ |
| Me | H | CH(Me)C(Me)₃ | =CH | Z = | 2-Cl—C₆H₄ | 2-F-5-Cl—C₆H₃ |
| Me | H | CH(Me)C(Me)₃ | =CH | Z = | 2-CN—C₆H₄ | 2-Cl-5-F—C₆H₃ |
| Me | H | CH(Me)C(Me)₃ | =CH | Z = | 3-Cl—C₆H₄ | 2-CN-5-F—C₆H₃ |
| Me | H | CH(Me)C(Me)₃ | =CH | Z = | 3-F—C₆H₄ | 2-CN-5-Cl—C₆H₃ |
| Me | H | CH(Me)C(Me)₃ | CH₂ | Z = | C₆H₅ | 2,5-diF—C₆H₃ |
| Me | H | CH(Me)C(Me)₃ | CH₂ | Z = | 2-F—C₆H₄ | 2,5-diCl—C₆H₃ |
| Me | H | CH(Me)C(Me)₃ | CH₂ | Z = | 2-Cl—C₆H₄ | 2-F-5-Cl—C₆H₃ |
| Me | H | CH(Me)C(Me)₃ | CH₂ | Z = | 2-CN—C₆H₄ | 2-Cl-5-F—C₆H₃ |
| Me | H | CH(Me)C(Me)₃ | CH₂ | Z = | 3-Cl—C₆H₄ | 2-CN-5-F—C₆H₃ |
| Me | H | CH(Me)C(Me)₃ | CH₂ | Z = | 3-F—C₆H₄ | 2-CN-5-Cl—C₆H₃ |
| H | H | CH(Me)C(Me)₃ | O | Z = | C₆H₅ | 2,5-diF—C₆H₃ |
| H | H | CH(Me)C(Me)₃ | O | Z = | 2-F—C₆H₄ | 2,5-diCl—C₆H₃ |
| H | H | CH(Me)C(Me)₃ | O | Z = | 2-Cl—C₆H₄ | 2-F-5-Cl—C₆H₃ |
| H | H | CH(Me)C(Me)₃ | O | Z = | 2-CN—C₆H₄ | 2-Cl-5-F—C₆H₃ |
| H | H | CH(Me)C(Me)₃ | O | Z = | 3-Cl—C₆H₄ | 2-CN-5-F—C₆H₃ |
| H | H | CH(Me)C(Me)₃ | O | Z = | 3-F—C₆H₄ | 2-CN-5-Cl—C₆H₃ |
| H | H | CH(Me)C(Me)₃ | =CH | Z = | C₆H₅ | 2,5-diF—C₆H₃ |
| H | H | CH(Me)C(Me)₃ | =CH | Z = | 2-F—C₆H₄ | 2,5-diCl—C₆H₃ |
| H | H | CH(Me)C(Me)₃ | =CH | Z = | 2-Cl—C₆H₄ | 2-F-5-Cl—C₆H₃ |
| H | H | CH(Me)C(Me)₃ | =CH | Z = | 2-CN—C₆H₄ | 2-Cl-5-F—C₆H₃ |
| H | H | CH(Me)C(Me)₃ | =CH | Z = | 3-Cl—C₆H₄ | 2-CN-5-F—C₆H₃ |
| H | H | CH(Me)C(Me)₃ | =CH | Z = | 3-F—C₆H₄ | 2-CN-5-Cl—C₆H₃ |
| H | H | CH(Me)C(Me)₃ | CH₂ | Z = | C₆H₅ | 2,5-diF—C₆H₃ |
| H | H | CH(Me)C(Me)₃ | CH₂ | Z = | 2-F—C₆H₄ | 2,5-diCl—C₆H₃ |
| H | H | CH(Me)C(Me)₃ | CH₂ | Z = | 2-Cl—C₆H₄ | 2-F-5-Cl—C₆H₃ |
| H | H | CH(Me)C(Me)₃ | CH₂ | Z = | 2-CN—C₆H₄ | 2-Cl-5-F—C₆H₃ |
| H | H | CH(Me)C(Me)₃ | CH₂ | Z = | 3-Cl—C₆H₄ | 2-CN-5-F—C₆H₃ |
| H | H | CH(Me)C(Me)₃ | CH₂ | Z = | 3-F—C₆H₄ | 2-CN-5-Cl—C₆H₃ |

TABLE 4-continued

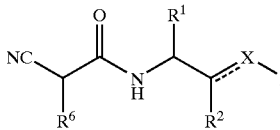

| R¹ | R² | R⁶ | X | | Column 1 | Column 2 |
|---|---|---|---|---|---|---|
| Me | H | CH(Me)C(Me)₃ | CH₂ | Z = | 1H-pyrrol-1-yl | 2,5-diF-1H-pyrrol-1-yl |
| Me | H | CH(Me)C(Me)₃ | CH₂ | Z = | 2-F-1H-pyrrol-1-yl | 2,5-diCl-1H-pyrrol-1-yl |
| Me | H | CH(Me)C(Me)₃ | CH₂ | Z = | 2-Cl-1H-pyrrol-1-yl | 2-Cl-5-F-1H-pyrrol-1-yl |
| Me | H | CH(Me)C(Me)₃ | CH₂ | Z = | 2-CN-1H-pyrrol-1-yl | 2-F-5-Cl-1H-pyrrol-1-yl |
| Me | H | CH(Me)C(Me)₃ | CH₂ | Z = | 5-F-1H-pyrrol-1-yl | 2-CN-5-Cl-1H-pyrrol-1-yl |
| Me | H | CH(Me)C(Me)₃ | CH₂ | Z = | 5-Cl-1H-pyrrol-1-yl | 2-CN-5-F-1H-pyrrol-1-yl |
| Me | Ph | CH₂CH₃ | O | Z = | 2-CN—C₆H₄ | 2-CN-5-F—C₆H₃ |
| Me | Ph | CH₂CH₃ | O | Z = | 2,5-diF—C₆H₃ | 2-Cl-5-F—C₆H₃ |
| Me | Ph | CH(Me)₂ | O | Z = | 2-CN—C₆H₄ | 2-CN-5-F—C₆H₃ |
| Me | Ph | C(Me)₃ | O | Z = | 2-CN—C₆H₄ | 2-CN-5-F—C₆H₃ |
| Me | Ph | CH₂CH=CH₂ | O | Z = | 2-CN—C₆H₄ | 2-CN-5-Cl-1H-pyrrol-1-yl |
| Me | Ph | CH₂CH=CH₂ | O | Z = | 2,5-diF—C₆H₃ | 2-CN-5-F-1H-pyrrol-1-yl |
| Me | H | CH(Me)C(Me)₃ | O | Z = | 1H-pyrrol-1-yl | 2-Cl-5-F—C₆H₃ |
| Me | H | CH(Me)C(Me)₃ | O | Z = | 2-F-1H-pyrrol-1-yl | 2,5-diCl-1H-pyrrol-1-yl |
| Me | H | CH(Me)C(Me)₃ | O | Z = | 2-Cl-1H-pyrrol-1-yl | 2-Cl-5-F-1H-pyrrol-1-yl |
| Me | H | CH(Me)C(Me)₃ | O | Z = | 2-CN-1H-pyrrol-1-yl | 2-F-5-Cl-1H-pyrrol-1-yl |
| Me | H | CH(Me)C(Me)₃ | O | Z = | 5-F-1H-pyrrol-1-yl | 2-CN-5-Cl-1H-pyrrol-1-yl |
| Me | H | CH(Me)C(Me)₃ | O | Z = | 5-Cl-1H-pyrrol-1-yl | 2-CN-5-F-1H-pyrrol-1-yl |
| H | H | CH(Me)C(Me)₃ | CH₂ | Z = | 1H-pyrrol-1-yl | 2,5-diF-1H-pyrrol-1-yl |
| H | H | CH(Me)C(Me)₃ | CH₂ | Z = | 2-F-1H-pyrrol-1-yl | 2,5-diCl-1H-pyrrol-1-yl |
| H | H | CH(Me)C(Me)₃ | CH₂ | Z = | 2-Cl-1H-pyrrol-1-yl | 2-Cl-5-F-1H-pyrrol-1-yl |
| H | H | CH(Me)C(Me)₃ | CH₂ | Z = | 2-CN-1H-pyrrol-1-yl | 2-F-5-Cl-1H-pyrrol-1-yl |
| H | H | CH(Me)C(Me)₃ | CH₂ | Z = | 5-F-1H-pyrrol-1-yl | 2-CN-5-Cl-1H-pyrrol-1-yl |
| H | H | CH(Me)C(Me)₃ | CH₂ | Z = | 5-Cl-1H-pyrrol-1-yl | 2-CN-5-F-1H-pyrrol-1-yl |
| Me | Ph | CH₂CH₃ | O | Z = | 2-F-5-Cl—C₆H₃ | 2-CN-5-Cl—C₆H₃ |
| Me | Ph | CH₂CH₃ | O | Z = | 2-F-5-Me—C₆H₃ | 2-CN-5-Me—C₆H₃ |
| Me | Ph | CH₂CH₂F | O | Z = | 2,5-diF—C₆H₃ | 2-CN-5-F—C₆H₃ |
| Me | Ph | CH₂CH₂Cl | O | Z = | 2,5-diF—C₆H₃ | 2-CN-5-F—C₆H₃ |
| Me | Ph | CH₂C≡CH | O | Z = | 2,5-diF—C₆H₃ | 2-CN-5-F—C₆H₃ |
| Me | Ph | CH₂C(F)=CH₂ | O | Z = | 2,5-diF—C₆H₃ | 2-CN-5-F—C₆H₃ |
| H | H | CH(Me)C(Me)₃ | O | Z = | 1H-pyrrol-1-yl | 2,5-diF-1H-pyrrol-1-yl |
| H | H | CH(Me)C(Me)₃ | O | Z = | 2-F-1H-pyrrol-1-yl | 2,5-diCl-1H-pyrrol-1-yl |
| H | H | CH(Me)C(Me)₃ | O | Z = | 2-Cl-1H-pyrrol-1-yl | 2-Cl-5-F-1H-pyrrol-1-yl |
| H | H | CH(Me)C(Me)₃ | O | Z = | 2-CN-1H-pyrrol-1-yl | 2-F-5-Cl-1H-pyrrol-1-yl |
| H | H | CH(Me)C(Me)₃ | O | Z = | 5-F-1H-pyrrol-1-yl | 2-CN-5-Cl-1H-pyrrol-1-yl |
| H | H | CH(Me)C(Me)₃ | O | Z = | 5-Cl-1H-pyrrol-1-yl | 2-CN-5-F-1H-pyrrol-1-yl |
| Me | H | i-Pr | O | Z = | 2,5-diF—C₆H₃ | 2-Me-5-Cl—C₆H₃ |
| Me | H | i-Pr | O | Z = | 2-Cl-5-Me—C₆H₃ | 2,5-diCl—C₆H₃ |
| Me | H | i-Pr | O | Z = | 3-F—C₆H₄ | 2-CN-5-Cl—C₆H₃ |
| Me | H | C(Me)₂CH=CH₂ | O | Z = | 2-OCH₂F-5-F—C₆H₃ | 2-F-5-Cl—C₆H₃ |
| Me | H | C(Me)₂CH=CH₂ | O | Z = | 2-Cl-5-F—C₆H₃ | 2-F-5-Br—C₆H₃ |
| Me | H | C(Me)₂CH=CH₂ | O | Z = | 2-Br-5-F—C₆H₃ | 2-F-5-Me—C₆H₃ |
| Me | H | C(Me)₂CH=CH₂ | O | Z = | 2,5-diF—C₆H₃ | 2-Me-5-Cl—C₆H₃ |
| Me | H | C(Me)₂CH=CH₂ | O | Z = | 2-Cl-5-Me—C₆H₃ | 2,5-diCl—C₆H₃ |
| Me | H | C(Me)₂CH=CH₂ | O | Z = | 3-F—C₆H₄ | 2-CN-5-Cl—C₆H₃ |
| Me | H | CH(Me)CH(Me)₂ | O | Z = | 2,5-diF—C₆H₃ | 2-Me-5-Cl—C₆H₃ |
| Me | H | CH(Me)CH(Me)₂ | O | Z = | 2-Cl-5-Me—C₆H₃ | 2,5-diCl—C₆H₃ |
| Me | H | CH(Me)CH(Me)₂ | O | Z = | 3-F—C₆H₄ | 2-CN-5-Cl—C₆H₃ |
| Me | H | c-Pr | O | Z = | 2,5-diF—C₆H₃ | 2-Me-5-Cl—C₆H₃ |
| Me | H | c-Pr | O | Z = | 2-Cl-5-Me—C₆H₃ | 2,5-diCl—C₆H₃ |
| Me | H | c-Pr | O | Z = | 3-F—C₆H₄ | 2-CN-5-Cl—C₆H₃ |
| Me | H | CH(Me)-c-Pr | O | Z = | 2,5-diF—C₆H₃ | 2-Me-5-Cl—C₆H₃ |
| Me | H | CH(Me)-c-Pr | O | Z = | 2-Cl-5-Me—C₆H₃ | 2,5-diCl—C₆H₃ |
| Me | H | CH(Me)-c-Pr | O | Z = | 3-F—C₆H₄ | 2-CN-5-Cl—C₆H₃ |
| Me | H | C(Me)₂CF=CH₂ | O | Z = | 2-OCH₂F-5-F—C₆H₃ | 2-F-5-Cl—C₆H₃ |
| Me | H | C(Me)₂CF=CH₂ | O | Z = | 2-Cl-5-F—C₆H₃ | 2-F-5-Br—C₆H₃ |
| Me | H | C(Me)₂CF=CH₂ | O | Z = | 2-Br-5-F—C₆H₃ | 2-F-5-Me—C₆H₃ |
| Me | H | C(Me)₂CF=CH₂ | O | Z = | 2,5-diF—C₆H₃ | 2-Me-5-Cl—C₆H₃ |
| Me | H | C(Me)₂CF=CH₂ | O | Z = | 2-Cl-5-Me—C₆H₃ | 2,5-diCl—C₆H₃ |
| Me | H | C(Me)₂CF=CH₂ | O | Z = | 3-F—C₆H₄ | 2-CN-5-Cl—C₆H₃ |
| Me | H | C(Me)₂CH=CHF | O | Z = | 2-OCH₂F-5-F—C₆H₃ | 2-F-5-Cl—C₆H₃ |
| Me | H | C(Me)₂CH=CHF | O | Z = | 2-Cl-5-F—C₆H₃ | 2-F-5-Br—C₆H₃ |
| Me | H | C(Me)₂CH=CHF | O | Z = | 2-Br-5-F—C₆H₃ | 2-F-5-Me—C₆H₃ |
| Me | H | C(Me)₂CH=CHF | O | Z = | 2,5-diF—C₆H₃ | 2-Me-5-Cl—C₆H₃ |
| Me | H | C(Me)₂CH=CHF | O | Z = | 2-Cl-5-Me—C₆H₃ | 2,5-diCl—C₆H₃ |
| Me | H | C(Me)₂CH=CHF | O | Z = | 3-F—C₆H₄ | 2-CN-5-Cl—C₆H₃ |
| Me | H | C(Me)(CH₂F)CH=CH₂ | O | Z = | 2-OCH₂F-5-F—C₆H₃ | 2-F-5-Cl—C₆H₃ |
| Me | H | C(Me)(CH₂F)CH=CH₂ | O | Z = | 2-Cl-5-F—C₆H₃ | 2-F-5-Br—C₆H₃ |
| Me | H | C(Me)(CH₂F)CH=CH₂ | O | Z = | 2-Br-5-F—C₆H₃ | 2-F-5-Me—C₆H₃ |

TABLE 4-continued

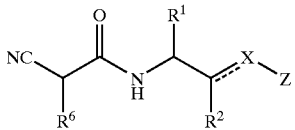

| R¹ | R² | R⁶ | X | Column 1 | Column 2 |
|---|---|---|---|---|---|
| Me | H | C(Me)(CH₂F)CH=CH₂ | O | Z = 2,5-diF—C₆H₃ | 2-Me-5-Cl—C₆H₃ |
| Me | H | C(Me)(CH₂F)CH=CH₂ | O | Z = 2-Cl-5-Me—C₆H₃ | 2,5-diCl—C₆H₃ |
| Me | H | C(Me)(CH₂F)CH=CH₂ | O | Z = 3-F—C₆H₄ | 2-CN-5-Cl—C₆H₃ |
| Me | H | C(Me)(CH₂F)CF=CH₂ | O | Z = 2-OCH₂F-5-F—C₆H₃ | 2-F-5-Cl—C₆H₃ |
| Me | H | C(Me)(CH₂F)CF=CH₂ | O | Z = 2-Cl-5-F—C₆H₃ | 2-F-5-Br—C₆H₃ |
| Me | H | C(Me)(CH₂F)CF=CH₂ | O | Z = 2-Br-5-F—C₆H₃ | 2-F-5-Me—C₆H₃ |
| Me | H | C(Me)(CH₂F)CF=CH₂ | O | Z = 2,5-diF—C₆H₃ | 2-Me-5-Cl—C₆H₃ |
| Me | H | C(Me)(CH₂F)CF=CH₂ | O | Z = 2-Cl-5-Me—C₆H₃ | 2,5-diCl—C₆H₃ |
| Me | H | C(Me)(CH₂F)CF=CH₂ | O | Z = 3-F—C₆H₄ | 2-CN-5-Cl—C₆H₃ |
| Me | H | C(CH₂F)₂CH=CH₂ | O | Z = 2-OCH₂F-5-F—C₆H₃ | 2-F-5-Cl—C₆H₃ |
| Me | H | C(CH₂F)₂CH=CH₂ | O | Z = 2-Cl-5-F—C₆H₃ | 2-F-5-Br—C₆H₃ |
| Me | H | C(CH₂F)₂CH=CH₂ | O | Z = 2-Br-5-F—C₆H₃ | 2-F-5-Me—C₆H₃ |
| Me | H | C(CH₂F)₂CH=CH₂ | O | Z = 2,5-diF—C₆H₃ | 2-Me-5-Cl—C₆H₃ |
| Me | H | C(CH₂F)₂CH=CH₂ | O | Z = 2-Cl-5-Me—C₆H₃ | 2,5-diCl—C₆H₃ |
| Me | H | C(CH₂F)₂CH=CH₂ | O | Z = 3-F—C₆H₄ | 2-CN-5-Cl—C₆H₃ |
| Me | H | C(Me)₂CCl=CH₂ | O | Z = 2-OCH₂F-5-F—C₆H₃ | 2-F-5-Cl—C₆H₃ |
| Me | H | C(Me)₂CCl=CH₂ | O | Z = 2-Cl-5-F—C₆H₃ | 2-F-5-Br—C₆H₃ |
| Me | H | C(Me)₂CCl=CH₂ | O | Z = 2-Br-5-F—C₆H₃ | 2-F-5-Me—C₆H₃ |
| Me | H | C(Me)₂CCl=CH₂ | O | Z = 2,5-diF—C₆H₃ | 2-Me-5-Cl—C₆H₃ |
| Me | H | C(Me)₂CCl=CH₂ | O | Z = 2-Cl-5-Me—C₆H₃ | 2,5-diCl—C₆H₃ |
| Me | H | C(Me)₂CCl=CH₂ | O | Z = 3-F—C₆H₄ | 2-CN-5-Cl—C₆H₃ |
| Me | H | C(CH₂Cl)₂CH=CH₂ | O | Z = 2-OCH₂F-5-F—C₆H₃ | 2-F-5-Cl—C₆H₃ |
| Me | H | C(CH₂Cl)₂CH=CH₂ | O | Z = 2-Cl-5-F—C₆H₃ | 2-F-5-Br—C₆H₃ |
| Me | H | C(CH₂Cl)₂CH=CH₂ | O | Z = 2-Br-5-F—C₆H₃ | 2-F-5-Me—C₆H₃ |
| Me | H | C(CH₂Cl)₂CH=CH₂ | O | Z = 2,5-diF—C₆H₃ | 2-Me-5-Cl—C₆H₃ |
| Me | H | C(CH₂Cl)₂CH=CH₂ | O | Z = 2-Cl-5-Me—C₆H₃ | 2,5-diCl—C₆H₃ |
| Me | H | C(CH₂Cl)₂CH=CH₂ | O | Z = 3-F—C₆H₄ | 2-CN-5-Cl—C₆H₃ |
| Me | H | C(Me)₂-c-Pr | O | Z = 2-OCH₂F-5-F—C₆H₃ | 2-F-5-Cl—C₆H₃ |
| Me | H | C(Me)₂-c-Pr | O | Z = 2-Cl-5-F—C₆H₃ | 2-F-5-Br—C₆H₃ |
| Me | H | C(Me)₂-c-Pr | O | Z = 2-Br-5-F—C₆H₃ | 2-F-5-Me—C₆H₃ |
| Me | H | C(Me)₂-c-Pr | O | Z = 2,5-diF—C₆H₃ | 2-Me-5-Cl—C₆H₃ |
| Me | H | C(Me)₂-c-Pr | O | Z = 2-Cl-5-Me—C₆H₃ | 2,5-diCl—C₆H₃ |
| Me | H | C(Me)₂-c-Pr | O | Z = 3-F—C₆H₄ | 2-CN-5-Cl—C₆H₃ |
| Me | H | C(Me)₂CF=CF₂ | O | Z = 2-OCH₂F-5-F—C₆H₃ | 2-F-5-Cl—C₆H₃ |
| Me | H | C(Me)₂CF=CF₂ | O | Z = 2-Cl-5-F—C₆H₃ | 2-F-5-Br—C₆H₃ |
| Me | H | C(Me)₂CF=CF₂ | O | Z = 2-Br-5-F—C₆H₃ | 2-F-5-Me—C₆H₃ |
| Me | H | C(Me)₂CF=CF₂ | O | Z = 2,5-diF—C₆H₃ | 2-Me-5-Cl—C₆H₃ |
| Me | H | C(Me)₂CF=CF₂ | O | Z = 2-Cl-5-Me—C₆H₃ | 2,5-diCl—C₆H₃ |
| Me | H | C(Me)₂CF=CF₂ | O | Z = 3-F—C₆H₄ | 2-CN-5-Cl—C₆H₃ |
| Me | H | C(CH₃)(C≡CH)CH=CH₂ | O | Z = 2,5-diF—C₆H₃ | 2-F-5-Cl—C₆H₃ |
| Me | H | C(CH₃)(C≡CH)CH=CH₂ | O | Z = 2-Cl-5-F—C₆H₃ | 2-CN-5-F—C₆H₃ |
| Me | H | C(CH₃)(C≡CH)CH=CH₂ | O | Z = 2,5-diCl—C₆H₃ | 2-CN-5-Cl—C₆H₃ |
| Me | H | C(CH=CH₂)₂CH₃ | O | Z = 2,5-diF—C₆H₃ | 2-F-5-Cl—C₆H₃ |
| Me | H | C(CH=CH₂)₂CH₃ | O | Z = 2-Cl-5-F—C₆H₃ | 2-CN-5-F—C₆H₃ |
| Me | H | C(CH=CH₂)₂CH₃ | O | Z = 2,5-diCl—C₆H₃ | 2-CN-5-Cl—C₆H₃ |
| Me | H | C(CH₃)₂CH=CHC≡CH | O | Z = 2,5-diF—C₆H₃ | 2-F-5-Cl—C₆H₃ |
| Me | H | C(CH₃)₂CH=CHC≡CH | O | Z = 2-Cl-5-F—C₆H₃ | 2-CN-5-F—C₆H₃ |
| Me | H | C(CH₃)₂CH=CHC≡CH | O | Z = 2,5-diCl—C₆H₃ | 2-CN-5-Cl—C₆H₃ |

TABLE 5

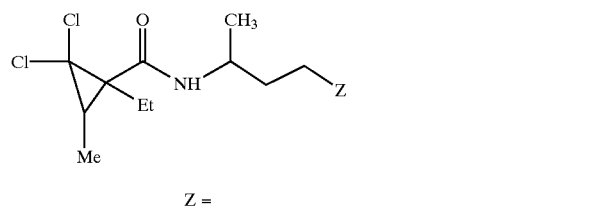

Z =

| | Column 1 | Column 2 | Column 3 |
|---|---|---|---|
| 1 | C₆H₅ | 2-F-5-Me—C₆H₃ | 2-I-1H-pyrrol-1-yl |
| 2 | 2-F—C₆H₄ | 2-F-6-Me—C₆H₃ | 2-Cl-1H-pyrrol-1-yl |
| 3 | 3-F—C₆H₄ | 3-F-6-Me—C₆H₃ | 3-Cl-1H-pyrrol-1-yl |
| 4 | 4-F—C₆H₄ | 2,3,4-triF—C₆H₂ | 2-CN-1H-pyrrol-1-yl |

TABLE 5-continued

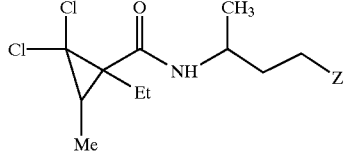

Z =

| | Column 1 | Column 2 | Column 3 |
|---|---|---|---|
| 5 | 2-Cl—C$_6$H$_4$ | 2,3,5-triF—C$_6$H$_2$ | 2-Br-1H-pyrrol-1-yl |
| 6 | 3-Cl—C$_6$H$_4$ | 2,3,6-triF—C$_6$H$_2$ | 2-n-Pr-1H-pyrrol-1-yl |
| 7 | 4-Cl—C$_6$H$_4$ | 2,3-diF-5-Cl—C$_6$H$_2$ | 2-i-Pr-1H-pyrrol-1-yl |
| 8 | 2-Br—C$_6$H$_4$ | 2,6-diF-3-Cl—C$_6$H$_2$ | 2-n-Bu-1H-pyrrol-1-yl |
| 9 | 3-Br—C$_6$H$_4$ | 2,5-diCl-3-F—C$_6$H$_2$ | 2-CH$_2$CN-1H-pyrrol-1-yl |
| 10 | 4-Br—C$_6$H$_4$ | 2,5-diCl-6-F—C$_6$H$_2$ | 2-t-Bu-1H-pyrrol-1-yl |
| 11 | 2-I-C$_6$H$_4$ | 2,3-diF-5-Me—C$_6$H$_2$ | 2-CN-5-F-3-thienyl |
| 12 | 3-I-C$_6$H$_4$ | 2,5-diF-3-Me—C$_6$H$_2$ | 2-Me-4-CN-3-thienyl |
| 13 | 4-I-C$_6$H$_4$ | 2,5-diF-6-Me—C$_6$H$_2$ | 1H-pyrrol-1-yl |
| 14 | 2-Me—C$_6$H$_4$ | 2-CN-3,5-diMe—C$_6$H$_2$ | 2-F-1H-pyrrol-1-yl |
| 15 | 3-Me—C$_6$H$_4$ | 2-CN-3,5-diCl—C$_6$H$_2$ | 5-F-1H-pyrrol-1-yl |
| 16 | 4-Me—C$_6$H$_4$ | 2-CN-3,5-diF—C$_6$H$_2$ | 5-Et-1H-pyrrol-1-yl |
| 17 | 2-Et-C$_6$H$_4$ | 2-CN-3,6-diF—C$_6$H$_2$ | 5-Cl-1H-pyrrol-1-yl |
| 18 | 2-CN—C$_6$H$_4$ | 2-CN-5,6-diF—C$_6$H$_2$ | 2-(C≡CH)-1H-pyrrol-1-yl |
| 19 | 2-CF$_3$—C$_6$H$_4$ | 2-CN-3-F-5-Cl—C$_6$H$_2$ | 5-Br-1H-pyrrol-1-yl |
| 20 | 2-n-Pr-C$_6$H$_4$ | 2-CN-3-Me-5-Cl—C$_6$H$_2$ | 2-n-Pr-1H-pyrrol-1-yl |
| 21 | 3-n-Pr-C$_6$H$_4$ | 2-CN-3-Me-5-F—C$_6$H$_2$ | 2-i-Pr-1H-pyrrol-1-yl |
| 22 | 2-i-Pr-C$_6$H$_4$ | 2-Cl-3-F-5-Me—C$_6$H$_2$ | 2-CF$_3$-1H-pyrrol-1-yl |
| 23 | 3-i-Pr-C$_6$H$_4$ | 2-F-3-Cl-5-Me—C$_6$H$_2$ | 2,3-diCl-1H-pyrrol-1-yl |
| 24 | 2-n-Bu-C$_6$H$_4$ | 2,3,4,5-tetraF—C$_6$H | 2,4-diCl-1H-pyrrol-1-yl |
| 25 | 2-CH$_2$F—C$_6$H$_4$ | 2,3,4,6-tetraF—C$_6$H | 3,4-diCl-1H-pyrrol-1-yl |
| 26 | 3-CH$_2$F—C$_6$H$_4$ | 2,3,5,6-tetraF—C$_6$H | 2,3-diBr-1H-pyrrol-1-yl |
| 27 | 2-CH$_2$CN—C$_6$H$_4$ | 2-thienyl | 2,4-diBr-1H-pyrrol-1-yl |
| 28 | 2-CH$_2$CH$_2$F—C$_6$H$_4$ | 3-F-2-thienyl | 4-F-5-Br-1H-pyrrol-1-yl |
| 29 | 2-CH$_2$CH$_2$Cl—C$_6$H$_4$ | 4-F-2-thienyl | 2-Cl-3-Br-1H-pyrrol-1-yl |
| 30 | 2-CH$_2$CH$_2$CN—C$_6$H$_4$ | 5-Et-2-thienyl | 2-Cl-4-Br-1H-pyrrol-1-yl |
| 31 | 2-(CH=CH$_2$)—C$_6$H$_4$ | 3-Cl-2-thienyl | 3-Cl-4-Br-1H-pyrrol-1-yl |
| 32 | 2-(C≡CH)—C$_6$H$_4$ | 4-Cl-2-thienyl | 3-Cl-5-Br-1H-pyrrol-1-yl |
| 33 | 2-(C≡CMe)—C$_6$H$_4$ | 5-Cl-2-thienyl | 4-F-5-Me-1H-pyrrol-1-yl |
| 34 | 2-(t-Bu)—C$_6$H$_4$ | 3-(C≡CH)-2-thienyl | 2-Cl-3-Me-1H-pyrrol-1-yl |
| 35 | 2-[CH(F)Me]—C$_6$H$_4$ | 4-Br-2-thienyl | 2-Cl-4-Me-1H-pyrrol-1-yl |
| 36 | 2-[CH(Cl)Me]—C$_6$H$_4$ | 5-Br-2-thienyl | 2-Cl-5-Me-1H-pyrrol-1-yl |
| 37 | 2-[CH(Br)Me]—C$_6$H$_4$ | 3-[CH$_2$CH(CN)Me]-2-thienyl | 3-Cl-4-Me-1H-pyrrol-1-yl |
| 38 | 2-[CH(CN)Me]—C$_6$H$_4$ | 3-(CH=CH$_2$)-2-thienyl | 3-Cl-5-Me-1H-pyrrol-1-yl |
| 39 | 2-[CH(CN)CH$_2$Me]—C$_6$H$_4$ | 3,4-diF-2-thienyl | 4-Cl-5-Me-1H-pyrrol-1-yl |
| 40 | 2,3-diF—C$_6$H$_3$ | 3,4-diF-2-thienyl | 2-Br-3-Me-1H-pyrrol-1-yl |
| 41 | 2,4-diF—C$_6$H$_3$ | 3-F-4-Br-2-thienyl | 2-Br-4-Me-1H-pyrrol-1-yl |
| 42 | 2,5-diF—C$_6$H$_3$ | 3-F-5-Br-2-thienyl | 2-Br-5-Me-1H-pyrrol-1-yl |
| 43 | 2,6-diF—C$_6$H$_3$ | 3-Br-5-F-2-thienyl | 3-Br-4-Me-1H-pyrrol-1-yl |
| 44 | 3,4-diF—C$_6$H$_3$ | 4-Br-5-F-2-thienyl | 3-Br-5-Me-1H-pyrrol-1-yl |
| 45 | 3,5-diF—C$_6$H$_3$ | 3-F-4-Me-2-thienyl | 4-Br-5-Me-1H-pyrrol-1-yl |
| 46 | 2,3-diCl—C$_6$H$_3$ | 3-F-5-Me-2-thienyl | 2-n-Pr-3-F-1H-pyrrol-1-yl |
| 47 | 2,4-diCl—C$_6$H$_3$ | 4-F-5-Me-2-thienyl | 2-n-Pr-4-F-1H-pyrrol-1-yl |
| 48 | 2,5-diCl—C$_6$H$_3$ | 3-Cl-5-Br-2-thienyl | 2-n-Pr-5-F-1H-pyrrol-1-yl |
| 49 | 2,6-diCl—C$_6$H$_3$ | 3-Me-4-F-2-thienyl | 2-n-Pr-3-Cl-1H-pyrrol-1-yl |
| 50 | 3,4-diCl—C$_6$H$_3$ | 3-Me-5-F-2-thienyl | 2-n-Pr-4-Cl-1H-pyrrol-1-yl |
| 51 | 3,5-diCl—C$_6$H$_3$ | 3-Br-5-Cl-2-thienyl | 2-n-Pr-5-Cl-1H-pyrrol-1-yl |
| 52 | 2,5-diBr—C$_6$H$_3$ | 4-Br-5-Cl-2-thienyl | 2-n-Pr-3-Br-1H-pyrrol-1-yl |
| 53 | 2-Br-5-Cl—C$_6$H$_3$ | 3-Cl-5-Me-2-thienyl | 2-n-Pr-4-Br-1H-pyrrol-1-yl |
| 54 | 2-Br-5-Me—C$_6$H$_3$ | 3-Me-5-Cl-2-thienyl | 2-n-Pr-5-Br-1H-pyrrol-1-yl |
| 55 | 3-Br-6-Me—C$_6$H$_3$ | 3-Br-5-Me-2-thienyl | 2-CN-3-F-1H-pyrrol-1-yl |
| 56 | 2-CN-3-F—C$_6$H$_3$ | 3-Me-5-Br-2-thienyl | 2-CN-4-F-1H-pyrrol-1-yl |
| 57 | 2-CN-4-F—C$_6$H$_3$ | 4-Me-5-Br-2-thienyl | 2-CN-5-F-1H-pyrrol-1-yl |
| 58 | 2-CN-5-F—C$_6$H$_3$ | 3-n-Pr-4-F-2-thienyl | 2-CN-3-Cl-1H-pyrrol-1-yl |
| 59 | 2-CN-6-F—C$_6$H$_3$ | 3-n-Pr-5-F-2-thienyl | 2-CN-4-Cl-1H-pyrrol-1-yl |
| 60 | 2-CN-3-Cl—C$_6$H$_3$ | 3-CN-5-Cl-2-thienyl | 2-CN-5-Cl-1H-pyrrol-1-yl |
| 61 | 2-CN-5-Cl—C$_6$H$_3$ | 3-CN-5-Br-2-thienyl | 2-CN-3-Br-1H-pyrrol-1-yl |
| 62 | 2-CN-5-Br—C$_6$H$_3$ | 3-thienyl | 2-CN-4-Br-1H-pyrrol-1-yl |
| 63 | 2-CN-3-I—C$_6$H$_3$ | 2-F-3-thienyl | 2-CN-5-Br-1H-pyrrol-1-yl |
| 64 | 2-CN-3-CF$_3$—C$_6$H$_3$ | 4-F-3-thienyl | 2-CN-3-Me-1H-pyrrol-1-yl |
| 65 | 2-CN-6-CF$_3$—C$_6$H$_3$ | 5-F-3-thienyl | 2-CN-4-Me-1H-pyrrol-1-yl |
| 66 | 2-CN-3-Me—C$_6$H$_3$ | 2-Cl-3-thienyl | 2-CN-5-Me-1H-pyrrol-1-yl |
| 67 | 2-CN-4-Me—C$_6$H$_3$ | 4-Cl-3-thienyl | 2-CN-5-n-Pr-1H-pyrrol-1-yl |
| 68 | 2-CN-5-Me—C$_6$H$_3$ | 5-Cl-3-thienyl | 2,3,4-triCl-1H-pyrrol-1-yl |
| 69 | 2-CN-6-Me—C$_6$H$_3$ | 2-CN-3-thienyl | 2,3,5-triCl-1H-pyrrol-1-yl |
| 70 | 2-Br-4-F—C$_6$H$_3$ | 2-Br-3-thienyl | 2,3-diCl-4-Me-1H-pyrrol-1-yl |

TABLE 5-continued

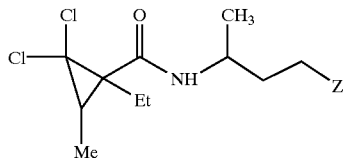

Z =

| | Column 1 | Column 2 | Column 3 |
|---|---|---|---|
| 71 | 2-Br-5-F—$C_6H_3$ | 5-Br-3-thienyl | 2,3-diCl-5-Me-1H-pyrrol-1-yl |
| 72 | 3-Br-6-F—$C_6H_3$ | 2-n-Pr-3-thienyl | 2,4-diCl-3-Me-1H-pyrrol-1-yl |
| 73 | 2-Cl-5-Me—$C_6H_3$ | 2-($CH_2CN$)-3-thienyl | 2,4-diCl-5-Me-1H-pyrrol-1-yl |
| 74 | 3-Cl-5-Me—$C_6H_3$ | 2,5-diCl-3-thienyl | 2,5-diCl-3-Me-1H-pyrrol-1-yl |
| 75 | 3-Cl-6-Me—$C_6H_3$ | 2,5-diBr-3-thienyl | 2-CN-3,4-diCl-1H-pyrrol-1-yl |
| 76 | 2-n-Pr-3-F—$C_6H_3$ | 2-F-5-Cl-3-thienyl | 2-CN-3,5-diCl-1H-pyrrol-1-yl |
| 77 | 2-n-Pr-5-F—$C_6H_3$ | 2-Cl-5-F-3-thienyl | 2-CN-4,5-diCl-1H-pyrrol-1-yl |
| 78 | 2-n-Pr-3-Cl—$C_6H_3$ | 2-F-5-Br-3-thienyl | 2-CN-3-Cl-4-Me-1H-pyrrol-1-yl |
| 79 | 2-n-Pr-5-Br—$C_6H_3$ | 2-Br-5-F-3-thienyl | 2-CN-3-Cl-5-Me-1H-pyrrol-1-yl |
| 80 | 2-n-Pr-5-Me—$C_6H_3$ | 2-Cl-5-Br-3-thienyl | 2-CN-3-Me-4-Cl-1H-pyrrol-1-yl |
| 81 | 2-Cl-3-F—$C_6H_3$ | 2-Br-5-Cl-3-thienyl | 2-CN-3-Me-5-Cl-1H-pyrrol-1-yl |
| 82 | 2-Cl-4-F—$C_6H_3$ | 2-n-Pr-5-F-3-thienyl | 2-CN-4-Me-5-Cl-1H-pyrrol-1-yl |
| 83 | 2-Cl-5-F—$C_6H_3$ | 2-CN-5-F-3-thienyl | 2-CN-4-Cl-5-Me-1H-pyrrol-1-yl |
| 84 | 2-Cl-6-F—$C_6H_3$ | 2-CN-5-Cl-3-thienyl | 2-CN-4Br-5-Me-1H-pyrrol-1-yl |
| 85 | 3-Cl-2-F—$C_6H_3$ | 2-CN-5-Br-3-thienyl | 2,3,4-triCl-5-CN-1H-pyrrol-1-yl |
| 86 | 3-Cl-6-F—$C_6H_3$ | 2-CN-5-Me-3-thienyl | 2,3-Cl-4-Me-5-CN-1H-pyrrol-1-yl |
| 87 | 4-Cl-2-F—$C_6H_3$ | 1H-pyrrol-1-yl | 2,4-Cl-3-Me-5-CN-1H-pyrrol-1-yl |
| 88 | 2-F-3-Me—$C_6H_3$ | 2-F-1H-pyrrol-1-yl | 3,4-Cl-2-Me-5-CN-1H-pyrrol-1-yl |
| 89 | 2-F-4-Me—$C_6H_3$ | 3-F-1H-pyrrol-1-yl | |

TABLE 6

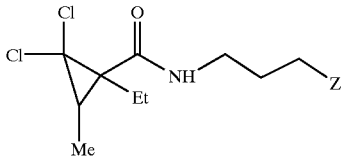

Z =

| | Column 1 | Column 2 | Column 3 |
|---|---|---|---|
| 1 | 1H-pyrrol-1-yl | 2-Cl-4-Me-1H-pyrrol-1-yl | 2-CN-5-Me-1H-pyrrol-1-yl |
| 2 | 2-Cl-1H-pyrrol-1-yl | 2-Cl-5-Me-1H-pyrrol-1-yl | 2-CN-5-n-Pr-1H-pyrrol-1-yl |
| 3 | 3-Cl-1H-pyrrol-1-yl | 2-Br-3-Me-1H-pyrrol-1-yl | 2,3,4-triCl-1H-pyrrol-1-yl |
| 4 | 2-CN-1H-pyrrol-1-yl | 2-Br-4-Me-1H-pyrrol-1-yl | 2,3,5-triCl-1H-pyrrol-1-yl |
| 5 | 2-Br-1H-pyrrol-1-yl | 2-Br-5-Me-1H-pyrrol-1-yl | 2-CN-3,4-diCl-1H-pyrrol-1-yl |
| 6 | 3-Br-1H-pyrrol-1-yl | 2-n-Pr-5-Br-1H-pyrrol-1-yl | 2-CN-3,5-diCl-1H-pyrrol-1-yl |
| 7 | 2-$CH_2CN$-1H-pyrrol-1-yl | 2-CN-3-Cl-1H-pyrrol-1-yl | 2-CN-4,5-diCl-1H-pyrrol-1-yl |
| 8 | 2,3-diCl-1H-pyrrol-1-yl | 2-CN-4-Cl-1H-pyrrol-1-yl | 2-CN-3-Cl-4-Me-1H-pyrrol-1-yl |
| 9 | 2,4-diCl-1H-pyrrol-1-yl | 2-CN-5-Cl-1H-pyrrol-1-yl | 2-CN-3-Cl-5-Me-1H-pyrrol-1-yl |
| 10 | 2,5-diCl-1H-pyrrol-1-yl | 2-CN-3-Br-1H-pyrrol-1-yl | 2-CN-3-Me-4-Cl-1H-pyrrol-1-yl |
| 11 | 3,4-diCl-1H-pyrrol-1-yl | 2-CN-4-Br-1H-pyrrol-1-yl | 2-CN-3-Me-5-Cl-1H-pyrrol-1-yl |
| 12 | 2,3-diBr-1H-pyrrol-1-yl | 2-CN-5-Br-1H-pyrrol-1-yl | 2-CN-4-Me-5-Cl-1H-pyrrol-1-yl |
| 13 | 2,4-diBr-1H-pyrrol-1-yl | 2-CN-4-Me-1H-pyrrol-1-yl | 2-CN-4-Cl-5-Me-1H-pyrrol-1-yl |
| 14 | 2,5-diBr-1H-pyrrol-1-yl | 2,3-diCl-4-Me-1H-pyrrol-1-yl | 2,3,4,5-tetraCl-1H-pyrrol-1-yl |
| 15 | 3,4-diBr-1H-pyrrol-1-yl | 2,3-diCl-5-Me-1H-pyrrol-1-yl | 2,3,4-triCl-5-Me-1H-pyrrol-1-yl |
| 16 | 2-Cl-3-Br-1H-pyrrol-1-yl | 2,4-diCl-3-Me-1H-pyrrol-1-yl | 2,3,5-triCl-4-Me-1H-pyrrol-1-yl |
| 17 | 2-Cl-4-Br-1H-pyrrol-1-yl | 2,4-diCl-5-Me-1H-pyrrol-1-yl | 2,4-diCl-3,5-diMe-1H-pyrrol-1-yl |
| 18 | 2-Cl-5-Br-1H-pyrrol-1-yl | 2,5-diCl-3-Me-1H-pyrrol-1-yl | 2,5-diCl-3,4-diMe-1H-pyrrol-1-yl |
| 19 | 3-Cl-4-Br-1H-pyrrol-1-yl | 3,4-diCl-5-Me-1H-pyrrol-1-yl | 3,4-diCl-2,5-diMe-1H-pyrrol-1-yl |
| 20 | 3-Cl-5-Br-1H-pyrrol-1-yl | 2-CN-3,4-diMe-1H-pyrrol-1-yl | 2,3,4-triCl-5-CN-1H-pyrrol-1-yl |
| 21 | 4-Cl-5-Br-1H-pyrrol-1-yl | 2-CN-3,5-diMe-1H-pyrrol-1-yl | 2,4-Cl-3-Me-5-CN-1H-pyrrol-1-yl |
| 22 | 2-Cl-3-Me-1H-pyrrol-1-yl | 2-CN-4,5-diMe-1H-pyrrol-1-yl | |

TABLE 7

$$\text{NC}-\overset{\overset{O}{\|}}{C}-\text{NH}-\overset{\overset{CH_3}{|}}{CH}-CH=CHZ$$

(with t-Bu group on the carbon bearing NC)

Z =

| | Column 1 | Column 2 | Column 3 |
|---|---|---|---|
| 1 | C₆H₅ | 2-CN-4-Me—C₆H₃ | 5-Br-2-thienyl |
| 2 | 2-F—C₆H₄ | 2-CN-5-Me—C₆H₃ | 3-n-Pr-2-thienyl |
| 3 | 3-F—C₆H₄ | 2-CN-6-Me—C₆H₃ | 5-n-Pr-2-thienyl |
| 4 | 4-F—C₆H₄ | 2-Br-4-F—C₆H₃ | 5-i-Pr-2-thienyl |
| 5 | 2-Cl—C₆H₄ | 2-Br-5-F—C₆H₃ | 3-(CH₂CN)-2-thienyl |
| 6 | 3-Cl—C₆H₄ | 3-Br-6-F—C₆H₃ | 3-(CH=CH₂)-2-thienyl |
| 7 | 4-Cl—C₆H₄ | 4-Br-2-F—C₆H₃ | 3-(CH=CHMe)-2-thienyl |
| 8 | 2-Br—C₆H₄ | 2-Cl-5-Me—C₆H₃ | 3-(CH₂CH=CH₂)-2-thienyl |
| 9 | 3-Br—C₆H₄ | 3-Cl-5-Me—C₆H₃ | 3-(CH₂C≡CH)-2-thienyl |
| 10 | 4-Br—C₆H₄ | 3-Cl-6-Me—C₆H₃ | 3-(C≡CMe)-2-thienyl |
| 11 | 2-I—C₆H₄ | 2-n-Pr-3-F—C₆H₃ | 3-(CH=CHBr)-2-thienyl |
| 12 | 3-I—C₆H₄ | 2-n-Pr-4-F—C₆H₃ | 3-(CH=CHCN)-2-thienyl |
| 13 | 4-I—C₆H₄ | 2-n-Pr-5-F—C₆H₃ | 3,5-diF-2-thienyl |
| 14 | 2-Me—C₆H₄ | 2-n-Pr-6-F—C₆H₃ | 3,5-diCl-2-thienyl |
| 15 | 3-Me—C₆H₄ | 2-n-Pr-3-Cl—C₆H₃ | 3,5-diBr-2-thienyl |
| 16 | 4-Me—C₆H₄ | 2-n-Pr-5-Cl—C₆H₃ | 3-F-5-Cl-2-thienyl |
| 17 | 2-Et—C₆H₄ | 2-n-Pr-5-Br—C₆H₃ | 3-Cl-5-F-2-thienyl |
| 18 | 2-CN—C₆H₄ | 2-n-Pr-5-Me—C₆H₃ | 3-F-5-Br-2-thienyl |
| 19 | 2-CF₃—C₆H₄ | 2-n-Pr-6-CN—C₆H₃ | 3-Br-4-F-2-thienyl |
| 20 | 2-n-Pr—C₆H₄ | 2-Cl-3-F—C₆H₃ | 3-Br-5-F-2-thienyl |
| 21 | 2-i-Pr—C₆H₄ | 2-Cl-4-F—C₆H₃ | 3-F-5-Me-2-thienyl |
| 22 | 2-n-Bu—C₆H₄ | 2-Cl-5-F—C₆H₃ | 3-Me-5-F-2-thienyl |
| 23 | 3-SiMe₃—C₆H₄ | 2-Cl-6-F—C₆H₃ | 3-Br-5-Cl-2-thienyl |
| 24 | 2-CH₂F—C₆H₄ | 3-Cl-2-F—C₆H₃ | 3-Cl-5-Me-2-thienyl |
| 25 | 3-CH₂F—C₆H₄ | 3-Cl-6-F—C₆H₃ | 3-Me-5-Cl-2-thienyl |
| 26 | 2-CH₂CN—C₆H₄ | 4-Cl-2-F—C₆H₃ | 3-Br-5-Me-2-thienyl |
| 27 | 2-CH₂CH₂F—C₆H₄ | 2-F-3-Me—C₆H₃ | 3-Me-5-Br-2-thienyl |
| 28 | 2-CH₂CH₂CN—C₆H₄ | 2-F-5-Me—C₆H₃ | 3-n-Pr-5-Cl-2-thienyl |
| 29 | 2-(CH=CH₂)—C₆H₄ | 2-F-6-Me—C₆H₃ | 3-CN-5-F-2-thienyl |
| 30 | 2-(CH=CHMe)—C₆H₄ | 3-F-6-Me—C₆H₃ | 3-CN-5-Cl-2-thienyl |
| 31 | 2-(CH₂CH=CH₂)—C₆H₄ | 2,3,4-triF—C₆H₂ | 3-CN-5-Br-2-thienyl |
| 32 | 2-(CH=CHCl)—C₆H₄ | 2,3,5-triF—C₆H₂ | 3-CN-5-Me-2-thienyl |
| 33 | 2-(CH=CHBr)—C₆H₄ | 2,3,6-triF—C₆H₂ | 3-thienyl |
| 34 | 2-(CH=CHCN)—C₆H₄ | 2,4,5-triF—C₆H₂ | 2-F-3-thienyl |
| 35 | 2-(C≡CH)—C₆H₄ | 2,3,5-triCl—C₆H₂ | 4-F-3-thienyl |
| 36 | 2-(CH₂C≡CH)—C₆H₄ | 2,3-diF-5-Cl—C₆H₂ | 5-F-3-thienyl |
| 37 | 2-(C≡CMe)—C₆H₄ | 2,3-diF-6-Cl—C₆H₂ | 2-I-3-thienyl |
| 38 | 2-(t-Bu)—C₆H₄ | 2,5-diF-3-Cl—C₆H₂ | 5-I-3-thienyl |
| 39 | 2-(CH₂C≡CMe)—C₆H₄ | 2,5-diF-6-Cl—C₆H₂ | 2-Me-3-thienyl |
| 40 | 2-[CH(F)Me]—C₆H₄ | 2,6-diF-3-Cl—C₆H₂ | 5-Me-3-thienyl |
| 41 | 2-[CH(Cl)Me]—C₆H₄ | 2,3-diCl-5-F—C₆H₂ | 2-Et-3-thienyl |
| 42 | 2-[CH(Br)Me]—C₆H₄ | 2,3-diCl-6-F—C₆H₂ | 2-Cl-3-thienyl |
| 43 | 2-[CH(CN)Me]—C₆H₄ | 2,5-diCl-3-F—C₆H₂ | 4-Cl-3-thienyl |
| 44 | 2-[CH(CN)CH₂Me]—C₆H₄ | 2,5-diCl-6-F—C₆H₂ | 5-Cl-3-thienyl |
| 45 | 2-[CH=C(Me)₂]—C₆H₄ | 2,6-diCl-3-F—C₆H₂ | 2-CN-3-thienyl |
| 46 | 2-[CH(Me)CH=CH₂]—C₆H₄ | 2,3-diF-5-Me—C₆H₂ | 2-(C≡CH)-3-thienyl |
| 47 | 2-(CH₂C(Me)=CH₂)—C₆H₄ | 2,5-diF-3-Me—C₆H₂ | 2-Br-3-thienyl |
| 48 | 2-(CH₂CH₂C≡CH)—C₆H₄ | 2,5-diF-6-Me—C₆H₂ | 5-Br-3-thienyl |
| 49 | 2,3-diF—C₆H₃ | 2-CN-3,5-diCl—C₆H₂ | 2-n-Pr-3-thienyl |
| 50 | 2,4-diF—C₆H₃ | 2-CN-3,6-diCl—C₆H₂ | 2-i-Pr-3-thienyl |
| 51 | 2,5-diF—C₆H₃ | 2-CN-3,5-diF—C₆H₂ | 2-n-Bu-3-thienyl |
| 52 | 2,6-diF—C₆H₃ | 2-CN-3,6-diF—C₆H₂ | 2-CH₂F-3-thienyl |
| 53 | 3,4-diF—C₆H₃ | 2-CN-5,6-diF—C₆H₂ | 2-(CH₂CN)-3-thienyl |
| 54 | 3,5-diF—C₆H₃ | 2-CN-3-F-5-Cl—C₆H₂ | 2-t-Bu-3-thienyl |
| 55 | 2,3-diCl—C₆H₃ | 2-CN-3-Me-5-Cl—C₆H₂ | 2-SiMe₃-3-thienyl |
| 56 | 2,5-diCl—C₆H₃ | 2-CN-3-Me-5-F—C₆H₂ | 2-(CH₂CH₂CN)-3-thienyl |
| 57 | 2,5-diBr—C₆H₃ | 2-Cl-3-F-5-Me—C₆H₂ | 2-(CH=CH₂)-3-thienyl |
| 58 | 2-Br-5-Cl—C₆H₃ | 2-F-3-Cl-5-Me—C₆H₂ | 2-(CH=CHMe)-3-thienyl |
| 59 | 3-Br-2-Cl—C₆H₃ | 2,3,4,5-tetraF—C₆H | 2-(CH₂CH=CH₂)-3-thienyl |
| 60 | 3-Br-6-Cl—C₆H₃ | 2,3,4,6-tetraF—C₆H | 2-(CH₂C≡CH)-3-thienyl |
| 61 | 4-Br-2-Cl—C₆H₃ | 2,3,5,6-tetraF—C₆H | 2-(C≡CMe)-3-thienyl |
| 62 | 2-Br-4-Me—C₆H₃ | 2-thienyl | 2-(CH=CHCN)-3-thienyl |
| 63 | 2-Br-5-Me—C₆H₃ | 3-F-2-thienyl | 2,4-diF-3-thienyl |
| 64 | 3-Br-6-Me—C₆H₃ | 4-F-2-thienyl | 2,5-diF-3-thienyl |
| 65 | 2-CN-3-F—C₆H₃ | 5-F-2-thienyl | 2,4-diCl-3-thienyl |
| 66 | 2-CN-4-F—C₆H₃ | 5-I-2-thienyl | 2,5-diCl-3-thienyl |

TABLE 7-continued

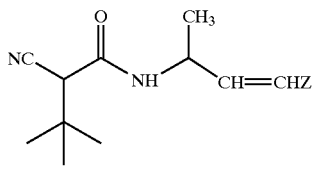

Z =

| | Column 1 | Column 2 | Column 3 |
|---|---|---|---|
| 67 | 2-CN-5-F—$C_6H_3$ | 3-Me-2-thienyl | 2,5-diBr-3-thienyl |
| 68 | 2-CN-6-F—$C_6H_3$ | 5-Me-2-thienyl | 2-Cl-5-Br-3-thienyl |
| 69 | 2-CN-3-Cl—$C_6H_3$ | 3-Et-2-thienyl | 2-Br-5-Cl-3-thienyl |
| 70 | 2-CN-5-Cl—$C_6H_3$ | 5-Et-2-thienyl | 2-Br-5-Me-3-thienyl |
| 71 | 2-CN-6-Cl—$C_6H_3$ | 3-Cl-2-thienyl | 2-Me-5-Br-3-thienyl |
| 72 | 2-CN-5-Br—$C_6H_3$ | 4-Cl-2-thienyl | 2-n-Pr-5-Cl-3-thienyl |
| 73 | 2-CN-3-I—$C_6H_3$ | 5-Cl-2-thienyl | 2-n-Pr-5-Br-3-thienyl |
| 74 | 2-CN-3-$CF_3$—$C_6H_3$ | 3-CN-2-thienyl | 2-CN-5-Cl-3-thienyl |
| 75 | 2-CN-6-$CF_3$—$C_6H_3$ | 5-(C≡CH)-2-thienyl | 2-CN-5-Br-3-thienyl |
| 76 | 2-CN-3-Me—$C_6H_3$ | 3-Br-2-thienyl | 2-CN-5-Me-3-thienyl |

TABLE 8

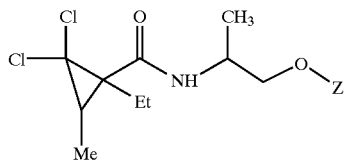

Z =

| | Column 1 | Column 2 | Column 3 |
|---|---|---|---|
| 1 | $C_6H_5$ | 2-CN-3-Cl—$C_6H_3$ | 2,3,5,6-tetraCl—$C_6H$ |
| 2 | 2-F—$C_6H_4$ | 2-CN-4-Cl—$C_6H_3$ | 2,3,5-triCl-6-CN—$C_6H$ |
| 3 | 3-F—$C_6H_4$ | 2-CN-5-Cl—$C_6H_3$ | 2,3,4-triF-6-CN—$C_6H$ |
| 4 | 4-F—$C_6H_4$ | 2-CN-6-Cl—$C_6H_3$ | 2,5-diCl-3,6-diF—$C_6H$ |
| 5 | 2-Cl—$C_6H_4$ | 2-CN-5-Br—$C_6H_3$ | 2,5-diF-3-Cl-6-CN—$C_6H$ |
| 6 | 3-Cl—$C_6H_4$ | 2-CN-3-I—$C_6H_3$ | 1H-pyrrol-1-yl |
| 7 | 4-Cl—$C_6H_4$ | 2-CN-3-$CF_3$—$C_6H_3$ | 2-F-1H-pyrrol-1-yl |
| 8 | 2-Br—$C_6H_4$ | 2-CN-6-$CF_3$—$C_6H_3$ | 3-F-1H-pyrrol-1-yl |
| 9 | 3-Br—$C_6H_4$ | 2-CN-3-Me—$C_6H_3$ | 2-I-1H-pyrrol-1-yl |
| 10 | 4-Br—$C_6H_4$ | 2-CN-5-Me—$C_6H_3$ | 2-Cl-1H-pyrrol-1-yl |
| 11 | 2-I—$C_6H_4$ | 2-Br-4-F—$C_6H_3$ | 3-Cl-1H-pyrrol-1-yl |
| 12 | 3-I—$C_6H_4$ | 2-Br-5-F—$C_6H_3$ | 2-CN-1H-pyrrol-1-yl |
| 13 | 4-I—$C_6H_4$ | 3-Br-6-F—$C_6H_3$ | 2-Br-1H-pyrrol-1-yl |
| 14 | 2-Me—$C_6H_4$ | 2-Cl-3-Me—$C_6H_3$ | 2-n-Pr-1H-pyrrol-1-yl |
| 15 | 3-Me—$C_6H_4$ | 2-Cl-5-Me—$C_6H_3$ | 2-n-Bu-1H-pyrrol-1-yl |
| 16 | 4-Me—$C_6H_4$ | 3-Cl-5-Me—$C_6H_3$ | 2-t-Bu-1H-pyrrol-1-yl |
| 17 | 2-Et—$C_6H_4$ | 2-n-Pr-3-F—$C_6H_3$ | 2,3-diCl-1H-pyrrol-1-yl |
| 18 | 2-CN—$C_6H_4$ | 2-n-Pr-4-F—$C_6H_3$ | 2,4-diCl-1H-pyrrol-1-yl |
| 19 | 2-$CF_3$—$C_6H_4$ | 2-n-Pr-5-F—$C_6H_3$ | 2,5-diCl-1H-pyrrol-1-yl |
| 20 | 2-n-Pr—$C_6H_4$ | 2-n-Pr-6-F—$C_6H_3$ | 2,3-diBr-1H-pyrrol-1-yl |
| 21 | 3-n-Pr—$C_6H_4$ | 2-n-Pr-3-Cl—$C_6H_3$ | 2,4-diBr-1H-pyrrol-1-yl |
| 22 | 2-i-Pr—$C_6H_4$ | 2-n-Pr-5-Cl—$C_6H_3$ | 2,5-diBr-1H-pyrrol-1-yl |
| 23 | 3-i-Pr—$C_6H_4$ | 2-n-Pr-5-Br—$C_6H_3$ | 2-Cl-3-Br-1H-pyrrol-1-yl |
| 24 | 2-n-Bu—$C_6H_4$ | 2-n-Pr-5-Me—$C_6H_3$ | 2-Cl-4-Br-1H-pyrrol-1-yl |
| 25 | 3-$SiMe_3$—$C_6H_4$ | 2-Cl-3-F—$C_6H_3$ | 2-Cl-5-Br-1H-pyrrol-1-yl |
| 26 | 2-$CH_2F$—$C_6H_4$ | 2-Cl-4-F—$C_6H_3$ | 3-Cl-5-Br-1H-pyrrol-1-yl |
| 27 | 3-$CH_2F$—$C_6H_4$ | 2-Cl-5-F—$C_6H_3$ | 4-Cl-5-Br-1H-pyrrol-1-yl |
| 28 | 2-$CH_2Cl$—$C_6H_4$ | 2-Cl-6-F—$C_6H_3$ | 2-Cl-3-Me-1H-pyrrol-1-yl |
| 29 | 2-$CH_2Br$—$C_6H_4$ | 3-Cl-2-F—$C_6H_3$ | 2-Cl-4-Me-1H-pyrrol-1-yl |
| 30 | 2-$CH_2CN$—$C_6H_4$ | 3-Cl-6-F—$C_6H_3$ | 2-Cl-5-Me-1H-pyrrol-1-yl |
| 31 | 2-$CH_2CH_2F$—$C_6H_4$ | 2-F-3-Me—$C_6H_3$ | 2-Br-3-Me-1H-pyrrol-1-yl |
| 32 | 2-$CH_2CH_2Cl$—$C_6H_4$ | 2-F-5-Me—$C_6H_3$ | 2-Br-4-Me-1H-pyrrol-1-yl |
| 33 | 2-$CH_2CH_2CN$—$C_6H_4$ | 2-F-6-Me—$C_6H_3$ | 2-Br-5-Me-1H-pyrrol-1-yl |
| 34 | 2-(CH=$CH_2$)—$C_6H_4$ | 3-F-6-Me—$C_6H_3$ | 3-Br-4-Me-1H-pyrrol-1-yl |
| 35 | 2-(CH=CHMe)—$C_6H_4$ | 2,3,4-triF—$C_6H_2$ | 2-CN-3-Cl-1H-pyrrol-1-yl |
| 36 | 2-($CH_2$CH=$CH_2$)—$C_6H_4$ | 2,3,5-triF—$C_6H_2$ | 2-CN-4-Cl-1H-pyrrol-1-yl |
| 37 | 2-(C≡CH)—$C_6H_4$ | 2,3,6-triF—$C_6H_2$ | 2-CN-5-Cl-1H-pyrrol-1-yl |
| 38 | 2-($CH_2$C≡CH)—$C_6H_4$ | 2,4,5-triF—$C_6H_2$ | 2-CN-3-Br-1H-pyrrol-1-yl |

TABLE 8-continued

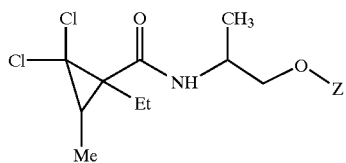

Z =

| | Column 1 | Column 2 | Column 3 |
|---|---|---|---|
| 39 | 2-(C≡CMe)—$C_6H_4$ | 2,4,6-triF—$C_6H_2$ | 2-CN-4-Br-1H-pyrrol-1-yl |
| 40 | 2-(C≡CCH$_2$Me)—$C_6H_4$ | 2,3,5-triCl—$C_6H_2$ | 2-CN-5-Br-1H-pyrrol-1-yl |
| 41 | 2-(t-Bu)—$C_6H_4$ | 2,3,6-triCl—$C_6H_2$ | 2-CN-3-Me-1H-pyrrol-1-yl |
| 42 | 2-[CH(F)Me]—$C_6H_4$ | 2,3-diF-5-Cl—$C_6H_2$ | 2-CN-4-Me-1H-pyrrol-1-yl |
| 43 | 2-[CH(Cl)Me]—$C_6H_4$ | 2,3-diF-6-Cl—$C_6H_2$ | 2-CN-5-Me-1H-pyrrol-1-yl |
| 44 | 2-[CH(Br)Me]—$C_6H_4$ | 2,5-diF-3-Cl—$C_6H_2$ | 2-CN-5-n-Pr-1H-pyrrol-1-yl |
| 45 | 2-[CH(CN)Me]—$C_6H_4$ | 2,5-diF-6-Cl—$C_6H_2$ | 2,3,4-triCl-1H-pyrrol-1-yl |
| 46 | 2-[CH=C(Me)$_2$]—$C_6H_4$ | 2,6-diF-3-Cl—$C_6H_2$ | 2,3,5-triCl-1H-pyrrol-1-yl |
| 47 | 2-[CH(Me)CH=CH$_2$]—$C_6H_4$ | 2,3-diCl-5-F—$C_6H_2$ | 2,3-diCl-4-Me-1H-pyrrol-1-yl |
| 48 | 2-(CH$_2$C(Me)=CH$_2$)—$C_6H_4$ | 2,5-diCl-3-F—$C_6H_2$ | 2,3-diCl-5-Me-1H-pyrrol-1-yl |
| 49 | 2-(CH$_2$CH$_2$C≡CH)—$C_6H_4$ | 2,5-diCl-6-F—$C_6H_2$ | 2,4-diCl-3-Me-1H-pyrrol-1-yl |
| 50 | 2,3-diF—$C_6H_3$ | 2,6-diCl-3-F—$C_6H_2$ | 2,4-diCl-5-Me-1H-pyrrol-1-yl |
| 51 | 2,4-diF—$C_6H_3$ | 2,3-diCl-5-Me—$C_6H_2$ | 2,5-diCl-3-Me-1H-pyrrol-1-yl |
| 52 | 2,5-diF—$C_6H_3$ | 2,5-diF-3-Me—$C_6H_2$ | 2-CN-3,5-diMe-1H-pyrrol-1-yl |
| 53 | 2,6-diF—$C_6H_3$ | 2,5-diF-6-Me—$C_6H_2$ | 2-CN-4,5-diMe-1H-pyrrol-1-yl |
| 54 | 3,4-diF—$C_6H_3$ | 2,5-diCl-3-Me—$C_6H_2$ | 2-CN-3,5-diCl-1H-pyrrol-1-yl |
| 55 | 3,5-diF—$C_6H_3$ | 2,5-diCl-6-Me—$C_6H_2$ | 2-CN-4,5-diCl-1H-pyrrol-1-yl |
| 56 | 2,3-diCl—$C_6H_3$ | 2-CN-3,5-diMe—$C_6H_2$ | 2-CN-3-Cl-4-Me-1H-pyrrol-1-yl |
| 57 | 2,4-diCl—$C_6H_3$ | 2-CN-3,5-diCl—$C_6H_2$ | 2-CN-3-Cl-5-Me-1H-pyrrol-1-yl |
| 58 | 2,5-diCl—$C_6H_3$ | 2-CN-3,5-diF—$C_6H_2$ | 2-CN-3-Me-4-Cl-1H-pyrrol-1-yl |
| 59 | 2,6-diCl—$C_6H_3$ | 2-CN-5,6-diF—$C_6H_2$ | 2-CN-3-Me-5-Cl-1H-pyrrol-1-yl |
| 60 | 3,4-diCl—$C_6H_3$ | 2-CN-3-F-5-Cl—$C_6H_2$ | 2-CN-4-Me-5-Cl-1H-pyrrol-1-yl |
| 61 | 3,5-diCl—$C_6H_3$ | 2-CN-3-Me-5-Cl—$C_6H_2$ | 2-CN-4-Cl-5-Me-1H-pyrrol-1-yl |
| 62 | 2,5-diBr—$C_6H_3$ | 2-CN-3-Me-5-F—$C_6H_2$ | 2-CN-4-Br-5-Me-1H |
| 63 | 2-Br-5-Cl—$C_6H_3$ | 2-CN-5-F-6-Cl—$C_6H_2$ | 2,3,4,5-tetraCl-1H-pyrrol-1-yl |
| 64 | 3-Br-2-Cl—$C_6H_3$ | 2-Cl-3-F-5-Me—$C_6H_2$ | 2,3,5-triCl-4-Me-1H-pyrrol-1-yl |
| 65 | 3-Br-6-Cl—$C_6H_3$ | 2-Cl-3-F-6-Me—$C_6H_2$ | 2,5-diCl-3,4-diMe-1H-pyrrol-1-yl |
| 66 | 2-Br-5-Me—$C_6H_3$ | 2-F-3-Cl-5-Me—$C_6H_2$ | 2,3,4-triCl-5-CN-1H-pyrrol-1-yl |
| 67 | 3-Br-6-Me—$C_6H_3$ | 2,3,4,5-tetraF—$C_6H$ | 2,3-triMe-5-CN-1H-pyrrol-1-yl |
| 68 | 2-CN-3-F—$C_6H_3$ | 2,3,4,6-tetraF—$C_6H$ | 2,3-Cl-4-Me-5-CN-1H-pyrrol-1-yl |
| 69 | 2-CN-4-F—$C_6H_3$ | 2,3,5,6-tetraF—$C_6H$ | 2,4-Cl-3-Me-5-CN-1H-pyrrol-1-yl |
| 70 | 2-CN-5-F—$C_6H_3$ | 2,3,4,5-tetraCl—$C_6H$ | 3,4-Cl-2-Me-5-CN-1H-pyrrol-1-yl |
| 71 | 2-CN-6-F—$C_6H_3$ | 2,3,4,6-tetraCl—$C_6H$ | |

TABLE 9

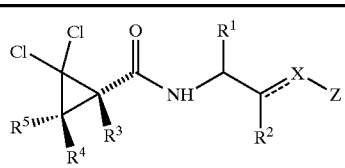

| $R^1$ | $R^2$ | $R^3$ | $R^4$ | $R^5$ | X | | Column 1 | Column 2 |
|---|---|---|---|---|---|---|---|---|
| H | H | Et | Me | H | $CH_2$ | Z = | $C_6H_5$ | 2,5-diF—$C_6H_3$ |
| H | H | Et | Me | H | $CH_2$ | Z = | 2-F—$C_6H_4$ | 2,5-diCl—$C_6H_3$ |
| H | H | Et | Me | H | $CH_2$ | Z = | 2-Cl—$C_6H_4$ | 2-Cl-5-F—$C_6H_3$ |
| H | H | Et | Me | H | $CH_2$ | Z = | 2-CN—$C_6H_4$ | 2-F-5-Cl—$C_6H_3$ |
| H | H | Et | Me | H | $CH_2$ | Z = | 3-Cl—$C_6H_4$ | 2-CN-5-F—$C_6H_3$ |
| H | H | Et | Me | H | $CH_2$ | Z = | 3-F—$C_6H_4$ | 2-CN-5-Cl—$C_6H_3$ |
| H | H | Et | Me | H | =CH | Z = | $C_6H_5$ | 2,5-diF—$C_6H_3$ |
| H | H | Et | Me | H | =CH | Z = | 2-F—$C_6H_4$ | 2,5-diCl—$C_6H_3$ |
| H | H | Et | Me | H | =CH | Z = | 2-Cl—$C_6H_4$ | 2-Cl-5-F—$C_6H_3$ |
| H | H | Et | Me | H | =CH | Z = | 2-CN—$C_6H_4$ | 2-F-5-Cl—$C_6H_3$ |
| H | H | Et | Me | H | =CH | Z = | 3-Cl—$C_6H_4$ | 2-CN-5-F—$C_6H_3$ |
| H | H | Et | Me | H | =CH | Z = | 3-F—$C_6H_4$ | 2-CN-5-Cl—$C_6H_3$ |
| H | H | Et | Me | H | O | Z = | $C_6H_5$ | 2,5-diF—$C_6H_3$ |
| H | H | Et | Me | H | O | Z = | 2-F—$C_6H_4$ | 2,5-diCl—$C_6H_3$ |
| H | H | Et | Me | H | O | Z = | 2-Cl—$C_6H_4$ | 2-Cl-5-F—$C_6H_3$ |
| H | H | Et | Me | H | O | Z = | 2-CN—$C_6H_4$ | 2-F-5-Cl—$C_6H_3$ |
| H | H | Et | Me | H | O | Z = | 3-Cl—$C_6H_4$ | 2-CN-5-F—$C_6H_3$ |
| H | H | Et | Me | H | O | Z = | 3-F—$C_6H_4$ | 2-CN-5-Cl—$C_6H_3$ |

TABLE 9-continued

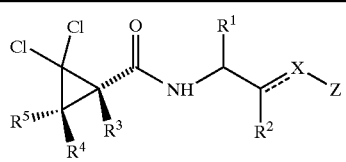

| R¹ | R² | R³ | R⁴ | R⁵ | X | | Column 1 | Column 2 |
|---|---|---|---|---|---|---|---|---|
| Me | Me | Et | Me | H | O | Z = | $C_6H_5$ | 2,5-diF—$C_6H_3$ |
| Me | Me | Et | Me | H | O | Z = | 2-F—$C_6H_4$ | 2,5-diCl—$C_6H_3$ |
| Me | Me | Et | Me | H | O | Z = | 2-Cl—$C_6H_4$ | 2-Cl-5-F—$C_6H_3$ |
| Me | Me | Et | Me | H | O | Z = | 2-CN—$C_6H_4$ | 2-F-5-Cl—$C_6H_3$ |
| Me | Me | Et | Me | H | O | Z = | 3-Cl—$C_6H_4$ | 2-CN-5-F—$C_6H_3$ |
| Me | Me | Et | Me | H | O | Z = | 3-F—$C_6H_4$ | 2-CN-5-Cl—$C_6H_3$ |
| Me | Et | Et | Me | H | O | Z = | $C_6H_5$ | 2,5-diF—$C_6H_3$ |
| Me | Et | Et | Me | H | O | Z = | 2-F—$C_6H_4$ | 2,5-diCl—$C_6H_3$ |
| Me | Et | Et | Me | H | O | Z = | 2-Cl—$C_6H_4$ | 2-Cl-5-F—$C_6H_3$ |
| Me | Et | Et | Me | H | O | Z = | 2-CN—$C_6H_4$ | 2-F-5-Cl—$C_6H_3$ |
| Me | Et | Et | Me | H | O | Z = | 3-Cl—$C_6H_4$ | 2-CN-5-F—$C_6H_3$ |
| Me | Et | Et | Me | H | O | Z = | 3-F—$C_6H_4$ | 2-CN-5-Cl—$C_6H_3$ |
| Me | H | Et | Me | H | CH(Me) | Z = | $C_6H_5$ | 2,5-diF—$C_6H_3$ |
| Me | H | Et | Me | H | CH(Me) | Z = | 2-F—$C_6H_4$ | 2,5-diCl—$C_6H_3$ |
| Me | H | Et | Me | H | CH(Me) | Z = | 2-Cl—$C_6H_4$ | 2-Cl-5-F—$C_6H_3$ |
| Me | H | Et | Me | H | CH(Me) | Z = | 2-CN—$C_6H_4$ | 2-F-5-Cl—$C_6H_3$ |
| Me | H | Et | Me | H | CH(Me) | Z = | 3-Cl—$C_6H_4$ | 2-CN-5-F—$C_6H_3$ |
| Me | H | Et | Me | H | CH(Me) | Z = | 3-F—$C_6H_4$ | 2-CN-5-Cl—$C_6H_3$ |
| Me | H | Et | Me | H | CH(Et) | Z = | $C_6H_5$ | 2,5-diF—$C_6H_3$ |
| Me | H | Et | Me | H | CH(Et) | Z = | 2-F—$C_6H_4$ | 2,5-diCl—$C_6H_3$ |
| Me | H | Et | Me | H | CH(Et) | Z = | 2-Cl—$C_6H_4$ | 2-Cl-5-F—$C_6H_3$ |
| Me | H | Et | Me | H | CH(Et) | Z = | 2-CN—$C_6H_4$ | 2-F-5-Cl—$C_6H_3$ |
| Me | H | Et | Me | H | CH(Et) | Z = | 3-Cl—$C_6H_4$ | 2-CN-5-F—$C_6H_3$ |
| Me | H | Et | Me | H | CH(Et) | Z = | 3-F—$C_6H_4$ | 2-CN-5-Cl—$C_6H_3$ |
| Me | H | Et | Me | H | CH(n-Pr) | Z = | $C_6H_5$ | 2,5-diF—$C_6H_3$ |
| Me | H | Et | Me | H | CH(n-Pr) | Z = | 2-F—$C_6H_4$ | 2,5-diCl—$C_6H_3$ |
| Me | H | Et | Me | H | CH(n-Pr) | Z = | 2-Cl—$C_6H_4$ | 2-Cl-5-F—$C_6H_3$ |
| Me | H | Et | Me | H | CH(n-Pr) | Z = | 2-CN—$C_6H_4$ | 2-F-5-Cl—$C_6H_3$ |
| Me | H | Et | Me | H | CH(n-Pr) | Z = | 3-Cl—$C_6H_4$ | 2-CN-5-F—$C_6H_3$ |
| Me | H | Et | Me | H | CH(n-Pr) | Z = | 3-F—$C_6H_4$ | 2-CN-5-Cl—$C_6H_3$ |
| Me | H | Et | Me | H | =C(Me) | Z = | $C_6H_5$ | 2,5-diF—$C_6H_3$ |
| Me | H | Et | Me | H | =C(Me) | Z = | 2-F—$C_6H_4$ | 2,5-diCl—$C_6H_3$ |
| Me | H | Et | Me | H | =C(Me) | Z = | 2-Cl—$C_6H_4$ | 2-Cl-5-F—$C_6H_3$ |
| Me | H | Et | Me | H | =C(Me) | Z = | 2-CN—$C_6H_4$ | 2-F-5-Cl—$C_6H_3$ |
| Me | H | Et | Me | H | =C(Me) | Z = | 3-Cl—$C_6H_4$ | 2-CN-5-F—$C_6H_3$ |
| Me | H | Et | Me | H | =C(Me) | Z = | 3-F—$C_6H_4$ | 2-CN-5-Cl—$C_6H_3$ |
| Me | H | Et | Me | H | =C(Et) | Z = | $C_6H_5$ | 2,5-diF—$C_6H_3$ |
| Me | H | Et | Me | H | =C(Et) | Z = | 2-F—$C_6H_4$ | 2,5-diCl—$C_6H_3$ |
| Me | H | Et | Me | H | =C(Et) | Z = | 2-Cl—$C_6H_4$ | 2-Cl-5-F—$C_6H_3$ |
| Me | H | Et | Me | H | =C(Et) | Z = | 2-CN—$C_6H_4$ | 2-F-5-Cl—$C_6H_3$ |
| Me | H | Et | Me | H | =C(Et) | Z = | 3-Cl—$C_6H_4$ | 2-CN-5-F—$C_6H_3$ |
| Me | H | Et | Me | H | =C(Et) | Z = | 3-F—$C_6H_4$ | 2-CN-5-Cl—$C_6H_3$ |
| Me | H | Et | Me | H | $CH_2$ | Z = | $C_6H_5$ | 2,5-diF—$C_6H_3$ |
| Me | H | Et | Me | H | $CH_2$ | Z = | 2-F—$C_6H_4$ | 2,5-diCl—$C_6H_3$ |
| Me | H | Et | Me | H | $CH_2$ | Z = | 2-Cl—$C_6H_4$ | 2-Cl-5-F—$C_6H_3$ |
| Me | H | Et | Me | H | $CH_2$ | Z = | 2-CN—$C_6H_4$ | 2-F-5-Cl—$C_6H_3$ |
| Me | H | Et | Me | H | $CH_2$ | Z = | 3-Cl—$C_6H_4$ | 2-CN-5-F—$C_6H_3$ |
| Me | H | Et | Me | H | $CH_2$ | Z = | 3-F—$C_6H_4$ | 2-CN-5-Cl—$C_6H_3$ |
| Me | H | Et | Me | H | =CH | Z = | $C_6H_5$ | 2,5-diF—$C_6H_3$ |
| Me | H | Et | Me | H | =CH | Z = | 2-F—$C_6H_4$ | 2,5-diCl—$C_6H_3$ |
| Me | H | Et | Me | H | =CH | Z = | 2-Cl—$C_6H_4$ | 2-Cl-5-F—$C_6H_3$ |
| Me | H | Et | Me | H | =CH | Z = | 2-CN—$C_6H_4$ | 2-F-5-Cl—$C_6H_3$ |
| Me | H | Et | Me | H | =CH | Z = | 3-Cl—$C_6H_4$ | 2-CN-5-F—$C_6H_3$ |
| Me | H | Et | Me | H | =CH | Z = | 3-F—$C_6H_4$ | 2-CN-5-Cl—$C_6H_3$ |
| Me | H | Et | H | Me | O | Z = | $C_6H_5$ | 2,5-diF—$C_6H_3$ |
| Me | H | Et | H | Me | O | Z = | 2-F—$C_6H_4$ | 2,5-diCl—$C_6H_3$ |
| Me | H | Et | H | Me | O | Z = | 2-Cl—$C_6H_4$ | 2-Cl-5-F—$C_6H_3$ |
| Me | H | Et | H | Me | O | Z = | 2-CN—$C_6H_4$ | 2-F-5-Cl—$C_6H_3$ |
| Me | H | Et | H | Me | O | Z = | 3-Cl—$C_6H_4$ | 2-CN-5-F—$C_6H_3$ |
| Me | H | Et | H | Me | O | Z = | 3-F—$C_6H_4$ | 2-CN-5-Cl—$C_6H_3$ |
| Me | H | Et | H | Me | $CH_2$ | Z = | $C_6H_5$ | 2,5-diF—$C_6H_3$ |
| Me | H | Et | H | Me | $CH_2$ | Z = | 2-F—$C_6H_4$ | 2,5-diCl—$C_6H_3$ |
| Me | H | Et | H | Me | $CH_2$ | Z = | 2-Cl—$C_6H_4$ | 2-Cl-5-F—$C_6H_3$ |
| Me | H | Et | H | Me | $CH_2$ | Z = | 2-CN—$C_6H_4$ | 2-F-5-Cl—$C_6H_3$ |
| Me | H | Et | H | Me | $CH_2$ | Z = | 3-Cl—$C_6H_4$ | 2-CN-5-F—$C_6H_3$ |
| Me | H | Et | H | Me | $CH_2$ | Z = | 3-F—$C_6H_4$ | 2-CN-5-Cl—$C_6H_3$ |
| Me | H | Et | H | Me | =CH | Z = | $C_6H_5$ | 2,5-diF—$C_6H_3$ |
| Me | H | Et | H | Me | =CH | Z = | 2-F—$C_6H_4$ | 2,5-diCl—$C_6H_3$ |

TABLE 9-continued

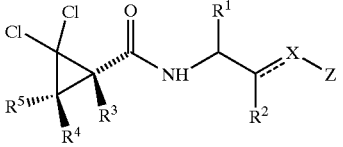

| $R^1$ | $R^2$ | $R^3$ | $R^4$ | $R^5$ | X | | Column 1 | Column 2 |
|---|---|---|---|---|---|---|---|---|
| Me | H | Et | H | Me | =CH | Z = | 2-Cl—$C_6H_4$ | 2-Cl-5-F—$C_6H_3$ |
| Me | H | Et | H | Me | =CH | Z = | 2-CN—$C_6H_4$ | 2-F-5-Cl—$C_6H_3$ |
| Me | H | Et | H | Me | =CH | Z = | 3-Cl—$C_6H_4$ | 2-CN-5-F—$C_6H_3$ |
| Me | H | Et | H | Me | =CH | Z = | 3-F—$C_6H_4$ | 2-CN-5-Cl—$C_6H_3$ |
| Me | H | —$(CH_2)_4$— | | Me | O | Z = | $C_6H_5$ | 2,5-diF—$C_6H_3$ |
| Me | H | —$(CH_2)_4$— | | Me | O | Z = | 2-F—$C_6H_4$ | 2,5-diCl—$C_6H_3$ |
| Me | H | —$(CH_2)_4$— | | Me | O | Z = | 2-Cl—$C_6H_4$ | 2-Cl-5-F—$C_6H_3$ |
| Me | H | —$(CH_2)_4$— | | Me | O | Z = | 2-CN—$C_6H_4$ | 2-F-5-Cl—$C_6H_3$ |
| Me | H | —$(CH_2)_4$— | | Me | O | Z = | 3-Cl—$C_6H_4$ | 2-CN-5-F—$C_6H_3$ |
| Me | H | —$(CH_2)_4$— | | Me | O | Z = | 3-F—$C_6H_4$ | 2-CN-5-Cl—$C_6H_3$ |
| Me | H | —$(CH_2)_3$— | | Me | O | Z = | $C_6H_5$ | 2,5-diF—$C_6H_3$ |
| Me | H | —$(CH_2)_3$— | | Me | O | Z = | 2-F—$C_6H_4$ | 2,5-diCl—$C_6H_3$ |
| Me | H | —$(CH_2)_3$— | | Me | O | Z = | 2-Cl—$C_6H_4$ | 2-Cl-5-F—$C_6H_3$ |
| Me | H | —$(CH_2)_3$— | | Me | O | Z = | 2-CN—$C_6H_4$ | 2-F-5-Cl—$C_6H_3$ |
| Me | H | —$(CH_2)_3$— | | Me | O | Z = | 3-Cl—$C_6H_4$ | 2-CN-5-F—$C_6H_3$ |
| Me | H | —$(CH_2)_3$— | | Me | O | Z = | 3-F—$C_6H_4$ | 2-CN-5-Cl—$C_6H_3$ |
| Me | H | —$(CH_2)_3$— | | Me | $CH_2$ | Z = | $C_6H_5$ | 2,5-diF—$C_6H_3$ |
| Me | H | —$(CH_2)_3$— | | Me | $CH_2$ | Z = | 2-F—$C_6H_4$ | 2,5-diCl—$C_6H_3$ |
| Me | H | —$(CH_2)_3$— | | Me | $CH_2$ | Z = | 2-Cl—$C_6H_4$ | 2-Cl-5-F—$C_6H_3$ |
| Me | H | —$(CH_2)_3$— | | Me | $CH_2$ | Z = | 2-CN—$C_6H_4$ | 2-F-5-Cl—$C_6H_3$ |
| Me | H | —$(CH_2)_3$— | | Me | $CH_2$ | Z = | 3-Cl—$C_6H_4$ | 2-CN-5-F—$C_6H_3$ |
| Me | H | —$(CH_2)_3$— | | Me | $CH_2$ | Z = | 3-F—$C_6H_4$ | 2-CN-5-Cl—$C_6H_3$ |
| H | H | Et | Me | H | $CH_2$ | Z = | $C_6H_5$ | 2,5-diF—$C_6H_3$ |
| H | H | Et | Me | H | $CH_2$ | Z = | 2-F—$C_6H_4$ | 2,5-diCl—$C_6H_3$ |
| H | H | Et | Me | H | $CH_2$ | Z = | 2-Cl—$C_6H_4$ | 2-Cl-5-F—$C_6H_3$ |
| H | H | Et | Me | H | $CH_2$ | Z = | 2-CN—$C_6H_4$ | 2-F-5-Cl—$C_6H_3$ |
| H | H | Et | Me | H | $CH_2$ | Z = | 3-Cl—$C_6H_4$ | 2-CN-5-F—$C_6H_3$ |
| H | H | Et | Me | H | $CH_2$ | Z = | 3-F—$C_6H_4$ | 2-CN-5-Cl—$C_6H_3$ |
| H | H | Et | Me | H | $CH_2$ | Z = | 2-thienyl | 3,5-diF-2-thienyl |
| H | H | Et | Me | H | $CH_2$ | Z = | 3-F-2-thienyl | 3,5-diCl-2-thienyl |
| H | H | Et | Me | H | $CH_2$ | Z = | 3-Cl-2-thienyl | 3-Cl-5-F-2-thienyl |
| H | H | Et | Me | H | $CH_2$ | Z = | 3-CN-2-thienyl | 3-F-5-Cl-2-thienyl |
| H | H | Et | Me | H | $CH_2$ | Z = | 5-F-2-thienyl | 3-CN-5-F-2-thienyl |
| H | H | Et | Me | H | $CH_2$ | Z = | 5-Cl-2-thienyl | 3-CN-5-Cl-2-thienyl |
| H | H | Et | Me | H | $CH_2$ | Z = | 3-thienyl | 2,5-diF-3-thienyl |
| H | H | Et | Me | H | $CH_2$ | Z = | 2-F-3-thienyl | 2,5-diCl-3-thienyl |
| H | H | Et | Me | H | $CH_2$ | Z = | 2-Cl-3-thienyl | 2-Cl-5-F-3-thienyl |
| H | H | Et | Me | H | $CH_2$ | Z = | 2-CN-3-thienyl | 2-F-5-Cl-3-thienyl |
| H | H | Et | Me | H | $CH_2$ | Z = | 5-F-3-thienyl | 2-CN-5-F-3-thienyl |
| H | H | Et | Me | H | $CH_2$ | Z = | 5-Cl-3-thienyl | 2-CN-5-Cl-3-thienyl |
| H | H | Et | Me | H | $CH_2$ | Z = | 1H-pyrrol-1-yl | 2,5-diF-1H-pyrrol-1-yl |
| H | H | Et | Me | H | $CH_2$ | Z = | 2-F-1H-pyrrol-1-yl | 2,5-diCl-1H-pyrrol-1-yl |
| H | H | Et | Me | H | $CH_2$ | Z = | 2-Cl-1H-pyrrol-1-yl | 2-Cl-5-F-1H-pyrrol-1-yl |
| H | H | Et | Me | H | $CH_2$ | Z = | 2-CN-1H-pyrrol-1-yl | 2-F-5-Cl-1H-pyrrol-1-yl |
| H | H | Et | Me | H | $CH_2$ | Z = | 5-F-1H-pyrrol-1-yl | 2-CN-5-Cl-1H-pyrrol-1-yl |
| H | H | Et | Me | H | $CH_2$ | Z = | 5-Cl-1H-pyrrol-1-yl | 2-CN-5-F-1H-pyrrol-1-yl |
| H | H | Et | Me | H | =CH | Z = | 2-thienyl | 3,5-diF-2-thienyl |
| H | H | Et | Me | H | =CH | Z = | 3-F-2-thienyl | 3,5-diCl-2-thienyl |
| H | H | Et | Me | H | =CH | Z = | 3-Cl-2-thienyl | 3-Cl-5-F-2-thienyl |
| H | H | Et | Me | H | =CH | Z = | 3-CN-2-thienyl | 3-F-5-Cl-2-thienyl |
| H | H | Et | Me | H | =CH | Z = | 5-F-2-thienyl | 3-CN-5-F-2-thienyl |
| H | H | Et | Me | H | =CH | Z = | 5-Cl-2-thienyl | 3-CN-5-Cl-2-thienyl |
| H | H | Et | Me | H | =CH | Z = | 3-thienyl | 2,5-diF-3-thienyl |
| H | H | Et | Me | H | =CH | Z = | 2-F-3-thienyl | 2,5-diCl-3-thienyl |
| H | H | Et | Me | H | =CH | Z = | 2-Cl-3-thienyl | 2-Cl-5-F-3-thienyl |
| H | H | Et | Me | H | =CH | Z = | 2-CN-3-thienyl | 2-F-5-Cl-3-thienyl |
| H | H | Et | Me | H | =CH | Z = | 5-F-3-thienyl | 2-CN-5-F-3-thienyl |
| H | H | Et | Me | H | =CH | Z = | 5-Cl-3-thienyl | 2-CN-5-Cl-3-thienyl |
| Me | Ph | H | Me | H | O | Z = | 2-CN—$C_6H_4$ | 2-CN-5-F—$C_6H_3$ |
| Me | Ph | H | Me | H | O | Z = | 2-CN-5-Cl—$C_6H_3$ | 2-CN-5-Me—$C_6H_3$ |
| Me | Ph | H | Me | H | O | Z = | 2,5-diF—$C_6H_3$ | 2-F-5-Cl—$C_6H_3$ |
| Me | Ph | H | H | Me | O | Z = | 2-CN—$C_6H_4$ | 2-CN-5-F—$C_6H_3$ |
| Me | Ph | H | H | Me | O | Z = | 2-CN-5-Cl—$C_6H_3$ | 2-CN-5-Me—$C_6H_3$ |
| Me | Ph | H | H | Me | O | Z = | 2,5-diF—$C_6H_3$ | 2-F-5-Cl—$C_6H_3$ |
| H | H | Et | Me | H | O | Z = | 1H-pyrrol-1-yl | 2,5-diF-1H-pyrrol-1-yl |
| H | H | Et | Me | H | O | Z = | 2-F-1H-pyrrol-1-yl | 2,5-diCl-1H-pyrrol-1-yl |
| H | H | Et | Me | H | O | Z = | 2-Cl-1H-pyrrol-1-yl | 2-Cl-5-F-1H-pyrrol-1-yl |
| H | H | Et | Me | H | O | Z = | 2-CN-1H-pyrrol-1-yl | 2-F-5-Cl-1H-pyrrol-1-yl |

TABLE 9-continued

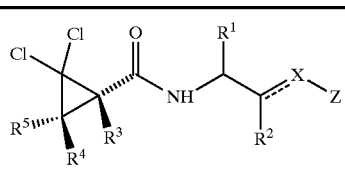

| $R^1$ | $R^2$ | $R^3$ | $R^4$ | $R^5$ | X | | Column 1 | Column 2 |
|---|---|---|---|---|---|---|---|---|
| H | H | Et | Me | H | O | Z = | 5-F-1H-pyrrol-1-yl | 2-CN-5-Cl-1H-pyrrol-1-yl |
| H | H | Et | Me | H | O | Z = | 5-Cl-1H-pyrrol-1-yl | 2-CN-5-F-1H-pyrrol-1-yl |
| Me | H | H | Me | Et | O | Z = | 3-F—$C_6H_4$ | 2-CN-3-Cl—$C_6H_3$ |
| Me | H | H | Me | Et | O | Z = | 2,5-diF—$C_6H_3$ | |
| Me | H | $(CH_2)_2CN$ | Me | H | O | Z = | 3-F—$C_6H_4$ | 2-CN-3-Cl—$C_6H_3$ |
| Me | H | $(CH_2)_2CN$ | Me | H | O | Z = | 2,5-diF—$C_6H_3$ | |
| Me | H | $(CH_2)_2F$ | Me | H | O | Z = | 3-F—$C_6H_4$ | 2-CN-3-Cl—$C_6H_3$ |
| Me | H | $(CH_2)_2F$ | Me | H | O | Z = | 2,5-diF—$C_6H_3$ | |
| Me | H | $CH_2CN$ | Me | H | O | Z = | 3-F—$C_6H_4$ | 2-CN-3-Cl—$C_6H_3$ |
| Me | H | $CH_2CN$ | Me | H | O | Z = | 2,5-diF—$C_6H_3$ | |
| Me | H | $(CH_2)_2Cl$ | Me | H | O | Z = | 3-F—$C_6H_4$ | 2-CN-3-Cl—$C_6H_3$ |
| Me | H | $(CH_2)_2Cl$ | Me | H | O | Z = | 2,5-diF—$C_6H_3$ | |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Tables A–D.

Example A

| Wettable Powder | |
|---|---|
| Compound 2 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example B

| Granule | |
|---|---|
| Compound 13 | 10.0% |
| attapulgite granules (low volatile matter, 0.71/0.30 mm; U.S.S. No. 25–50 sieves) | 90.0%. |

Example C

| Extruded Pellet | |
|---|---|
| Compound 80 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example D

| Emulsifiable Concentrate | |
|---|---|
| Compound 2 | 20.0% |
| blend of oil soluble sulfonates and polyoxyethylene ethers | 10.0% |
| isophorone | 70.0%. |

The compounds of this invention are useful as plant disease control agents. The present invention therefore further comprises a method for controlling plant diseases caused by fungal plant pathogens comprising applying to the plant or portion thereof to be protected, or to the plant seed or seedling to be protected, an effective amount of a compound of the invention or a fungicidal composition containing said compound. The compounds and compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, vegetable, field, cereal, and fruit crops. These pathogens include *Plasmopara viticola, Phylophthora infestans, Peronospora tabacina, Pseudoperonospora cubensis, Pythium aphanidermatum, Alternaria brassicae, Septoria nodorum, Septoria tritici, Cercosporidium personatum, Cercospora arachidicola, Pseudocercosporella herpotrichoides, Cercospora beticola, Botrytis cinerea, Monilinia fructicola, Pyricularia oryzae, Podosphaera leucotricha, Venturia inaequalis, Erysiphe graminis, Uncinula necatur, Puccinia recondita, Puccinia graminis, Hemileia vastatrix, Puccinia striiformis, Puccinia arachidis, Rhizoctonia solani, Sphaerotheca fuliginea, Fusarium oxysporum, Verticillium dahliae, Pythium aphanidermatum, Phytophthora megasperma, Sclerotinia sclerotiorum, Sclerotium rolfsii, Erysiphe polygoni, Pyrenophora teres, Gaeumannomyces graminis, Rynchosporium secalis, Fusarium roseum, Bremia lactucae* and other generea and species closely related to these pathogens.

Compounds of this invention can also be mixed with one or more other insecticides, fungicides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection. Examples of such agricultural protectants with which compounds of this invention can be formulated are: insecticides such as abamectin, acephate, azinphos-methyl, bifenthrin, buprofezin, carbofuran, chlorfenapyr, chlorpyrifos, chlorpyrifos-methyl, cyfluthrin, beta-cyfluthrin, cyhalothrin, lambda-cyhalothrin, deltamethrin, diafenthiuron, diazinon, diflubenzuron, dimethoate, esfenvalerate, fenoxycarb, fenpropathrin, fenvalerate, fipronil, flucythrinate, tau-fluvalinate, fonophos, imidacloprid, isofenphos, malathion, metaldehyde, methamidophos, methidathion, methomyl, methoprene, methoxychlor, methyl 7-chloro-2,5-dihydro-2-[[N-(methoxycarbonyl)-N-[4-(trifluoromethoxy)phenyl]amino]carbonyl]indeno[1,2-e][1,3,4]oxadiazine-4a(3H)-carboxylate (DPX-JW062), monocrotophos, oxamyl, parathion, parathion-methyl, permethrin, phorate, phosalone, phosmet, phosphamidon, pirimicarb, profenofos, rotenone, sulprofos, tebufenozide, tefluthrin, terbufos, tetrachlorvinphos, thiodicarb, tralomethrin, trichlorfon and triflumuron; fungicides such as azoxystrobin, benomyl, blasticidin-S, Bordeaux mixture (tribasic copper sulfate), bromuconazole, captafol, captan, carbendazim, chloroneb, chlorothalonil, copper oxychloride, copper salts, cymoxanil, cyproconazole, cyprodinil (CGA 219417), diclomezine, dicloran, difenoconazole, dimethomorph, diniconazole, diniconazole-M, dodine, edifenphos, epoxiconazole (BAS 480F), famoxadone, fenarimol, fenbuconazole, fenpiclonil, fenpropidin, fenpropimorph, fluazinam, fluquinconazole, flusilazole, flutolanil, flutriafol, folpet, fosetyl-aluminum, furalaxyl, hexaconazole, ipconazole, iprobenfos, iprodione, isoprothiolane, kasugamycin, kresoxim-methyl, mancozeb, maneb, mepronil, metalaxyl, metconazole, S-methyl 7-benzothiazolecarbothioate (CGA 245704), myclobutanil, neo-asozin (ferric methanearsonate), oxadixyl, penconazole, pencycuron, probenazole, prochloraz, propiconazole, pyrifenox, pyroquilon, quinoxyfen, spiroxamine (KWG4168), sulfur, tebuconazole, tetraconazole, thiabendazole, thiophanate-methyl, thiram, triadimefon, triadimnenol, tricyclazole, triticonazole, validamycin and vinclozolin; nematocides such as aldoxycarb and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thuringiensis, Bacillus thuringiensis* delta endotoxin, baculovirus, and entomopathogenic bacteria, virus and fungi.

In certain instances, combinations with other fungicides having a similar spectrum of control but a different mode of action will be particularly advantageous for resistance management.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to the seed to protect the seed and seedling.

Rates of application for these compounds can be influenced by many factors of the environment and should be determined under actual use conditions. Foliage can normally be protected when treated at a rate of from less than 1 g/ha to 5,000 g/ha of active ingredient. Seed and seedlings can normally be protected when seed is treated at a rate of from 0.1 to 10 g per kilogram of seed.

The following TESTS demonstrate the control efficacy of compounds of this invention on specific pathogens. The pathogen control protection afforded by the compounds is not limited, however, to these species. See Index Tables A–E for compound descriptions. The following abbreviations are used in the Index Tables which follow: t=tertiary, n=normal, i=iso, F=fluorine, Br=bromine, Cl=chlorine, I=iodine, Me=methyl, Et=ethyl, Pr=propyl, Bu=butyl, CF$_3$=trifluoromethyl and CN=cyano. The abbreviation "Ex." stands for "Example" and is followed by a number indicating in which example the compound is prepared. The abbreviation "Config." stands for "Configuration".

INDEX TABLE A

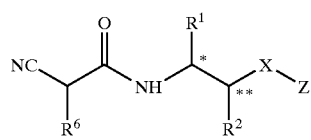

The compounds listed below are mixtures of diastereoisomers unless indicated otherwise.

| Cmpd No. | R¹ | Conf. at * | R² | Conf. at ** | R⁶ | X | Z | mp(° C.) |
|---|---|---|---|---|---|---|---|---|
| 1a | Me | R, S | H | — | t-Bu | O | C₆H₅ | 125–133 |
| 1b# | Me | R, S | H | — | t-Bu | O | C₆H₅ | 132–138 |
| 1c## | Me | R, S | H | — | t-Bu | O | C₆H₅ | 111–114 |
| 1d# | Me | R | H | — | t-Bu | O | C₆H₅ | 78–80 |
| 1e## | Me | R | H | — | t-Bu | O | C₆H₅ | 78–80 |
| 2a | Me | R, S | H | — | t-Bu | O | 2-F—C₆H₄ | Oil* |
| 2b# | Me | R | H | — | t-Bu | O | 2-F—C₆H₄ | Oil* |
| 2c## | Me | R | H | — | t-Bu | O | 2-F—C₆H₄ | 100–102 |
| 3a | Me | R, S | H | — | t-Bu | O | 3-F—C₆H₄ | Oil* |
| 3b# | Me | R, S | H | — | t-Bu | O | 3-F—C₆H₄ | 131–133 |
| 3c## | Me | R, S | H | — | t-Bu | O | 3-F—C₆H₄ | 112–115 |
| 3d# | Me | R | H | — | t-Bu | O | 3-F—C₆H₄ | Oil* |
| 3e## | Me | R | H | — | t-Bu | O | 3-F—C₆H₄ | 96–98 |
| 4a# | Me | R, S | H | — | t-Bu | O | 4-F—C₆H₄ | Oil* |
| 4b## | Me | R, S | H | — | t-Bu | O | 4-F—C₆H₄ | 85–88 |
| 4c | Me | R | H | — | t-Bu | O | 4-F—C₆H₄ | Oil* |
| 5a | Me | R, S | H | — | t-Bu | O | 2-Cl—C₆H₄ | Oil* |
| 5b | Me | R | H | — | t-Bu | O | 2-Cl—C₆H₄ | 104–107 |
| 6a# | Me | R, S | H | — | t-Bu | O | 3-Cl—C₆H₄ | 112–114 |
| 6b | Me | R, S | H | — | t-Bu | O | 3-Cl—C₆H₄ | Oil* |
| 6c## | Me | R, S | H | — | t-Bu | O | 3-Cl—C₆H₄ | 132–135 |
| 6d# | Me | R | H | — | t-Bu | O | 3-Cl—C₆H₄ | Oil* |
| 6e## | Me | R | H | — | t-Bu | O | 3-Cl—C₆H₄ | Oil* |
| 7a# | Me | R, S | H | — | t-Bu | O | 4-Cl—C₆H₄ | Oil* |
| 7b## | Me | R, S | H | — | t-Bu | O | 4-Cl—C₆H₄ | 107–110 |
| 7c# | Me | R | H | — | t-Bu | O | 4-Cl—C₆H₄ | Oil* |
| 7d## | Me | R | H | — | t-Bu | O | 4-Cl—C₆H₄ | Oil* |
| 8a | Me | R, S | H | — | t-Bu | O | 2-Br—C₆H₄ | 123–125 |
| 8b# | Me | R | H | — | t-Bu | O | 2-Br—C₆H₄ | 103–105 |
| 8c## | Me | R | H | — | t-Bu | O | 2-Br—C₆H₄ | 112–114 |
| 9a | Me | R, S | H | — | t-Bu | O | 3-Br—C₆H₄ | Oil* |
| 9b# | Me | R | H | — | t-Bu | O | 3-Br—C₆H₄ | 106–108 |
| 9c## | Me | R | H | — | t-Bu | O | 3-Br—C₆H₄ | Oil* |
| 10a# | Me | R, S | H | — | t-Bu | O | 4-Br—C₆H₄ | Oil* |
| 10b## | Me | R, S | H | — | t-Bu | O | 4-Br—C₆H₄ | Oil* |
| 10c# | Me | R | H | — | t-Bu | O | 4-Br—C₆H₄ | Oil* |
| 10d## | Me | R | H | — | t-Bu | O | 4-Br—C₆H₄ | Oil* |
| 11a | Me | R, S | H | — | t-Bu | O | 2-I—C₆H₄ | 140–142 |

-continued

| Cmpd No. | R¹ | Conf. at * | R² | Conf. at ** | R⁶ | X | Z | mp(° C.) |
|---|---|---|---|---|---|---|---|---|
| 11b | Me | R | H | — | t-Bu | O | 2-I—C₆H₄ | 124–126 |
| 12a# | Me | R | H | — | t-Bu | O | 3-I—C₆H₄ | Oil* |
| 12b## | Me | R | H | — | t-Bu | O | 3-I—C₆H₄ | Oil* |
| 13a | Me | R, S | H | — | t-Bu | O | 2-CN—C₆H₄ | Oil* |
| 13b# | Me | R | H | — | t-Bu | O | 2-CN—C₆H₄ | Oil* |
| 13c# | Me | R | H | — | t-Bu | O | 2-CN—C₆H₄ | Oil* |
| 14a# | Me | R | H | — | t-Bu | O | 2-Cl-4-Me—C₆H₃ | Oil* |
| 14b## | Me | R | H | — | t-Bu | O | 2-Cl-4-Me—C₆H₃ | Oil* |
| 15a# | Me | R | H | — | t-Bu | O | 2-Cl-5-Me—C₆H₃ | 103–106 |
| 15b## | Me | R | H | — | t-Bu | O | 2-Cl-5-Me—C₆H₃ | 112–115 |
| 16 | Me | R | H | — | t-Bu | O | 2-(CH₂CN)—C₆H₄ | 120–122 |
| 17a | Me | R, S | H | — | t-Bu | O | 2-CF₃—C₆H₄ | 92–94 |
| 17b | Me | R | H | — | t-Bu | O | 2-CF₃—C₆H₄ | 92–94 |
| 18a# | Me | R | H | — | t-Bu | O | 3-CF₃—C₆H₄ | Oil* |
| 18b## | Me | R | H | — | t-Bu | O | 3-CF₃—C₆H₄ | 98–100 |
| 19 | Me | R | H | — | t-Bu | O | 2-Me—C₆H₄ | 104–107 |
| 20a Ex. 6 | Me | R, S | H | — | t-Bu | O | 2-Et—C₆H₄ | 94–97 |
| 20b | Me | R | H | — | t-Bu | O | 2-Et—C₆H₄ | 102–104 |
| 21a | Me | R, S | H | — | t-Bu | O | 2-n-Pr—C₆H₄ | 95–97 |
| 21b | Me | R | H | — | t-Bu | O | 2-n-Pr—C₆H₄ | 78–81 |
| 22 | Me | R | H | — | t-Bu | O | 2-i-Pr—C₆H₄ | 112–114 |
| 23 | Me | R | H | — | t-Bu | O | 2-t-Bu—C₆H₄ | Oil* |
| 24 | Me | R | H | — | t-Bu | O | 4-t-Bu—C₆H₄ | 97–100 |
| 25a | Me | R, S | H | — | t-Bu | O | 2-(CH₂CH=CH₂)—C₆H₄ | Oil* |
| 25b | Me | R | H | — | t-Bu | O | 2-(CH₂CH=CH₂)—C₆H₄ | 70–72 |
| 26a# | Me | R | H | — | t-Bu | O | 2,3-diF—C₆H₃ | 86–88 |
| 26b## | Me | R | H | — | t-Bu | O | 2,3-diF—C₆H₃ | 120–122 |
| 27a# | Me | R | H | — | t-Bu | O | 2,4-diF—C₆H₃ | Oil* |
| 27b## | Me | R | H | — | t-Bu | O | 2,4-diF—C₆H₃ | Oil* |
| 28a# | Me | R | H | — | t-Bu | O | 2,5-diF—C₆H₃ | 104–106 |
| 28b## | Me | R | H | — | t-Bu | O | 2,5-diF—C₆H₃ | Oil* |
| 28c | Me | R | H | — | t-Bu | O | 2,5-diF—C₆H₃ | 101–103 |
| 29a | Me | R, S | H | — | t-Bu | O | 2,6-diF—C₆H₃ | Oil* |
| 29b | Me | R | H | — | t-Bu | O | 2,6-diF—C₆H₃ | Oil* |
| 30a# | Me | R | H | — | t-Bu | O | 3,4-diF—C₆H₃ | Oil* |
| 30b## | Me | R | H | — | t-Bu | O | 3,4-diF—C₆H₃ | Oil* |
| 31a# | Me | R | H | — | t-Bu | O | 2,3-diCl—C₆H₃ | 122–124 |
| 31b## | Me | R | H | — | t-Bu | O | 2,3-diCl—C₆H₃ | 104–106 |
| 32a# | Me | R | H | — | t-Bu | O | 2,4-diCl—C₆H₃ | Oil* |
| 32b# | Me | R | H | — | t-Bu | O | 2,4-diCl—C₆H₃ | Oil* |
| 33a# | Me | R | H | — | t-Bu | O | 2,5-diCl—C₆H₃ | 103–105 |
| 33b# | Me | R | H | — | t-Bu | O | 2,5-diCl—C₆H₃ | 103–105 |
| 33c | Me | R | H | — | t-Bu | O | 2,5-diCl—C₆H₃ | 110–112 |
| 34 | Me | R | H | — | t-Bu | O | 2,6-diCl—C₆H₃ | 128–130 |
| 35a# | Me | R | H | — | t-Bu | O | 3,5-diCl—C₆H₃ | 135–137 |
| 35b## | Me | R | H | — | t-Bu | O | 3,5-diCl—C₆H₃ | 121–123 |
| 36a# | Me | R | R | — | t-Bu | O | 2-F-4-Cl—C₆H₃ | Oil* |
| 36b## | Me | R | H | — | t-Bu | O | 2-F-4-Cl—C₆H₃ | Oil* |
| 37a# | Me | R | H | — | t-Bu | O | 2-Cl-4-F—C₆H₃ | 88–90 |
| 37b## | Me | R | H | — | t-Bu | O | 2-Cl-4-F—C₆H₃ | Oil* |
| 38 | Me | R, S | H | — | t-Bu | O | 2-F-4-Br—C₆H₃ | Oil* |
| 39 | Me | R, S | H | — | t-Bu | O | 2-CN-3-F—C₆H₃ | 143–149 |
| 40 | Me | R, S | H | — | t-Bu | O | 2-CN-4-F—C₆H₃ | 110–116 |
| 41 | Me | R | H | — | t-Bu | O | 2-CN-5-F—C₆H₃ | Oil* |
| 42 | Me | R, S | H | — | t-Bu | O | 2-CN-3-Cl—C₆H₃ | 115–135 |
| 43 | Me | R | H | — | t-Bu | O | 2-CN-5-Cl—C₆H₃ | Oil* |
| 44 | Me | R | H | — | t-Bu | O | 2-CN-5-Br—C₆H₃ | Oil* |
| 45 | Me | R, S | H | — | t-Bu | O | 2-CN-3-I—C₆H₃ | 53–73 |
| 46 | Me | R | H | — | t-Bu | O | 2-CN-5-I—C₆H₃ | Oil* |
| 47 | Me | R, S | H | — | t-Bu | O | 2-CN-3-CF₃—C₆H₃ | 60–90 |
| 48 | Me | R, S | H | — | t-Bu | O | 2-CF₃-6-CN—C₆H₃ | 135–170 |
| 49 | Me | R, S | H | — | t-Bu | O | 2-Me-3-Cl-5-CN-1H-pyrrol-1-yl | 127–129 |
| 50 | Me | R, S | H | — | t-Bu | O | 2-Me-3-Br-5-CN-1H-pyrrol-1-yl | Oil* |
| 51 | Me | R | H | — | t-Bu | O | 2,3-diCl-5-CN-1H-pyrrol-1-yl | 110–116 |
| 52 | Me | R | H | — | t-Bu | O | 2,3,4-triCl-5-CN-1H-pyrrol-1-yl | 110–116 |
| 53 | Me | R, S | H | — | t-Bu | CH₂ | 3-Cl-5-CN-1H-pyrrol-1-yl | 75–106 |
| 54# | H | — | H | — | t-Bu | CH₂ | C₆H₅ | 93–96 |

-continued

| Cmpd No. | R¹ | Conf. at * | R² | Conf. at ** | R⁶ | X | Z | mp(° C.) |
|---|---|---|---|---|---|---|---|---|
| 55# | H | — | H | — | t-Bu | $CH_2$ | 2,3-diCl-5-CN-1H-pyrrol-1-yl | Oil* |
| 56 | Me | R | H | — | CH(Me)C(Me)₃ | O | $C_6H_5$ | Oil* |
| 57 | Me | R | H | — | CH(Me)C(Me)₃ | O | 2-F—$C_6H_4$ | Oil* |
| 58 | Me | R | H | — | CH(Me)C(Me)₃ | O | 2-Cl—$C_6H_4$ | Oil* |
| 59 | Me | R | H | — | CH(Me)C(Me)₃ | O | 2-Br—$C_6H_4$ | Oil* |
| 60 | Me | R | H | — | CH(Me)C(Me)₃ | O | 2-CN—$C_6H_4$ | Oil* |
| 61 | Me | R | H | — | CH(Me)C(Me)₃ | O | 2-($CH_2CN$)—$C_6H_4$ | Oil* |
| 62 | Me | R | H | — | CH(Me)C(Me)₃ | O | 2,5-diCl—$C_6H_3$ | Oil* |
| 63 | Me | R, S | H | — | CH(Me)C(Me)₃ | O | 2-CN-3-F—$C_6H_3$ | Oil* |
| 64 | Me | R, S | H | — | CH(Me)C(Me)₃ | O | 2-CN-3-Cl—$C_6H_3$ | Oil* |
| 65 | Me | R, S | H | — | CH(Me)C(Me)₃ | O | 2-CN-3-I—$C_6H_3$ | Oil* |
| 66 | Me | R, S | H | — | CH(Me)C(Me)₃ | O | 2-CN-3-$CF_3$—$C_6H_3$ | Oil* |
| 67 | Me | R, S | H | — | CH(Me)C(Me)₃ | O | 2-F-6-CN—$C_6H_3$ | 147–165 |
| 68 | Me | R, S | H | — | CH(Me)C(Me)₃ | O | 2-$CF_3$—6—CN—$C_6H_3$ | Oil* |
| 69 | Me | R, S | H | — | CH(Me)C(Me)₃ | O | 2-CN-3,5-diF—$C_6H_2$ | Oil* |
| 70 | Me | R, S | H | — | CH(Me)C(Me)₃ | O | 2-Me-3-Br-5-CN-1H-pyrrol-1-yl | Oil* |
| 71a | Me | R, S | H | — | CH(Me)C(Me)₃ | O | 2-Me-3-Cl-5-CN-1H-pyrrol-1-yl | Oil* |
| 71b | Me | R, S | H | — | CH(Me)C(Me)₃ | O | 2-Me-3-Cl-5-CN-1H-pyrrol-1-yl | Oil* |
| 72 | Me | R, S | H | — | CH(Me)C(Me)₃ | $CH_2$ | 2-Me-3-Cl-5-CN-1H-pyrrol-1-yl | 111–118 |
| Ex.4 | | | | | | | | |
| 73 | Me | R, S | H | — | CH(Me)C(Me)₃ | $CH_2$ | 2-Me-3-Br-5-CN-1H-pyrrol-1-yl | Oil* |
| 74 | Me | R, S | H | — | CH(Me)C(Me)₃ | $CH_2$ | 3-Cl-5-CN-1H-pyrrol-1-yl | Oil* |
| 165a# | Me | R | H | — | t-Bu | O | 2-Br-4-F—$C_6H_3$ | 95–98 |
| 165b## | Me | R | H | — | t-Bu | O | 2-Br-4-F—$C_6H_3$ | Oil* |
| 166a# | Me | R | H | — | t-Bu | O | 2-Br-5-F—$C_6H_3$ | 95–98 |
| 166b## | Me | R | H | — | t-Bu | O | 2-Br-5-F—$C_6H_3$ | 77–80 |
| 168a# | Me | R | H | — | t-Bu | O | 2,3,5-triF—$C_6H_2$ | 111–114 |
| 168b## | Me | R | H | — | t-Bu | O | 2,3,5-triF—$C_6H_2$ | 116–119 |
| 169a# | Me | R | H | — | t-Bu | O | 2-Cl-3,5-diF—$C_6H_2$ | 109–112 |
| 169b## | Me | R | H | — | t-Bu | O | 2-Cl-3,5-diF—$C_6H_2$ | Oil* |
| 170a# | Me | R | H | — | t-Bu | O | 2,3,5-triCl—$C_6H_2$ | Oil* |
| 170b## | Me | R | H | — | t-Bu | O | 2,3,5-triCl—$C_6H_2$ | 109–112 |
| 171a# | Me | R | H | — | t-Bu | O | 2,3,6-triCl—$C_6H_2$ | Oil* |
| 171b## | Me | R | H | — | t-Bu | O | 2,3,6-triCl—$C_6H_2$ | Oil* |
| 172 | Me | R | H | — | t-Bu | O | 2,4,6-triCl—$C_6H_2$ | 81–83 |
| 173a# | Me | R | H | — | t-Bu | O | 4-Cl-2,5-diF—$C_6H_2$ | 93–95 |
| 173b## | Me | R | H | — | t-Bu | O | 4-Cl-2,5-diF—$C_6H_2$ | 112–115 |
| 174a# | Me | R | H | — | t-Bu | O | 2,4,5-triCl—$C_6H_2$ | Oil* |
| 174b## | Me | R | H | — | t-Bu | O | 2,4,5-triCl—$C_6H_2$ | 139–142 |
| 175 | Me | R, S | H | — | t-Bu | O | 2-($CH_2F$)—$C_6H_4$ | 139–142 |
| 176 | Me | R | H | — | t-Bu | O | 3-Me—$C_6H_4$ | Oil* |
| 177 | Me | R | H | — | t-Bu | O | 3-Et—$C_6H_4$ | Oil* |
| 181a# | Me | R | H | — | t-Bu | O | 3,4-diCl—$C_6H_3$ | Oil* |
| 181b## | Me | R | H | — | t-Bu | O | 3,4-diCl—$C_6H_3$ | Oil* |
| 182a# | Me | R | H | — | t-Bu | O | 3-F-4-Cl—$C_6H_3$ | Oil* |
| 182b## | Me | R | H | — | t-Bu | O | 3-F-4-Cl—$C_6H_3$ | Oil* |
| 183a# | Me | R | H | — | t-Bu | O | 3-Cl-4-F—$C_6H_3$ | Oil* |
| 183b## | Me | R | H | — | t-Bu | O | 3-Cl-4-F—$C_6H_3$ | 85–88 |
| 184a# | Me | R | H | — | t-Bu | O | 3,5-diF—$C_6H_3$ | 123–126 |
| 184b## | Me | R | H | — | t-Bu | O | 3,5-diF—$C_6H_3$ | 85–88 |
| 185 | Me | R | H | — | t-Bu | O | 2-($CH_2CH=CH_2$)-4-Me—$C_6H_3$ | 84–86 |
| 186 | Me | R | H | — | t-Bu | O | 2,3,6-triF—$C_6H_2$ | Oil* |
| 187a# | Me | R | H | — | t-Bu | O | 2-Br-3,4-diF—$C_6H_2$ | 115–118 |
| 187b## | Me | R | H | — | t-Bu | O | 2-Br-3,4-diF—$C_6H_2$ | Oil* |
| 188a# | Me | R | H | — | t-Bu | O | 2,4,5-triF—$C_6H_2$ | Oil** |
| 188b## | Me | R | H | — | r-Bu | O | 2,4,5-triF—$C_6H_2$ | Oil* |
| 189a# | Me | R | H | — | t-Bu | O | 2,4,6-triF—$C_6H_2$ | 76-79 |
| 189b## | Me | R | H | — | t-Bu | O | 2,4,6-triF—$C_6H_2$ | Oil* |
| 190a# | Me | R | H | — | t-Bu | O | 2,3,4-triF—$C_6H_2$ | Oil* |
| 190b## | Me | R | H | — | t-Bu | O | 2,3,4-triF—$C_6H_2$ | Oil* |
| 191a# | Me | R | H | — | t-Bu | O | 2-Cl-5-F—$C_6H_3$ | Oil* |
| 191b## | Me | R | H | — | t-Bu | O | 2-Cl-5-F—$C_6H_3$ | Oil* |
| 191c | Me | R | H | — | t-Bu | O | 2-Cl-5-F—$C_6H_3$ | Oil* |
| 192a# | Me | R | H | — | $C(Me)_2CH=CH_2$ | O | 2-Cl-5-F—$C_6H_3$ | 79–81 |
| 192b## | Me | R | H | — | $C(Me)_2CH=CH_2$ | O | 2-Cl-5-F—$C_6H_3$ | Oil* |
| 193 | Me | R | H | — | $C(Me)_2C\equiv CH$ | O | 2-Cl-5-F—$C_6H_3$ | 99–102 |
| 194 | Me | R | H | — | CH(Me)C(Me)₃ | O | 2-Cl-5-F—$C_6H_3$ | 99–102 |
| 195 | Me | R | H | — | t-Bu | O | 2,3,5,6-tetraF—$C_6H$ | 81–83 |
| 196 | Me | R | H | — | t-Bu | O | 2,6-diBr-4-F—$C_6H_2$ | 130–133 |
| 197 | Me | R | H | — | t-Bu | O | 2,6-diCl-4-F—$C_6H_2$ | 120–123 |
| 198a# | Me | R | H | — | t-Bu | O | 2-F-5-Cl—$C_6H_3$ | 101–104 |

-continued

| Cmpd No. | R¹ | Conf. at * | R² | Conf. at ** | R⁶ | X | Z | mp(° C.) |
|---|---|---|---|---|---|---|---|---|
| 198b## | Me | R | H | — | t-Bu | O | 2-F-5-Cl—C₆H₃ | Oil* |
| 199 | Me | R | H | — | CH(Me)C(Me)₃ | O | 2-F-5-Cl—C₆H₃ | Oil* |
| 200a# | Me | R | H | — | C(Me)₂CH=CH₂ | O | 2-F-5-Cl—C₆H₃ | 104–107 |
| 200b## | Me | R | H | — | C(Me)₂CH=CH₂ | O | 2-F-5-Cl—C₆H₃ | Oil* |
| 201 | Me | R,S | H | — | t-Bu | O | 2-(OCF₂CF₂H)—C₆H₄ | Oil* |
| 202 | Me | R,S | H | — | t-Bu | O | 2-(SCF₂CF₂H)—C₆H₄ | 80–110 |
| 203 | Me | R,S | H | — | t-Bu | O | 2-F-6-CN—C₆H₃ | Oil* |
| 204 | Me | R,S | H | — | t-Bu | O | 2-(CH₂CH=CH₂)-6-CN—C₆H₃ | Oil* |
| 205 | Me | R,S | H | — | t-Bu | O | 2-(CH₂CH₂CH₃)-6-CN—C₆H₃ | Oil* |
| 206 | Me | R,S | H | — | t-Bu | O | 2-CF₂H-6-CN—C₆H₃ | 93–145 |
| 207 | Me | R,S | H | — | t-Bu | O | 2-CN-4,5-diF—C₆H₂ | 55–105 |
| 208 | Me | R,S | H | — | t-Bu | O | 2-CN-3,6-diF—C₆H₂ | 113–156 |
| 209 | Me | R,S | H | — | t-Bu | O | 2-CN-6-Me—C₆H₃ | Oil* |
| 210 | Me | R,S | H | — | t-Bu | O | 2-CN-6-Cl—C₆H₃ | 118–150 |
| 211 | Me | R | H | — | C(Me)₂C≡CH | O | 2,5-diF—C₆H₃ | 85–87 |
| 212 | Me | R | H | — | C(Me)₂C≡CH | O | 2,5-diCl—C₆H₃ | 93–97 |
| 213 | Me | R | H | — | C(Me)₂C≡CH | O | 2-Cl-5-Me—C₆H₃ | 84–86 |
| 214 | Me | R | H | — | C(Me)₂CH=CH₂ | O | 2,5-diF—C₆H₃ | 107–112 |
| 215a# | Me | R | H | — | C(Me)₂CH=CH₂ | O | 2,5-diCl—C₆H₃ | 82–110 |
| 215b## | Me | R | H | — | C(Me)₂CH=CH₂ | O | 2,5-diCl—C₆H₃ | Oil* |
| 216 | Me | R,S | H | — | t-Bu | O | 2-(C≡CH)—C₆H₄ | 128–146 |
| 217 | Me | R | H | — | C(Me)₂CF=CH₂ | O | 2,5-diF—C₆H₃ | 106–110 |
| Ex. 7 | | | | | | | | |
| 218 | Me | R | H | — | C(Me)(CH₂F)CH=CH₂ | O | 2,5-diF—C₆H₃ | 70–85 |
| 219 | Me | R | H | — | C(Me)(CH₂F)CH=CH₂ | O | 2,5-diCl—C₆H₃ | Oil* |
| 220 | Me | R | H | — | C(Me)(CH₂F)CH=CH₂ | O | 2-Cl-5-F—C₆H₃ | 73–88 |
| 221a# | Me | R | H | — | C(Me)₂CH=CHF | O | 2,5-diF—C₆H₃ | Oil* |
| 221b## | Me | R | H | — | C(Me)₂CH=CHF | O | 2,5-diF—C₆H₃ | Oil* |
| 222 | Me | R | H | — | C(Me)₂CH=CHF | O | 2-Cl-5-F—C₆H₃ | Oil* |
| 223 | Me | R | H | — | C(Me)₂CF=CH₂ | O | 2-Cl-5-F—C₆H₃ | Oil* |
| 224 | Me | R | H | — | C(Me)₂CH=CHF | O | 2-F-5-Cl—C₆H₃ | 78–86 |
| 225 | Me | R | H | — | C(Me)(CH₂F)CH=CHF | O | 2-(OCF₂CF₂H)-5-F—C₆H₃ | Oil* |
| 226 | Me | R | H | — | C(Me)(CH₂F)CH=CHF | O | 2-F-5-Me—C₆H₃ | 70–81 |
| 227 | Me | R | H | — | C(Me)(CH₂F)CH=CHF | O | 2-Cl-5-Me—C₆H₃ | Oil* |
| 320 | Me | R | H | — | C(Me)₂C≡CH | O | 2-F-5-Cl—C₆H₃ | 98–101 |
| 275 | Me | R,S | H | — | CH(Me)C(Me)₃ | O | 2-(CH₂CH=CH₂)-6-CN—C₆H₃ | Oil* |
| 276 | Me | R,S | H | — | CH(Me)C(Me)₃ | O | 2-(CH₂CH₂CH₃)-6-CN—C₆H₃ | Oil* |
| 277 | Me | R,S | H | — | CH(Me)C(Me)₃ | O | 2-CN-5-(OCF₂H)-C₆H₃ | Oil* |
| 278 | Me | R,S | H | — | CH(Me)C(Me)₃ | O | 2-CN-4,5-diF—C₆H₂ | Oil* |
| 279 | Me | R,S | H | — | CH(Me)C(Me)₃ | O | 2-CN-3,6-diF—C₆H₂ | Oil* |
| 280 | Me | R,S | H | — | CH(Me)C(Me)₃ | O | 2-CN-6-Me—C₆H₃ | Oil* |
| 281 | Me | R,S | H | — | CH(Me)C(Me)₃ | O | 2-CN-6-Cl—C₆H₃ | Oil* |
| 282 | Me | R | H | — | CH(Me)₂CH=CH₂ | O | 2-F-5-Me—C₆H₃ | 102–108 |
| 283 | Me | R | C₆H₅ | S | CH₂CH=CH₂ | O | 2,5-diF—C₆H₃ | Oil* |
| 284 | Me | R | C₆H₅ | S | CH₂CH=CH₂ | O | 2-CN-5-F—C₆H₃ | Oil* |
| 285 | Me | R | C₆H₅ | S | CH₂CH=CH₂ | O | 2-CN—C₆H₄ | Oil* |
| 286 | Me | R | C₆H₅ | S | CH₂CH₃ | O | 2-CN-5-F—C₆H₃ | Oil* |
| 287 | Me | R | C₆H₅ | S | CH₂CH₂CH₃ | O | 2-CN-5-F—C₆H₃ | Oil* |
| 288 | Me | R | C₆H₅ | S | CH₂CH₂CH₃ | O | 2-CN—C₆H₄ | Oil* |
| 289 | Me | R | C₆H₅ | S | CH(CH₃)₂ | O | 2-CN-5-F—C₆H₃ | Oil* |
| 290 | Me | R | C₆H₅ | S | CH(CH₃)₂ | O | 2-CN—C₆H₄ | Oil* |
| 291 | Me | R | C₆H₅ | S | C(CH₃)₃ | O | 2-CN—C₆H₄ | Oil* |
| 292 | Me | R | H | — | C(CH₃)₃ | O | 2-(OCF₂H)-5-F—C₆H₃ | Oil* |
| 293 | Me | R | C₆H₅ | R | CH₂CH | O | 2,5-diF—C₆H₃ | |
| 294 | Me | R | H | — | CH(Me)₂CH=CH₂ | O | 2-(OCF₂H)-5-F—C₆H₃ | Oil* |
| 295 | Me | R | H | — | C(Me)₂C≡CH | O | 2-(OCF₂H)-5-F—C₆H₃ | Oil* |
| 296 | Me | R | H | — | CH(Me)(Et)CH=CH₂ | O | 2,5-diF—C₆H₃ | 96–106 |
| 297 | Me | R | H | — | CH(Me)(Et)CH=CH₂ | O | 2-F-5-Cl—C₆H₃ | Oil* |
| 298 | Me | R | H | — | CH(Me)(Et)CH=CH₂ | O | 2-Cl-5-F—C₆H₃ | 93–104 |
| 299 | Me | R | H | — | CH(Me)₂CF=CH₂ | O | 2-F-5-Cl—C₆H₃ | 115–123 |
| 300 | Me | R | H | — | CH(Me)₂CF=CH₂ | O | 2,5-diCl—C₆H₃ | 94–99 |
| 301 | Me | R | H | — | CH(Me)(C≡CH)CH=CH₂ | O | 2,5-diF—C₆H₃ | 84–92 |
| 302 | Me | R | H | — | CH(Me)(C≡CH)CH=CH₂ | O | 2-F-5-Cl—C₆H₃ | Oil* |
| 303 | Me | R | H | — | CH(Me)(C≡CH)CH=CH₂ | O | 2-Cl-5-F—C₆H₃ | 60–83 |
| 304 | Me | R | C₆H₅ | R | CH₂CH₃ | O | 2-CN—C₆H₄ | Oil* |
| 305 | Me | R | H | — | t-Bu | O | 2-CN-5-t-Bu—C₆H₃ | Oil* |
| 306 | Me | R | H | — | t-Bu | O | 2-CH(Me)(Et)—C₆H₄ | Oil* |

*See Index Table E for ¹H NMR data.
Single diastereomer A.
Single diastereomer B.

INDEX TABLE B

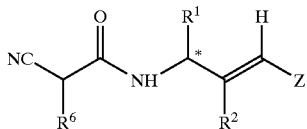

The compounds listed below are mixtures of diastereoisomers unless indicated otherwise.

| Cmpd No# | R¹ | Configuration at* | R⁶ | Z | mp (° C.) |
|---|---|---|---|---|---|
| 75 | H | — | CH(Me)C(Me)₃ | 2-F—C₆H₄ | Oil* |
| 76 | H | — | CH(Me)C(Me)₃ | 3-Br—C₆H₄ | Oil* |
| 167 | H | — | t-Bu | C₆H₅ | 144–147 |
| 178 | H | — | t-Bu | 2-F—C₆H₄ | 114–117 |
| 179 | H | — | t-Bu | 2-Cl—C₆H₄ | 105–108 |
| 180 | H | — | t-Bu | 3-Cl—C₆H₄ | 112–115 |
| 228 | Me | R, S | t-Bu | C₆H₅ | Oil* |
| 229a# | Me | R | t-Bu | 2,5-diF—C₆H₃ | Oil* |
| 229b## | Me | R | t-Bu | 2,5-diF—C₆H₃ | Oil* |
| 272 | H | — | t-Bu | 3-Br—C₆H₄ | 112–115 |
| 273 | H | — | t-Bu | 2,4-diF—C₆H₃ | 122–125 |
| 274 | H | — | t-Bu | 2,4-diCl—C₆H₃ | 83–86 |
| 307 | Me | R | t-Bu | 2-CN—C₆H₄ | Oil* |
| 308 | Me | R | t-Bu | 2-F—C₆H₄ | Oil* |
| 309 | Me | R | t-Bu | 2,4-diF—C₆H₃ | Oil* |

*See Index Table E for ¹H NMR data.
Single diastereomer A.
Single diastereomer B.

INDEX TABLE C

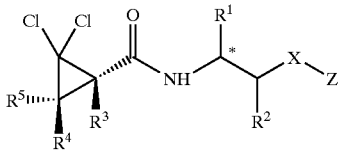

The compounds listed below are mixtures of diastereoisomers unless indicated otherwise.

| Cmpd No | R¹ | Config. at * | R² | R³ | R⁴ | R⁵ | X | Z | mp (° C.) |
|---|---|---|---|---|---|---|---|---|---|
| 77a | Me | R, S | H | Et | Me | H | O | C₆H₅ | 95–99 |
| 77b | Me | R | H | Et | Me | H | O | C₆H₅ | 94–96 |
| 78a | Me | R, S | H | Et | Me | H | O | 2-F—C₆H₄ | 94–96 |
| 78b | Me | R | H | Et | Me | H | O | 2-F—C₆H₄ | 77–79 |
| 79a | Me | R, S | H | Et | Me | H | O | 3-F—C₆H₄ | 110–113 |
| 79b | Me | R | H | Et | Me | H | O | 3-F—C₆H₄ | 86–88 |
| 80a | Me | R, S | H | Et | Me | H | O | 4-F—C₆H₄ | 104–107 |
| 80b | Me | R | H | Et | Me | H | O | 4-F—C₆H₄ | Oil* |
| 81a | Me | R, S | H | Et | Me | H | O | 2-Cl—C₆H₄ | 114–117 |

-continued

| Cmpd No | R¹ | Config. at * | R² | R³ | R⁴ | R⁵ | X | Z | mp (° C.) |
|---|---|---|---|---|---|---|---|---|---|
| 81b | Me | R | H | Et | Me | H | O | 2-Cl—C₆H₄ | 96–98 |
| 82a | Me | R, S | H | Et | Me | H | O | 3-Cl—C₆H₄ | 118–121 |
| 82b | Me | R | H | Et | Me | H | O | 3-Cl—C₆H₄ | Oil* |
| 83a | Me | R, S | H | Et | Me | H | O | 4-Cl—C₆H₄ | 121–124 |
| 83b | Me | R | H | Et | Me | H | O | 4-Cl—C₆H₄ | 77–79 |
| 84a | Me | R, S | H | Et | Me | H | O | 2-Br—C₆H₄ | 124–126 |
| 84b | Me | R | H | Et | Me | H | O | 2-Br—C₆H₄ | Oil* |
| 85a | Me | R, S | H | Et | Me | H | O | 3-Br—C₆H₄ | 83–86 |
| 85b | Me | R | H | Et | Me | H | O | 3-Br—C₆H₄ | Oil* |
| 86a | Me | R, S | H | Et | Me | H | O | 4-Br—C₆H₄ | 124–127 |
| 86b | Me | R | H | Et | Me | H | O | 4-Br—C₆H₄ | 102–104 |
| 87a | Me | R, S | H | Et | Me | H | O | 2-I—C₆H₄ | 108–111 |
| 87b | Me | R | H | Et | Me | H | O | 2-I—C₆H₄ | Oil* |
| 88 | Me | R | H | Et | Me | H | O | 3-I—C₆H₄ | 75–77 |
| 89a | Me | R, S | H | Et | Me | H | O | 2-CN—C₆H₄ | 134–136 |
| 89b | Me | R | H | Et | Me | H | O | 2-CN—C₆H₄ | Oil* |
| 90 | Me | R, S | H | Et | Me | H | O | 2-(OCF₂CF₂H)—C₆H₄ | 90–98 |
| 91 | Me | R, S | H | Et | Me | H | O | 2-(SCF₂CF₂H)—C₆H₄ | 61–76 |
| 92 | Me | R, S | H | Et | Me | H | O | 2-CH₂F—C₆H₄ | 105–107 |
| 93 | Me | R, S | H | Et | Me | H | O | 3-CH₂F—C₆H₄ | 123–125 |
| 94a | Me | R, S | H | Et | Me | H | O | 2-CF₃—C₆H₄ | 131–132 |
| 94b | Me | R | H | Et | Me | H | O | 2-CF₃—C₆H₄ | Oil* |
| 95 | Me | R | H | Et | Me | H | O | 2-Me—C₆H₄ | Oil* |
| 96 | Me | R | H | Et | Me | H | O | 3-Me—C₆H₄ | 80–82 |
| 97a | Me | R, S | H | Et | Me | H | O | 2-Et—C₆H₄ | 102–105 |
| 97b | Me | R | H | Et | Me | H | O | 2-Et—C₆H₄ | Oil* |
| 98a | Me | R, S | H | Et | Me | H | O | 2-n-Pr—C₆H₄ | 90–92 |
| 98b | Me | R | H | Et | Me | H | O | 2-n-Pr—C₆H₄ | Oil* |
| 99 | Me | R | H | Et | Me | H | O | 2-i-Pr—C₆H₄ | Oil* |
| 100 | Me | R | H | Et | Me | H | O | 2-t-Bu—C₆H₄ | Oil* |
| 101a | Me | R, S | H | Et | Me | H | O | 2-(CH₂CH=CH₂)—C₆H₄ | 90–92 |
| 101b | Me | R | H | Et | Me | H | O | 2-(CH₂CH=CH₂)—C₆H₄ | Oil* |
| 102 | Me | R, S | H | Et | Me | H | O | 3-CH₂F—C₆H₄ | 105–107 |
| 103 | Me | R | H | Et | Me | H | O | 2-(CH₂CN)—C₆H₄ | Oil* |
| 104 | Me | R | H | Et | Me | H | O | 2,3-diF—C₆H₃ | 95–97 |
| 105a | Me | R, S | H | Et | Me | H | O | 2,6-diF—C₆H₃ | 95–97 |
| 105b | Me | R | H | Et | Me | H | O | 2,6-diF—C₆H₃ | Oil* |
| 106 | Me | R | H | Et | Me | H | O | 2,4-diF—C₆H₃ | Oil* |
| 107 | Me | R | H | Et | Me | H | O | 2,5-diF—C₆H₃ | 67–72 |
| 108 | Me | R | H | Et | Me | H | O | 3,4-diF—C₆H₃ | Oil* |
| 109 | Me | R | H | Et | Me | H | O | 2,3,5-triF—C₆H₂ | 86–88 |
| 110 | Me | R | H | Et | Me | H | O | 2,4,5-triF—C₆H₂ | 69–71 |
| 111 | Me | R | H | Et | Me | H | O | 2,3-diCl—C₆H₃ | 87–89 |
| 112 | Me | R | H | Et | Me | H | O | 2,4-diCl—C₆H₃ | 70–72 |
| 113 | Me | R | H | Et | Me | H | O | 2,5-diCl—C₆H₃ | 93–95 |
| 114 | Me | R | H | Et | Me | H | O | 2,6-diCl—C₆H₃ | 87–89 |
| 115 | Me | R | H | Et | Me | H | O | 3,5-diCl—C₆H₃ | 87–89 |
| 116 | Me | R | H | Et | Me | H | O | 2,3,5-triCl—C₆H₂ | 94–96 |
| 117 | Me | R | H | Et | Me | H | O | 2,3,6-triCl—C₆H₂ | 95–97 |
| 118 | Me | R | H | Et | Me | H | O | 2,4,6-triCl—C₆H₂ | 118–121 |
| 119 | Me | R | H | Et | Me | H | O | 2-(CH₂CH=CH₂)-6-Me—C₆H₃ | Oil* |
| 120 | Me | R | H | Et | Me | H | O | 2-F-4-Cl—C₆H₃ | Oil* |
| 121 | Me | R | H | Et | Me | H | O | 2-Cl-4-F—C₆H₃ | 65–67 |
| 122 | Me | R, S | H | Et | Me | H | O | 2-F-4-Br—C₆H₃ | 107–109 |
| 123 | Me | R | H | Et | Me | H | O | 2-Cl-3,5-diF—C₆H₂ | 84–86 |
| 124 | Me | R | H | Et | Me | H | O | 2-Br-4-F—C₆H₃ | 62–64 |
| 125 | Me | R | H | Et | Me | H | O | 2-Br-5-F—C₆H₃ | 73–75 |
| 126 | Me | R | H | Et | Me | H | O | 2-Cl-4-Me—C₆H₃ | 73–74 |
| 127 | Me | R | H | Et | Me | H | O | 2-Cl-5-Me—C₆H₃ | 102–104 |
| 128 | Me | R, S | H | Et | Me | H | O | 2-F-6-CN—C₆H₃ | 102–106 |
| 129 | Me | R, S | H | Et | Me | H | O | 2-CN-4-F—C₆H₃ | 119–123 |
| Ex.3 | | | | | | | | | |
| 130 | Me | R, S | H | Et | Me | H | O | 2-CN-3-F—C₆H₃ | 143–149 |
| 131 | Me | R, S | H | Et | Me | H | O | 2-CN-3-Cl—C₆H₃ | 120–122 |
| 132 | Me | R, S | H | Et | Me | H | O | 2-CN-3-I—C₆H₃ | 146–151 |
| 133 | Me | R, S | H | Et | Me | H | O | 2-CN-3-CF₃—C₆H₃ | 120–138 |
| 134 | Me | R, S | H | Et | Me | H | O | 2-CN-6-CF₃—C₆H₃ | 110–134 |
| 135 | Me | R, S | H | Et | Me | H | O | 2-CN-3,5-diF—C₆H₂ | 164–166 |
| 136 | Me | R, S | H | Et | Me | H | O | 2-CN-3,5-diMe-1H-pyrrol-1-yl | Oil* |
| 137 | Me | R, S | H | Et | Me | H | O | 3-Br-5-CN-1H-pyrrol-1-yl | 130–146 |
| 138 | Me | R, S | H | Et | Me | H | O | 3-Cl-5-CN-1H-pyrrol-1-yl | 108–112 |
| 139 | Me | R, S | H | Et | Me | H | O | 2,3-diCl-5-CN-1H-pyrrol-1-yl | Oil* |
| 140a | Me | R, S | H | Et | Me | H | O | 2-Me-3-Cl-5-CN-1H-pyrrol-1-yl | 107–117 |
| 140b | Me | R | H | Et | Me | H | O | 2-Me-3-Cl-5-CN-1H-pyrrol-1-yl | Oil* |

-continued

| Cmpd No | Config. at * | R¹ | R² | R³ | R⁴ | R⁵ | X | Z | mp (° C.) |
|---|---|---|---|---|---|---|---|---|---|
| Ex.2 | | | | | | | | | |
| 141 | Me | R, S | H | Et | Me | H | O | 2-Me-3-Br-5-CN-1H-pyrrol-1-yl | Oil* |
| 142 | Me | R, S | H | Et | Me | H | CH₂ | 2-Me-3-Cl-5-CN-1H-pyrrol-1-yl | 109–115 |
| 143 | Me | R, S | H | Et | Me | H | CH₂ | 2-Me-3-Br-5-CN-1H-pyrrol-1-yl | 123–141 |
| 144 | Me | R, S | H | Et | Me | H | CH₂ | 3-Cl-5-CN-1H-pyrrol-1-yl | Oil* |
| 145# | H | — | H | Et | Me | H | CH₂ | 1H-pyrrol-1-yl | 71–78 |
| 146# | H | — | H | Et | Me | H | CH₂ | 2-Cl-1H-pyrrol-1-yl | 98–100 |
| 147# | H | — | H | Et | Me | H | CH₂ | 2,5-diCl-1H-pyrrol-1-yl | 105–110 |
| 148# | H | — | H | Et | Me | H | CH₂ | 2,3,5-triCl-1H-pyrrol-1-yl | 131–133 |
| 149# | H | — | H | Et | Me | H | CH₂ | 2-CN-1H-pyrrol-1-yl | Oil* |
| 150# | H | — | H | Et | Me | H | CH₂ | 2-CN-3,5-diMe-1H-pyrrol-1-yl | 82–84 |
| 151# | H | — | H | Et | Me | H | CH₂ | 2,3-diCl-5-CN-1H-pyrrol-1-yl | 138–142 |
| 152# | H | — | H | Et | Me | H | CH₂ | 2-Cl-5-CN-1H-pyrrol-1-yl | Oil* |
| 153# | H | — | H | Et | Me | H | O | C₆H₅ | 65–69 |
| 154# | H | — | H | Et | Me | H | CH₂ | C₆H₅ | 93–95 |
| 155# | H | — | H | Et | H | Me | CH₂ | C₆H₅ | 66–70 |
| Ex.1 | | | | | | | | | |
| 230 | Me | R | H | Et | Me | H | O | 3,4-diCl—C₆H₃ | Oil* |
| 231 | Me | R | H | Et | Me | H | O | 3-F-4-Cl—C₆H₃ | Oil* |
| 232 | Me | R | H | Et | Me | H | O | 3-Cl-4-F—C₆H₃ | 77–80 |
| 233 | Me | R | H | Et | Me | H | O | 2,3,6-triF—C₆H₂ | 81–84 |
| 234 | Me | R | H | Et | Me | H | O | 3,5-diF—C₆H₃ | 84–87 |
| 235 | Me | R | H | Et | Me | H | O | 2-Br-4,5-diF—C₆H₂ | Oil* |
| 236 | Me | R | H | Et | Me | H | O | 2,4,5-triF—C₆H₂ | Oil* |
| 237 | Me | R | H | Et | Me | H | O | 2,4,6-triF—C₆H₂ | Oil* |
| 238 | Me | R | H | Et | Me | H | O | 2,3,4-triF—C₆H₂ | Oil* |
| 239 | Me | R | H | Et | Me | H | O | 2-CN-5-Cl—C₆H₃ | Oil* |
| 240 | Me | R | H | Et | Me | H | O | 3-Et—C₆H₄ | Oil* |
| 241 | Me | R | H | Et | Me | H | O | 4-t-Bu—C₆H₄ | Oil* |
| 242 | Me | R | H | Et | Me | H | O | 2,4,5-triCl—C₆H₂ | 80–83 |
| 243 | Me | R | H | Et | Me | H | O | 2,3,4-triCl—C₆H₂ | 82–85 |
| 244 | Me | R, S | H | Et | Me | H | CH₂ | C₆H₅ | 105–108 |
| 245 | Me | R | H | Et | Me | H | O | 2-CN-5-F—C₆H₃ | Oil* |
| 246 | Me | R | H | Et | Me | H | O | 2-CN-5-Br—C₆H₃ | Oil* |
| 247 | Me | R | H | Et | Me | H | O | 2-CN-5-I—C₆H₃ | Oil* |
| 248 | Me | R | H | Et | Me | H | O | 2-CN-5-t-Bu—C₆H₃ | Oil* |
| 249 | Me | R | H | Et | Me | H | O | 2,3,5,6-tetraF—C₆H | 92–95 |
| 250 | Me | R | H | Et | Me | H | O | 2,6-diBr-4-F—C₆H₂ | 88–90 |
| 251 | Me | R | H | Et | Me | H | O | 2,6-diCl-4-F—C₆H₂ | 85–88 |
| 252 | Me | R | H | Et | Me | H | O | 2-F-5-Cl—C₆H₃ | 110–113 |
| 253 | Me | R | H | Et | Me | H | O | 2-Cl-5-F—C₆H₃ | 97–100 |
| 254 | Me | R, S | H | Et | Me | H | O | 2-(CH₂CH=CH₂)-6-CN—C₆H₃ | Oil* |
| 255 | Me | R, S | H | Et | Me | H | O | 2-(CH₂CH₂CH₃)-6-CN—C₆H₃ | Oil* |
| 256 | Me | R, S | H | Et | Me | H | O | 2-CN-5-(OCF₂H)—C₆H₃ | Oil* |
| 257 | Me | R, S | H | Et | Me | H | O | 3,4-diF-6-CN—C₆H₂ | Oil* |
| 258 | Me | R, S | H | Et | Me | H | O | 2,5-diF-6-CN—C₆H₂ | 98–108 |
| 259 | Me | R, S | H | Et | Me | H | O | 2-CN-6-Me—C₆H₃ | 97–114 |
| 260 | Me | R, S | H | Et | Me | H | O | 2-Cl-6-CN—C₆H₃ | 90–92 |
| 310 | Me | R, S | H | Me | Me | H | O | C₆H₅ | 70–75 |
| 311 | Me | R, S | H | Me | H | H | O | C₆H₅ | Oil* |
| 312 | Me | R, S | H | Me | H | H | O | 2-CF₃—C₆H₄ | Oil* |
| 313 | Me | R, S | H | Me | H | H | O | 2-Br—C₆H₄ | Oil* |
| 314 | Me | R, S | H | Me | H | H | O | 2-(CH₂CH=CH₂)—C₆H₄ | Oil* |
| 315 | Me | R, S | H | Me | H | H | O | 2-F—C₆H₄ | Oil* |
| 316 | Me | R, S | H | Et | Me | H | O | 2-CN-6-F—C₆H₃ | 87–94 |
| 317 | Me | R, S | H | Et | Me | H | O | 3-(CH₂F)—C₆H₄ | 123–125 |
| 318 | Me | R | H | Et | Me | H | O | 2-Cl-3,5-diF—C₆H₂ | 84–86 |

*See Index Table E for ¹H NMR data.
Single diastereomer.

INDEX TABLE D

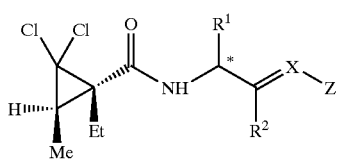

The compounds listed below are mixtures of diastereoisomers unless indicated otherwise.

| Cmpd No | Configuration at * | R¹ | R² | X | Z | mp(° C.) |
|---|---|---|---|---|---|---|
| 156# | H | — | H | CH | C₆H₅ | 109–111 |
| 157# | H | — | H | CH | 2-F—C₆H₄ | 103–105 |

-continued

| Cmpd No | R¹ | Configuration at * | R² | X | Z | mp(° C.) |
|---|---|---|---|---|---|---|
| Ex. 5 | | | | | | |
| 158# | H | — | H | CH | 2-Cl—C₆H₄ | 143–145 |
| 159# | H | — | H | CH | 3-Cl—C₆H₄ | Oil* |
| 160# | H | — | H | CH | 3-Br—C₆H₄ | Oil* |
| 161# | H | — | H | CH | 2-(CH₂CN)—C₆H₄ | Oil* |
| 162# | H | — | H | CH | 2,4-diF—C₆H₃ | Oil* |
| 163# | H | — | H | CH | 2,5-diCl—C₆H₄ | 170–172 |
| 164# | H | — | H | CH | 2-thienyl | 120–122 |
| 261 | Me | R, S | H | CH | 4-F—C₆H₄ | 90–92 |
| 262# | H | — | H | C(Et) | 2,5-diCl—C₆H₃ | Oil* |
| 263 | Me | R, S | H | CH | C₆H₅ | Oil* |
| 264# | H | — | H | CH | 3-F—C₆H₄ | Oil* |
| 265# | H | — | Me | CH | C₆H₅ | Oil* |
| 266 | Me | R | H | CH | 2,4-diCl—C₆H₃ | Oil* |
| 267a# | Me | R | H | CH | 2,5-diF—C₆H₃ | Oil* |

| Cmpd No | R¹ | Configuration at * | R² | X | Z | mp(° C.) |
|---|---|---|---|---|---|---|
| Ex. 8 | | | | | | |
| 267b## | Me | R | H | CH | 2,5-diF—C₆H₃ | 102–105 |
| Ex. 8 | | | | | | |
| 268# | H | — | H | C(Me) | C₆H₅ | Oil* |
| 269# | H | — | H | C(Et) | C₆H₅ | 120–123 |
| 270# | H | — | Me | CH | 2,5-diCl—C₆H₃ | Oil* |
| 271# | H | — | H | C(Me) | 2,5-diCl—C₆H₃ | Oil* |

*See Index Table E for ¹H NMR data.
Single diastereomer A
Single diastereomer B.

INDEX TABLE E

| Cmpd No. | ¹H NMR Data (CDCl₃ solution unless indicated otherwise)[a] |
|---|---|
| 2a | δ 7.10(m, 2H), 6.95(m, 2H), 6.90(dd, 1H), 4.40(m, 1H), 4.08(m, 2H), 1.40(dd, 3H), 1.24(d, 9H) |
| 2b | δ 7.08(m, 2H), 6.95(m, 2H), 6.42(d, 1H), 4.40(m, 1H), 4.05(m, 2H), 3.15(2s, 1H), 1.40(d, 3H), 1.20(2s, 9H) |
| 3a | δ 7.22(m, 1H), 6.65(m, 2H), 6.10(m, 1H), 4.40(m, 1H), 4.05(m, 2H), 3.15(2s, 1H), 1.40(d, 3H), 1.20(2s, 9H) |
| 3d | δ 7.22(m, 1H), 6.65(m, 3H), 6.12(d, 1H), 4.44(m, 1H), 4.00(m, 2H), 3.16(s, 1H), 1.40(d, 3H), 1.20(s, 9H) |
| 4a | δ 7.00(d, 2H), 6.82(d, 2H), 6.18(dd, 1H), 4.40(m, 1H), 3.95(m, 2H), 3.15(2s, 1H), 1.37(d, 3H), 1.20(2s, 9H) |
| 4c | δ 7.00(d, 2H), 6.82(d, 2H), 6.18(dd, 1H), 4.40(m, 1H), 3.95(m, 2H), 3.14(d, 1H), 1.40(d, 3H), 1.20(s, 9H) |
| 5a | δ 7.25(m, 2H), 6.82(m, 2H), 6.15(m, 1H), 4.40(m, 1H), 3.98(m, 2H), 3.15(2s, 1H), 1.40(d, 3H), 1.20(2s, 9H) |
| 6b | δ 7.20(m, 2H), 6.96(d, 2H), 6.90(m, 1H), 6.80(dd, 1H), 6.18(d, 1H) 4.44(m, 1H), 4.00(m, 2H), 3.15(2s, 1H), 1.38(d, 3H), 1.24(2s, 9H) |
| 6d | δ 7.21(t, 2H), 6.98(dd, 2H), 6.90(t, 1H), 6.80(m, 1H), 6.10(dd, 1H) 4.40(m, 1H), 4.00(dd, 1H), 3.96(dd, 1H), 3.15(s, 1H), 1.38(d, 3H), 1.24(s, 9H) |
| 6e | δ 7.21(t, 2H), 6.98(dd, 2H), 6.90(t, 1H), 6.80(m, 1H), 6.18(dd, 1H) 4.40(m, 1H), 3.96(ddd, 2H), 3.13(s, 1H), 1.38(d, 3H), 1.24(s, 9H) |
| 7a | δ 7.22(d, 2H), 6.82(d, 2H), 6.18(d, 1H), 4.40(m, 1H), 3.93(m, 2H), 3.16(s, 1H), 1.37(d, 3H), 1.20(s, 9H) |
| 7c | δ 7.25(d, 2H), 6.80(d, 2H), 6.15(br d, 1H), 4.40(m, 1H), 4.00(dd, 1H), 3.90(dd, 1H), 3.15(s, 1H), 1.40(d, 3H), 1.20(s, 9H) |
| 7d | δ 7.25(d,2H), 6.80(d, 2H), 6.15(br d, 1H), 4.40(m, 1H), 4.00(m, 2H), 3.12(s, 1H), 1.40(d, 3H), 1.20(s, 9H) |
| 9a | δ 7.12(m, 2H), 7.05(m, 1H), 6.80(m, 1H), 6.18(d, 1H), 4.40(m, 1H), 4.00(m, 2H), 3.12(2s, 1H), 1.36(m, 3H), 1.18(2s, 9H) |
| 9c | δ 7.18(m, 2H), 7.08(m, 1H), 6.82(m, 1H), 6.15(dd, 1H), 4.40(m, 1H), 4.00(dd, 2H), 3.12(s, 1H), 1.40(d, 3H), 1.28(s, 9H) |
| 10a | δ 7.40(d, 2H), 6.80(d, 2H), 6.12(d, 1H), 4.40(m, 1H), 3.95(ddd, 2H), 3.15(s, 1H), 1.36(d, 3H), 1.20(s, 9H) |
| 10b | δ 7.40(d, 2H), 6.80(d, 2H), 6.20(d, 1H), 4.40(m, 1H), 3.95(m, 2H), 3.12(s, 1H), 1.36(d, 3H), 1.20(s, 9H) |
| 10c | δ 7.40(d, 2H), 6.80(d, 2H), 6.10(br d, 1H), 4.40(m, 1H), 4.00(dd, 1H), 3.90(dd, 1H), 3.15(s, 1H), 1.40(d 3H), 1.20(s, 9H) |
| 10d | δ 7.40(d, 2H), 6.80(d, 2H), 6.10(br d, 1H), 4.40(m, 1H), 4.00(m, 2H), 3.12(s, 1H), 1.40(d, 3H), 1.20(s, 9H) |
| 12a | δ 7.32(m, 1H), 7.25(m, 1H), 7.02(t, 1H), 6.82(dd, 1H), 6.10(d, 1H), 4.40(m, 1H), 4.40(m, 1H), 4.00(dd, 1H), 3.90(dd, 1H), 3.15(s, 1H), 1.40(d, 3H), 1.20(s, 9H) |
| 12b | δ 7.32(m, 1H), 7.25(m, 1H), 7.02(t, 1H), 6.82(dd, 1H), 6.10(d, 1H), 4.40(m, 1H), 4.40(m, 1H), 4.00(dd, 1H), 3.90(dd, 1H), 3.15(s, 1H), 1.40(d, 3H), 1.20(s, 9H) |
| 13a | δ 7.60(m, 2H), 7.15(M, 1H), 7.02(m, 1H), 6.60(d, 1H), 4.65(dd, 1H), 4.20(m, 2H), 3.21(d, 1H), 1.30(m, 3H), 1.10(d, 9H) |
| 13b | δ 7.57(dt, 2H), 7.05(t, 1H), 7.02(m, 1H), 6.30(d, 1H), 4.41(dd, 1H), 4.10(m, 2H), 3.18(s, 1H), 1.42(m, 3H), 1.18(d, 9H) |
| 13c | δ 7.57(dt, 2H), 7.02(m, 2H), 6.30(d, 1H), 4.41(dd, 1H), 4.10(m, 2H), 3.18(s, 1H), 1.42(m, 3H), 1.18(d, 9H) |
| 14a | δ 7.20(s, 1H), 7.00(d, 1H), 6.80(d, 1H), 6.35(br d, 1H), 4.40(m, 1H), 4.00(m, 2H), 3.14(s, 1H), 2.27(s, 3H), 1.42(d, 3H), 1.20(s, 9H) |

INDEX TABLE E-continued

| Cmpd No. | ¹H NMR Data (CDCl₃ solution unless indicated otherwise)ᵃ |
|---|---|
| 14b | δ 7.20(s, 1H), 7.00(d, 1H), 6.80(d, 1H), 6.40(br d, 1H), 4.40(m, 1H), 4.00(m, 2H), 3.13(s, 1H), 2.27(s, 3H), 1.42(d, 3H), 1.17(s, 9H) |
| 18a | δ 7.60(d, 1H), 7.50(t, 1H), 7.08(t, 1H), 6.97(d, 1H), 6.30(2d, 1H), 4.40(m, 1H), 4.10(m, 2H), 3.11(2s, 1H), 1.38(d, 3H), 1.20(2s, 9H) |
| 23 | δ 7.30(d, 1H), 7.20(t, 1H), 6.92(t, 1H), 6.84(d, 1H), 4.50(m, 1H), 4.05(m, 2H), 3.13(s, 1H), 1.40(m, 12H), 1.20(2s, 9H) |
| 25a | δ 7.20(t, 2H), 6.90(t, 1H), 6.80(d, 1H), 6.20(dd, 1H), 6.00(m, 1H), 5.05(m, 2H), 4.40(m, 1H), 4.00(m, 2H), 3.40(m, 2H), 3.12(2s, 1H), 1.40(d, 3H), 1.20(2s, 9H) |
| 27a | δ 6.90(m, 3H), 6.18(d, 1H) 4.40(m, 1H), 4.05(m, 2H), 3.95(dd, 1H), 3.15(s, 1H), 1.40(d, 3H), 1.20(s, 9H) |
| 27b | δ 6.90(m, 3H), 6.21(d, 1H) 4.40(m, 1H), 4.05(m, 2H), 3.95(dd, 1H), 3.14(s, 1H), 1.40(d, 3H), 1.20(s, 9H) |
| 28b | δ 7.00(m, 1H), 6.70(m, 1H), 6.62(m, 1H), 6.20(d, 1H), 4.40(m, 1H), 4.02(m, 2H), 3.13(s, 1H), 1.40(d, 3H), 1.20(s, 9H) |
| 29a | δ6.95(m, 3H), 6.40(dd, 1H), 4.35(m, 1H), 4.10(m, 2H), 3.17(s, 1H), 1.40(d, 3H), 1.20(s, 9H) |
| 29b | δ 6.95(m, 3H), 6.40(dd, 1H), 4.35(m, 1H), 4.10(m, 2H), 3.17(2s, 1H), 1.40(d, 3H), 1.20(s, 9H) |
| 30a | δ 7.10(dd, 1H), 6.12(m, 1H), 6.60(m, 1H), 6.10(d, 1H), 4.40(m, 1H), 4.00(m, 2H), 3.15(s, 1H), 1.40(d, 3H), 1.20(s, 9H) |
| 30b | δ 7.10(dd, 1H), 6.72(m, 1H), 6.60(m, 1H), 6.15(d, 1H), 4.40(m, 1H), 4.00(m, 2H), 3.13(s, 1H), 1.40(d, 3H), 1.20(s, 9H) |
| 32a | δ 7.39(d, 1H), 7.20(dd, 1H), 6.83(dd, 1H), 6.22(d, 1H), 4.40(m, 1H), 4.02(m, 2H), 3.15(s, 1H), 1.40(d, 3H), 1.20(s, 9H) |
| 32b | δ 7.39(d, 1H), 7.20(dd, 1H), 6.83(dd, 1H), 6.30(d, 1H), 4.40(m, 1H), 4.02(m, 2H), 3.13(s, 1H), 1.40(d, 3H), 1.20(s, 9H) |
| 36a | δ 7.10(d, 1H), 7.05(d, 1H), 6.90(t, 1H), 6.20(d, 1H), 4.40(m, 1H), 4.05(dd, 1H), 3.98(dd, 1H), 3.16(s, 1H), 1.40(d, 3H), 1.20(s, 9H) |
| 36b | δ 7.10(d, 1H), 7.05(d, 1H), 6.90(t, 1H), 6.19(d, 1H), 4.40(m, 1H), 4.05(dd, 1H), 3.98(dd, 1H), 3.12(s, 1H), 1.40(d, 3H), 1.20(s, 9H) |
| 37b | δ 7.15(dd, 1H), 6.90(m, 2H), 6.25(d, 1H) 4.40(m, 1H), 4.02(m, 2H), 3.15(s, 1H), 1.40(d, 3H), 1.17(s, 9H) |
| 38 | δ 7.22(m, 2H), 6.90(m, 1H), 6.20(dd, 1H), 4.40(m, 1H), 4.02(m, 2H), 3.15(d, 1H), 1.40(dd, 3H), 1.17(d, 9H) |
| 41 | δ 7.60(t, 1H), 6.77(m, 2H), 6.20(d, 1H), 4.41(m, 1H), 4.10(m, 2H), 3.15(s, 1H), 1.42(d, 3H), 1.17(s, 9H) |
| 43 | δ 7.50(d, 1H), 7.08(d, 1H), 7.00(s, 1H), 6.20(dd, 1H), 4.41(m, 1H), 4.10(m, 2H), 3.15(s, 1H), 1.42.(d, 3H), 1.17(s, 9H) |
| 44 | δ 7.41(d, 1H), 7.22(d, 1H), 7.17(s, 1H), 6.20(dd, 1H), 4.41(m, 1H), 4.10(m, 2H), 3.15(s, 1H), 1.42(d, 3H), 1.17(s, 9H) |
| 46 | δ 7.41(d, 1H), 7.32(d, 1H), 7.25(s, 1H), 6.18(dd, 1H), 4.41(m, 1H), 4.10(m, 2H), 3.15(2s, 1H), 1.42(d, 3H), 1.17(s, 9H) |
| 50 | δ 6.60(s, 1H), 6.20(d, 1H), 4.14(m, 1H), 4.25(d, 2H), 3.20(s, 3H), 1.40(d, 3H), 1.20(s, 9H) |
| 55 | δ 6.80(s, 1H), 6.30(br s, 1H), 4.15(t, 2H), 3.35(q, 2H), 3.15(s, 1H), 2.00(m, 2H), 1.20(s, 9H) |
| 56 | δ 7.30(m, 4H), 6.95(m, 3H), 6.60(dd, 1H), 4.40(m, 1H), 4.02(m, 2H), 3.60(d, 1H), 2.20(m, 1H), 1.40(m, 3H), 1.00(m, 12H) |
| 57 | δ 7.00(m, 4H), 6.60(m, 1H), 4.40(m, 1H), 4.02(m, 2H), 3.60(d, 1H), 2.20(m, 1H), 1.40(m, 3H), 1.05(m, 12H) |
| 58 | δ 7.40(m, 1H), 7.20(t, 1H), 6.95(m, 2H), 6.63(br s, 1H), 4.42(m, 1H), 4.04(m, 2H), 3.60(d, 1H), 2.20(m, 1H), 1.40(d, 3H), 1.00(m, 12H) |
| 59 | δ 7.57(m, 1H), 7.30(t, 1H), 6.90(m, 2H), 6.70(br s, 1H), 4.40(m, 1H), 4.05(m, 2H), 3.60(d, 1H), 2.20(m, 1H), 1.40(m, 3H), 1.00(m, 12H) |
| 60 | δ 7.80(m, 1H), 7.50(m, 2H), 7.00(m, 1H), 6.60(d, 1H), 4.40(m, 1H), 4.07(m, 2H), 3.60(d, 1H), 2.18(m, 1H), 1.40(m, 3H), 1.20(m, 3H), 1.00(m, 9H) |
| 61 | δ 7.30(d, 1H), 6.90(m, 2H), 6.60(d, 1H), 4.40(m, 1H), 4.03(m, 2H), 3.60(d, 1H), 2.20(m, 1H), 1.40(m, 3H), 1.00(m, 12H) |
| 62 | δ 7.30(d, 2H), 7.00(t, 1H), 6.90(m, 1H), 6.63(d, 1H), 4.44(m, 1H), 4.05(m, 2H), 3.70(s, 2H), 3.60(d, 1H), 2.20(m, 1H), 1.40(d, 3H), 1.00(m, 12H) |
| 63 | δ 7.50(m, 1H), 6.80(m, 2H), 6.75(m, 1H), 4.40(m, 1H), 4.15(m, 2H), 3.75(s, 1H), 3.35(m, 1H), 3.60(d, 1H), 2.20(m, 1H), 1.45(d, 3H), 1.10(m, 3H), 1.00(s, 9H) |
| 64 | δ 7.45(t, 1H), 7.1(d, 1H), 6.4(m, 1H), 6.1(s, 1H), 4.4(m, 1H), 4.1(m, 2H), 3.3(m, 2H), 2.2(m, 1H), 1.41(d, 3H), 1.0(s, 9H) |
| 65 | δ 7.50(d, 1H), 7.20(t, 1H), 6.95(m, 1H), 6.40(br s, 1H), 4.40(m, 1H), 4.10(m, 2H), 3.50(m, 1H), 2.10(m, 1H), 1.40(dd, 3H), 1.15(m, 3H), 1.00(s, 9H) |
| 66 | δ 7.50(t, 1H), 7.40(d, 1H), 7.20(d, 1H), 6.60(br s, 1H), 4.45(m, 1H), 4.20(m, 2H), 3.80(s, 1H), 3.65(d, 1H), 3.55(m, 1H), 2.10(m, 1H), 1.45(d, 3H), 1.10(dd, 3H), 1.00(s, 9H) |
| 68 | δ 7.90(d, 1H), 7.80(d, 1H), 7.30(t, 1H), 6.60(m, 1H), 4.20(m, 3H), 3.50(m, 1H), 2.10(m, 2H), 1.45(m, 3H), 1.10(m, 3H), 1.00(s, 9H) |
| 69 | δ 6.60(t, 2H), 6.46(m, 1H), 4.40(m, 1H), 4.10(m, 1H), 4.00(m, 1H), 3.60(dd, 1H), 2.20(m, 1H), 1.45(dd, 3H), 1.10(m, 1H), 1.00(m, 12H) |
| 70 | δ 6.8(s, 1H), 6.6(m, 1H), 4.75(m, 1H), 4.4(m, 1H), 3.6(s, 1H), 2.3(s, 3H), 2.7(m, 1H), 1.45(d, 3H), 1.1(dd, 3H), 1.0(s, 9H) |
| 71a | δ 6.8(s, 1H), 6.6(m, 1H), 4.75(m, 1H), 4.4(m, 1H), 3.6(s, 1H), 2.3(s, 3H), 2.7(m, 1H), 1.45(d, 3H), 1.1(dd, 3H), 1.0(s, 9H) |

INDEX TABLE E-continued

| Cmpd No. | $^1$H NMR Data (CDCl$_3$ solution unless indicated otherwise)$^a$ |
|---|---|
| 71b | δ 6.8(s, 1H), 6.6(m, 1H), 4.75(m, 1H), 4.4(m, 1H), 3.6(s, 1H), 2.3(s, 3H), 2.7(m, 1H), 1.45(d, 3H), 1.1(dd, 3H), 1.0(s, 9H) |
| 73 | δ 6.75(s, 1H), 6.2(m, 1H), 4.1(m, 3H), 3.4(2s, 2H), 2.3(s, 3H), 2.2(m, 1H), 1.9(m, 2H), 1.3(m, 3H), 1.1(m, 3H), 1.0(s, 9H) |
| 74 | δ 6.9(s, 1H), 6.7(s, 1H), 6.2(d, 1H), 4.0(m, 3H), 3.4(2s, 1H), 2.7(m, 1H), 2.0(m, 1H), 1.25(m, 3H), 1.2(m, 3H), 1.0(s, 9H) |
| 75 | δ 7.40(dt, 1H), 7.22(m, 1H), 7.10(m, 2H), 6.70(d, 1H), 6.55(br s, 1H), 6.27(dt, 1H), 4.10(m, 2H), 3.63(d, 1H), 2.22(m, 1H), 1.00(m, 12H) |
| 76 | δ 7.50(s, 1H), 7.40(d, 1H), 7.30(m, 1H), 7.20(t, 1H), 6.60(br s, 1H), 6.50(d, 1H), 6.20(m, 1H), 4.19(m, 2H), 3.60(d, 1H), 2.22(m, 1H), 1.00(m, 12H) |
| 80b | δ 7.00(m, 2H), 6.86(m, 2H), 5.94(d, 1H), 4.42(m, 1H), 3.96(m, 1H), 2.20(m, 1H), 1.95(m, 1H), 1.60(m, 1H), 1.38(t, 3H), 1.22(d, 3H), 0.98(2t, 3H) |
| 82b | δ 7.21(t, 1H), 6.98(dd, 1H), 6.90(t, 1H), 6.80(dd, 1H), 6.18(d, 1H) 4.42(m, 2H), 4.00(m, 2H), 2.20(m, 1H), 1.95(m, 1H), 1.60(m, 1H), 1.38(t, 3H), 1.22(d, 3H), 0.98(2t, 3H) |
| 84b | δ 7.21(d, 1H), 7.24(m, 1H), 6.83(m, 1H), 6.37(2d, 1H), 4.40(m, 2H), 4.00(m, 2H), 2.20(m, 1H), 1.95(m, 1H), 1.57(m, 1H), 1.42(t, 3H), 1.22(d, 3H), 0.98(2t, 3H) |
| 85b | δ 7.10(m, 3H), 6.82(m, 1H), 6.00(d, 1H), 4.42(m, 1H), 4.00(m, 2H), 2.20(m, 1H), 1.98(m, 1H), 1.57(m, 1H), 1.38(t, 3H), 1.22(d, 3H), 0.98(2t, 3H) |
| 87b | δ 7.80(dd, 1H), 7.30(m, 1H), 6.80(m, 2H), 6.40(2d, 1H), 4.44(m, 2H), 4.04(m, 2H), 2.20(m, 1H), 1.99(m, 1H), 1.62(m, 1H), 1.44(t, 3H), 1.22(d, 3H), 0.95(2t, 3H) |
| 89b | δ 7.60(m, 2H), 7.00(m, 2H), 6.10(2d, 1H), 4.50(m, 1H), 4.10(m, 2H), 2.20(m, 1H), 2.05(m, 1H), 1.62(m, 1H), 1.46(t, 3H), 1.22(d, 3H), 0.90(2t, 3H) |
| 94b | δ 7.60(t, 1H), 7.52(m, 1H), 7.10(t, 1H), 6.97(dd, 1H), 6.08(d, 1H), 4.44(m, 1H), 4.10(m, 2H), 2.20(m, 1H), 2.00(m, 1H), 1.52(m, 1H), 1.40(dt, 3H), 1.22(d, 3H), 0.95(dt, 3H) |
| 95 | δ 7.20(m, 2H), 6.92(m, 1H), 6.82(m, 1H), 6.00(t, 1H), 4.44(m, 1H), 4.00(m, 2H), 2.26(s, 3H), 2.22(m, 1H), 1.95(m, 1H), 1.50(m, 1H), 1.40(t, 3H), 1.22(d, 3H), 1.00(dt, 3H) |
| 97b | δ 7.20(m, 2H), 6.95(dt, 1H), 6.82(m, 1H), 4.44(m, 1H), 4.00(m, 2H), 2.63(m, 2H), 2.22(m, 1H), 1.95(m, 1H), 1.60(m, 3H), 1.40(t, 3H), 1.22(d, 3H), 0.95(dt, 3H) |
| 98b | δ 7.18(m, 2H), 6.90(dt, 1H), 6.80(m, 1H), 6.00(m, 1H), 4.44(m, 1H), 4.00(m, 2H), 2.68(m, 2H), 2.22(m, 1H), 1.95(m, 1H), 1.60(m, 1H), 1.40(t, 3H), 1.22(d, 3H), 1.00(dt, 3H) |
| 99 | δ 7.25(m, 1H), 7.18(m, 1H), 6.95(m, 2H), 6.82(t, 2H), 6.00(dd, 1H), 4.44(m, 1H), 4.00(m, 2H), 3.38(m, 1H), 2.22(m, 1H), 1.95(m, 1H), 1.55(m, 3H), 1.40(t, 3H), 1.27(d, 6H), 1.22(d, 3H), 1.00(dt, 6H) |
| 100 | δ 7.25(m, 1H), 7.19(m, 1H), 6.95(m, 2H), 6.82(t, 2H), 6.05(dd, 1H), 4.50(m, 1H), 4.05(m, 2H), 2.22(m, 1H), 1.95(m, 1H), 1.55(m, 15H), 1.22(d, 3H), 1.00(dt, 6H) |
| 101b | δ 7.20(m, 2H), 7.08(m, 2H), 6.78(t, 1H), 6.00(m, 2H), 5.10(m, 2H), 4.40(m, 1H), 4.22(m, 2H), 4.00(m, 2H), 3.40(m, 2H), 2.22(m, 1H), 1.95(m, 1H), 1.58(m, 1H), 1.30(m, 3H), 1.22(d, 3H), 0.95(dt, 3H) |
| 103 | δ 7.30(m, 2H), 6.94(m, 2H), 6.50(dt, 1H), 4.55(m, 1H), 4.10(m, 2H), 3.65(ddd, 2H), 2.20(q, 1H), 2.05(m, 1H), 1.50(m, 1H), 1.40(dt, 3H), 1.20(d, 3H), 0.94(dt, 3H) |
| 105b | δ 6.95(m, 3H), 6.30(dd, 1H), 4.44(m, 1H), 4.10(m, 2H), 2.22(m, 1H), 1.95(m, 1H), 1.60(m, 3H), 1.40(t, 3H), 1.22(d, 3H), 0.95(dt, 3H) |
| 106 | δ 6.84(m, 3H), 6.05(d, 1H), 4.42(m, 1H), 4.01(m, 2H), 2.20(m, 1H), 2.00(m, 1H), 1.55(m, 1H), 1.40(t, 3H), 1.24(d, 3H), 0.98(dt, 3H) |
| 107 | δ 7.02(m, 1H), 6.70(m,1H), 6.60(m, 1H), 6.00(d, 1H), 4.40(m, 1H), 4.00(m, 2H), 2.20(m, 1H), 2.00(m, 1H), 1.55(m, 1H), 1.40(t, 3H), 1.22(d, 3H), 0.97(dt, 3H) |
| 108 | δ 7.03(m, 1H), 6.70(m, 1H), 6.60(m, 1H), 6.20(d, 1H), 4.42(m, 1H), 3.97(m, 2H), 2.20(m, 1H), 2.00(m, 1H), 1.60(m, 1H), 1.40(t, 3H), 1.22(d, 3H), 0.98(m, 3H) |
| 119 | δ 7.00(m, 3H), 6.30(2d, 1H), 6.00(m, 1H), 5.05(m, 2H), 4.44(m, 1H), 3.80(m, 2H), 3.42(m, 2H), 2.33(s, 3H), 2.20(m, 1H), 2.00(m, 1H), 1.60(m, 1H), 1.42(t, 3H), 1.22(d, 3H), 0.98(dt, 3H) |
| 120 | δ 7.10(dd, 1H), 7.02(m, 1H), 6.92(m, 1H), 6.05(d, 1H), 4.40(m, 1H), 4.01(m, 1H), 2.20(m, 1H), 2.00(m, 1H), 1.60(m, 1H), 1.40(t, 3H), 1.22(d, 3H), 0.97(dt, 3H) |
| 136 | δ 6.6(br s, 1H), 6.2(m, 1H), 5.65(m, 1H), 4.5(m, 1H), 4.2(m, 1H), 3.7(m, 1H), 2.2(s, 3H), 2.15(s, 3H), 2.1(m, 3H), 1.6(m, 1H), 1.2(d, 3H), 1.0(m, 3H) |
| 139 | δ 6.6(2s, 1H), 6.1(2d, 1H), 4.2(m, 3H), 2.25(m, 1H), 2.1(m, 1H), 1.6(m, 1H), 1.45(t, 3H), 1.25(d, 3H), 1.0(m, 3H) |
| 140b | δ 6.55(2s, 1H), 6.15 and 5.05(2d, 1H), 4.4–4.6(m, 1H), 4.2–4.4(m, 2H), 2.2(s, 3H), 2.2–2.3(m, 1H), 2.0–2.2(m, 1H), 1.5–1.65(m, 1H), 1.4(2d, 3H), 1.2(d, 3H), 1.0(m,3H) |
| 141 | δ 6.6(2s, 1H), 6.1(2d,.1H), 4.3(m, 2H), 4.1(m, 1H), 2.3(s, 3H), 2.2(m, 1H), 2.1(m, 1H), 1.6(m, 1H), 1.4(t, 3H), 1.2(d, 3H), 1.0(d, 3H) |
| 144 | δ 6.95(2s, 1H), 6.7(s, 1H), 5.91(t, 1H), 4.1(m, 3H), 2.24(m, 1H), 2.0(m, 3H), 1.5(m, 1H), 1.2(m, 6H), 1.0(m, 3H) |
| 149 | δ 6.95(d, 1H), 6.8(d, 1H), 6.4(d, 1H), 6.1(m, 1H), 4.15(m, 2H), 3.4(m, 1H), 3.25(m, 1H), 2.1(q, 1H), 2.0(m, 3H), 1.55(m, 1H), 1.2(d, 3H), 1.0(t, 3H) |
| 152 | δ 6.9(s, 1H), 6.7(s, 1H), 6.05(m, 1H), 4.1(m, 2H), 3.4(m, 1H), 3.25(m, 1H), 2.0(m, 3H), 1.5(m, 1H), 1.2(d, 3H), 1.0(t, 3H) |
| 159 | δ 7.32(s, 1H), 7.23(m, 3H), 6.60(d, 1H), 6.20(dt, 1H), 5.95(d, 1H), 4.12(m, 2H), 2.22(m, 1H), 2.00(m, 1H), 1.21(d, 3H), 1.00(t, 3H) |
| 160 | δ 7.50(s, 1H), 7.40(d, 1H), 7.24(d, 1H), 7.18(t, 1H), 6.50(d, 1H), 6.20(dt, 1H), 6.00(br s, 1H), 4.18(m, 2H), 2.22(m, 1H), 2.00(m, 1H), 1.60(m, 1H), 1.24(m, 3H), 1.00(m, 3H) |

INDEX TABLE E-continued

| Cmpd No. | ¹H NMR Data (CDCl₃ solution unless indicated otherwise)[a] |
|---|---|
| 161 | δ 7.32(m, 4H), 6.70(d, 1H), 6.15(dt, 1H), 6.00(br s, 1H), 4.20(m, 2H), 3.74(s, 2H), 2.25(m, 1H), 2.00(m, 1H), 1.60(m, 1H), 1.24(d, 3H), 1.00(t, 3H) |
| 162 | δ 7.32(m, 1H), 6.80(m, 2H), 6.70(d, 1H), 6.20(t, 1H), 5.95(br s, 1H), 4.12(m, 2H), 2.24(m, 1H), 2.00(m, 1H), 1.60(m, 1H), 1.20(d, 3H), 1.00(t, 3H) |
| 165b | δ 7.31(dd, 1H), 7.00(dt, 1H), 6.80(dd, 1H), 6.30(br d, 1H), 4.40(m, 1H), 4.00(m, 2H), 3.14(s, 1H), 1.40(d, 3H), 1.20(s, 9H) |
| 169b | δ 6.60(dt, 1H), 6.50(dt, 1H), 6.25(d, 1H), 4.40(m, 1H), 4.05(m, 2H), 3.14(d, 1H), 1.40(d, 3H), 1.20(d, 9H) |
| 170a | δ 7.14(d, 1H), 6.81(d, 1H), 6.20(d, 1H), 4.40(m, 1H), 4.05(m, 2H), 3.15(d, 1H), 1.40(d, 3H), 1.18(d, 9H) |
| 171a | δ 7.22(dd, 2H), 6.50(dd, 1H), 4.40(m, 1H), 4.05(m, 2H), 3.18(d, 1H), 1.40(d, 3H), 1.20(d, 9H) |
| 171b | δ 7.22(dd, 2H), 6.50(dd, 1H), 4.40(m, 1H), 4.00(m, 2H), 3.16(d, 1H), 1.40(d, 3H), 1.20(d, 9H) |
| 174a | δ 7.46(s, 1H), 7.00(s, 1H), 6.20(d, 1H), 4.40(m, 1H), 4.10(dd, 1H), 4.00(dd, 1H), 3.15(s, 1H), 1.40(d, 3H), 1.20(s, 9H) |
| 176 | δ 7.20(t, 1H), 6.80(d, 1H), 6.70(d, 2H), 6.18(dd, 1H), 4.40(m, 1H), 4.00(m, 2H), 3.33(s, 3H), 3.15(s, 1H), 1.40(d, 3H), 1.20(dd, 9H) |
| 177 | δ 7.20(t, 1H), 6.80(d, 1H), 6.70(d, 2H), 6.20(dd, 1H), 4.40(m, 1H), 4.00(m, 2H), 3.15(s, 1H), 2.60(q, 2H), 1.40(d, 3H), 1.25(m, 3H), 1.20(dd, 9H) |
| 181a | δ 7.35(d, 1H), 7.00(d, 1H), 6.78(dd, 1H), 6.10(br d, 1H), 4.40(m, 1H), 4.00(dd, 1H), 3.90(dd, 1H), 3.15(s, 1H), 1.40(d, 3H), 1.20(s, 9H) |
| 181b | δ 7.35(d, 1H), 7.00(d, 1H), 6.78(dd, 1H), 6.20(br d, 1H), 4.40(m, 1H), 4.00(m, 2H), 3.13(s, 1H), 1.40(d, 3H), 1.20(s, 9H) |
| 182a | δ 7.25(d, 1H), 6.70(m, 2H), 6.10(br d, 1H), 4.40(m, 1H), 4.00(dd, 1H), 3.90(dd, 1H), 3.16(s, 1H), 1.40(d, 3H), 1.20(s, 9H) |
| 182b | δ 7.25(d, 1H), 6.70(m, 2H), 6.10(br d, 1H), 4.40(m, 1H), 3.95(m, 2H), 3.13(s, 1H), 1.40(d, 3H), 1.20(s, 9H) |
| 183a | δ 7.05(t, 1H), 6.95(m, 1H), 6.75(m, 1H), 6.10(br d, 1H), 4.40(m, 1H), 4.00(dd, 1H), 3.90(dd, 1H), 3.16(s, 1H), 1.40(d, 3H), 1.20(s, 9H) |
| 186 | δ 6.90(m, 2H), 6.30(br t, 1H), 4.40(m, 1H), 4.20(m, 2H), 3.16(s, 1H), 1.40(dd, 3H), 1.20(s, 9H) |
| 187b | δ 7.40(t, 1H), 6.80(t, 1H), 6.30(br d, 1H), 4.40(m, 1H), 4.00(m, 2H), 3.14(s, 1H), 1.40(d, 3H), 1.20(s, 9H) |
| 188a | δ 7.00(m, 1H), 6.82(m, 1H), 6.10(br d, 1H), 4.40(m, 1H), 4.05(dd, 1H), 3.95(dd, 1H), 3.16(s, 1H), 1.40(dd, 3H), 1.20(s, 9H) |
| 188b | δ 7.00(m, 1H), 6.82(m, 1H), 6.10(br d, 1H), 4.40(m, 1H), 4.00(m, 2H), 3.15(s, 1H), 1.40(dd, 3H), 1.20(s, 9H) |
| 189b | δ 6.70(m, 2H), 6.35(br d, 1H) 4.40(m, 1H), 4.05(m, 2H), 3.16(s, 1H), 1.40(dd, 3H), 1.20(s, 9H) |
| 190a | δ 6.90(m, 1H), 6.70(m, 1H), 6.15(d, 1H), 4.40(m, 1H), 4.10(dd, 1H), 3.95(dd, 1H), 3.16(s, 1H), 1.40(dd, 3H), 1.20(s, 9H) |
| 190b | δ 6.90(m, 1H), 6.70(m, 1H), 6.15(d, 1H), 4.40(m, 1H), 4.05(m, 2H), 3.14(s, 1H), 1.40(dd, 3H), 1.20(s, 9H) |
| 191a | δ 7.30(m, 1H), 6.64(m, 1H), 6.30(br d, 1H), 4.40(m, 1H), 4.05(m, 2H), 3.15(s, 1H), 1.40(d, 3H), 1.20(s, 9H) |
| 191b | δ 7.30(m, 1H), 6.64(m, 1H), 6.30(br d, 1H), 4.40(m, 1H), 4.05(m, 2H), 3.14(s, 1H), 1.40(d, 3H), 1.20(s, 9H) |
| 191c | δ 7.30(m, 1H), 6.64(m, 2H), 6.25(br dd, 1H), 4.42(m, 1H), 4.05(m, 2H), 3.15(s, 1H), 1.40(d, 3H), 1.20(d, 9H) |
| 192b | δ 7.30(m, 1H), 6.64(m, 2H), 6.20(br d, 1H), 5.90(dd, 1H), 5.10(dd, 2H), ), 4.40(m, 1H), 4.00(m, 2H), 3.25(s, 1H), 1.40(d, 3H), 1.25(d, 6H) |
| 198b | δ 7.00(t, 1H), 6.95(m, 2H), 6.18(d, 1H), 4.40(m, 1H), 4.10(m, 2H), 3.13(s, 1H), 1.40(d, 3H), 1.20(s, 9H) |
| 199 | δ 7.00(m, 3H), 6.55(m, 1H), 4.40(m, 1H), 4.10(m, 2H), 3.60(m, 1H), 2.20(m, 1H), 1.40(d, 3H), 1.10(m, 3H), 1.00(s, 9H) |
| 200b | δ 7.00(t, 1H), 6.95(m, 2H), 6.15(br d, 1H), 5.95(dd, 1H), 5.20(m, 2H), 4.40(m, 1H), 4.00(m, 2H), 3.24(s, 1H), 1.35(d, 3H), 1.25(d, 6H) |
| 201 | δ 7.25(m, 1H), 7.00(m, 2H), 6.20(m, 1H), 6.00(t, 1H), 4.45(m, 1H), 4.00(m, 2H), 3.10(2s, 1H), 1.45(2d, 3H), 1.15(s, 9H) |
| 203 | δ 7.35(m,2H), 7.10(m, 1H), 6.35(d, 1H), 4.30(m, 3H), 3.20(2s, 1H), 1.45(2d, 3H), 1.20(s, 9H) |
| 204 | δ 7.45(m, 2H), 7.15(m, 1H), 6.50(d, 1H), 5.95(m, 1H), 5.10(m, 2H), 4.40(m, 1H), 4.0–4.2(m, 2H), 3.45(m, 2H), 3.2(2s, 1H), 1.4(2d, 3H), 1.2(s, 9H) |
| 205 | δ 7.45(m, 1H), 7.15(m, 2H), 6.5(d, 1H), 4.4(m, 1H), 4.0–4.2(m, 2H), 3.2(2s, 1H), 2.6(m, 2H), 1.6–1.7(m, 2H), 1.45(2d,3H), 1.2(s, 9H), 0.95(t, 3H) |
| 209 | δ 7.45(m, 2H), 7.10(m, 1H), 6.50(d, 1H), 4.45(m, 1H), 4.0–4.2(m, 2H), 3.20(s, 1H), 2.30 and 2.35(2s, 3H), 1.45(2d, 3H), 1.20(s, 9H) |
| 215b | δ 7.25(d, 1H) 6.70(m, 2H), 6.2–6.3(m, 1H), 5.8–6.0(m, 1H), 5.1–5.2(m, 2H), 4.40(m, 1H), 3.9–4.1(m, 2H), 3.25(2s, 1H), 2.30(s, 2H), 1.40(2d, 3H), 1.25(m, 6H) |
| 219 | δ 7.30(m, 2H), 6.90(m, 2H), 5.8–6.0(m, 1H), 5.2–5.4(m, 2H), 4.1–4.6(m, 3H), 4.00(m, 2H), 3.60(s, 1H), 1.05–1.4(m, 6H) |
| 221a | δ 7.00(m, 1H), 6.70(m, 1H), 6.65(m, 1H), 6.60(m, 1H), 6.10 and 6.20(2d, 1H), 5.5–5.6(m, 1H), 4.40(m, 1H), 3.9–4.1(m, 2H), 3.20(2s, 1H), 1.1–1.4(m, 9H) |
| 221b | δ 7.30(m, 1H), 6.65(m, 2H), 6.45(m, 1H), 6.20 and 6.25(2d, 1H), 5.4–5.6(m, 1H), 4.40(m, 1H), 3.9–4.1(m, 2H), 3.20(2s, 1H), 1.40(d, 3H), 1.30(m, 6H) |

INDEX TABLE E-continued

| Cmpd No. | ¹H NMR Data (CDCl₃ solution unless indicated otherwise)[a] |
|---|---|
| 222 | δ 7.30(m, 1H), 6.6–6.7(m, 2H), 6.10(m, 1H), 4.44.7(m, 2H), 4.40(m, 1H), 4.00(m, 2H), 3.60(s, 1H), 1.40(m, 9H) |
| 223 | δ 7.00(m, 1H), 6.6–6.7(m, 2H), 6.40(dt, 1H), 6.20(m, 1H), 4.80(m, 1H), 4.40(m, 1H), 4.05(m, 1H), 3.95(m, 1H), 3.50(s, 1H), 1.40(m, 9H) |
| 225 | δ 7.15(m, 1H), 6.65(m, 2H), 6.50(2t, 1H), 6.25(m, 1H), 5.8–6.0(m, 1H), 5.2–5.4(m, 2H), 4.2–4.4(m, 3H), 3.9–4.1(m, 2H), 3.60(s, 1H), 1.30 and 1.35(2m, 6H) |
| 227 | δ 7.20(d, 1H), 6.70(m, 2H), 6.3–6.4(m, 1H), 5.8–6.0(m, 1H), 5.2–5.4(m, 2H), 4.2–4.6(m, 3H), 3.95–4.10(m, 2H), 3.60(s, 1H), 2.30(s, 3H), 1.25–1.40(m, 6H) |
| 228 | δ 7.35(m, 5H), 6.56(d, 1H), 6.18(dt, 1H), 6.00(m, 1H), 4.80(m, 1H), 3.16(d, 1H), 1.40(d, 3H), 1.20(d, 9H) |
| 229a | δ 7.10(m, 1H), 7.00(m, 2H), 6.64(d, 1H), 6.42(dd, 1H), 4.80(m, 1H), 3.17(s, 1H), 1.40(d, 3H), 1.20(s, 9H) |
| 229b | δ 7.10(m, 1H), 7.00(m, 2H), 6.64(d, 1H), 6.42(dd, 1H), 4.80(m, 1H), 3.15(s, 1H), 1.40(d, 3H), 1.29(s, 9H) |
| 230 | δ 7.28(dd, 1H), 7.05(t, 1H), 6.80(dt, 1H), 5.90(br d, 1H), 4.40(m, 1H), 4.00(m, 2H), 3.10(m, 1H), 2.20(m, 1H), 2.00(m, 1H), 1.60(m, 1H), 1.40(m, 3H), 1.30(m, 3H), 1.00(m, 3H) |
| 231 | δ 7.30(m, 1H), 6.65(m, 2H), 5.90(d, 1H), 4.45(m, 1H), 3.95(m, 2H), 3.10(m, 1H), 2.20(m, 1H), 1.90(m, 1H), 1.60(m, 1H), 1.40(m, 3H), 1.20(m, 3H), 1.00(m, 3H) |
| 235 | δ 7.40(dt, 1H), 6.80(m, 1H), 6.15(dd, 1H), 4.45(m, 1H), 4.00(m, 2H), 2.20(m, 1H), 2.00(m, 1H), 1.60(m, 1H), 1.40(t, 3H), 1.20(d, 3H), 1.00(dt, 3H) |
| 236 | δ 7.00(m, 1H), 6.85(m, 1H), 6.00(d, 1H), 4.45(m, 1H), 4.00(m, 2H), 2.20(m, 1H), 2.00(m, 1H), 1.60(m, 1H), 1.40(t, 3H), 1.20(d, 3H), 1.00(dt, 3H) |
| 237 | δ 6.70(m, 2H), 6.20(dd, 1H), 4.40(m, 1H), 4.10(m, 2H), 2.20(m, 1H), 2.00(m, 1H), 1.60(m, 1H), 1.40(t, 3H), 1.20(d, 3H), 1.00(dt, 3H) |
| 238 | δ 6.90(m, 1H), 6.70(m, 1H), 6.00(d, 1H), 4.45(m, 1H), 4.05(m, 2H), 2.20(m, 1H), 2.00(m, 1H), 1.60(m, 1H), 1.40(t, 3H), 1.25(d, 3H), 1.00(dt, 3H) |
| 239 | δ 7.50(d, 1H), 7.05(m, 1H), 6.95(m, 1H), 6.10(dd, 1H), 4.40(m, 1H), 4.15(m, 2H), 2.20(m, 1H), 2.00(m, 1H), 1.60(m, 1H), 1.40(t, 3H), 1.25(d, 3H), 1.00(dt, 3H), |
| 240 | δ 7.20(m, 1H), 6.80(m, 1H), 6.75(m, 2H), 6.00(br s, 1H), 4.40(m, 1H), 4.00(m, 2H), 2.60(m, 2H), 2.20(m, 1H), 2.00(m, 1H), 1.60(m, 1H), 1.40(t, 3H), 1.25(m, 6H), 1.00(dt,3H) |
| 241 | δ 7.30(d, 2H), 6.84(d, 2H), 6.00(d, 1H), 4.40(m, 1H), 4.00(m, 2H), 2.20(m, 1H), 1.95(m, 1H), 1.55(m, 1H), 1.35(t, 3H), 1.30(s, 9H), 1.20(d, 3H), 1.00(dt, 3H) |
| 245 | δ 7.60(m, 1H), 6.70(m, 2H), 6.10(br t, 1H), 4.45(m, 1H), 4.00(m, 2H), 2.20(m, 1H), 2.00(m, 1H), 1.60(m, 1H), 1.40(t, 3H), 1.25(d, 3H), 1.00(dt, 3H) |
| 246 | δ 7.40(d, 1H), 7.20(m, 2H), 6.10(br t, 1H), 4.45(m, 1H), 4.15(m, 2H), 2.20(m, 1H), 2.00(m, 1H), 1.60(m, 1H), 1.40(t, 3H), 1.25(d, 3H), 1.00(dt, 3H) |
| 247 | δ 7.40(dt, 1H), 7.30(d, 1H), 7.25(d, 1H), 6.10(br t, 1H), 4.45(m, 1H), 4.10(m, 2H), 2.20(m, 1H), 2.00(m, 1H), 1.60(m, 1H), 1.40(t, 3H), 1.25(d, 3H), 1.00(dt, 3H) |
| 248 | δ 750(d, 1H), 7.10(dt, 1H), 6.95(d, 1H), 6.10(dd, 1H), 4.45(m, 1H), 4.10(m, 2H), 2.20(m, 1H), 2.00(m, 1H), 1.60(m, 1H), 1.40(t, 3H), 1.30(s, 9H), 1.25(d, 3H), 1.00 (dt, 3H) |
| 254 | δ 7.40–7.50(m, 2H), 7.15(m, 1H), 6.25 and 6.50(2d, 1H), 5.85–6.00(m, 1H), 5.00–5.20(m, 2H), 4.45(m, 1H), 4.00–4.20(m, 2H), 3.45(d, 2H), 2.20–2.30(m, 1H), 2.00–2.20(m, 1H), 1.50–1.60(m, 1H), 1.45(2(1, 3H), 1.20(d, 3H), 0.95(m, 3H) |
| 255 | δ 7.00–7.40(m, 3H), 6.30 and 6.50(2d, 1H), 4.40–4.50 (m, 1H), 4.00–4.20(m, 2H), 2.60(t, 2H), 2.00–2.40(m, 2H), 1.40–1.70(m, 9H), 1.20(m, 3H), 0.80–1.10(m, 6H) |
| 256 | δ 7.55(d, 1H), 6.70–6.90(m, 2H), 6.60(t, 1H), 6.00(m, 1H), 4.40–4.50(m, 1H), 4.05–4.20(m, 2H), 2.20(m, 1H), 1.95–2.15(m, 1H), 1.60(m, 1H), 1.45(m, 3H), 1.20(d, 3H), 0.90 and 1.00(2t, 3H) |
| 257 | δ 7.55(d, 1H), 6.70–6.90(m, 2H), 6.60(t, 1H), 6.00(m, 1H), 4.40–4.50(m, 1H), 4.05–4.20(m, 2H), 2.20(m, 1H), 1.95–2.15(m, 1H), 1.60(m, 1H), 1.45(m, 3H), 1.20(d, 3H), 0.90 and 1.00(2t, 3H) |
| 262 | δ 7.30(m, 3H), 5.80(m, 2H), 4.15(m, 2H), 2.50(m, 2H), 2.20(m, 1H), 2.00(m, 1H), 1.50(m, 1H), 1.20(m, 3H), 1.00(m, 3H) |
| 263 | δ 7.20(m, 5H), 6.50(t, 1H), 6.20(dd, 1H), 5.70(t, 1H), 4.80(m, 1H), 2.22(m, 1H), 2.00(m, 1H), 1.40(dd, 3H), 1.20(dd, 3H), 1.00(dt, 3H) |
| 264 | δ 7.30(dt, 1H), 7.10(d, 1H), 7.05(d, 1H), 6.95(dt, 1H) 6.50(dt, 1H), 6.00(br s, 1H), 4.08(m, 2H), 2.20(m, 1H) 2.00(m, 1H), 1.60(m, 1H), 1.20(d, 3H), 1.00(t, 3H) |
| 265 | δ 7.30(m, 5H), 6.50(s, 1H), 5.90(s, 1H), 4,10(m, 2H) 2.30(m, 1H), 2.20(m, 1H), 1.60(m, 1H), 1.90(s, 3H) 1.22(m, 3H), 1.00(m, 3H) |
| 266 | δ 7.40(m, 1H), 7.20(m, 1H), 6.95(m, 1H), 6.20(m, 1H), 5.75(d, 1H), 4.85(m, 1H), 2.20(m, 1H), 2.00(m, 1H), 1.60(m, 1H), 1.40(m, 3H), 1.25(m, 3H), 1.00(m, 3H) |

INDEX TABLE E-continued

| Cmpd No. | ¹H NMR Data (CDCl₃ solution unless indicated otherwise)ᵃ |
|---|---|
| 267a | δ 7.10(m, 1H), 6.95(m, 2H), 6.65(d, 1H), 6.36(dd, 1H), 5.80(br s, 1H), 4.05(m, 1H), 2.20(q, 1H), 2.00(m, 1H), 1.60(m, 1H), 1.40(d, 3H), 1.20(d,3H), 1.00(t,3H) |
| 268 | δ 7.35(m, 5H), 6.40(m, 1H), 5.80(m, 1H), 4.15(m, 2H), 2.20(m, 1H), 2.00(m, 1H), 1.60(m, 1H), 1.20(m, 3H), 1.10(m, 3H), 1.00(m, 3H) |
| 270 | δ 730(m, 2H), 7.20(m, 2H), 6.45(s, 1H), 5.90(m, 1H), 4.10(m, 2H), 3.45(s, 3H), 2.25(m, 1H), 2.00(m, 1H), 1.60(m, 1H), 1.44(m, 3H), 1.00(m, 3H) |
| 271 | δ 7.35(m, 3H), 6.80(m, 1H), 5.80(m, 1H), 4.10(m, 2H), 2.20(m, 1H), 2.00(m, 1H), 1.55(m, 1H), 1.25(m, 3H), 1.15(m, 3H), 1.00(m, 3H) |
| 275 | δ 7.4–7.5(m, 2H), 7.15(m, 1H), 6.70(m, 1H), 5.8–6.0 (m, 1H), 5.0–5.2(m, 2H), 4.40(m, 1H), 3.8–4.2(m, 2H), 3.40 and 3.50(2d, 1H), 3.40(m, 2H), 2.1–2.5(m, 1H), 1.4–1.5(m, 3H), 1.10 and 1.20(2d, 3H), 1.00(s, 9H) |
| 276 | δ 7.40(m, 1H), 7.1–7.2(m, 1H), 6.70(m, 1H), 4.40(m, 1H), 3.8–4.2(m, 2H), 3.45–3.7 (m, 1H), 2.60(m, 2H), 2.1–2.5(m, 1H), 1.60(m, 2H), 1.45(d, 2H), 1.10 and 1.20 (2m, 3H), 1.00(s, 9H), 0.90–1.00(m, 3H) |
| 277 | δ 7.55(d, 1H), 6.30–6.4(m, 3H), 4.40(m, 1H), 3.80–4.20(m, 3H), 3.40–3.65(m, 1H), 2.15(m, 1H), 1.45(d, 3H), 1.00–1.25(m, 3H), 1.00(s, 9H) |
| 278 | δ 7.50(m, 1H), 6.75–6.90(m, 1H), 6.20–6.50(m, 1H), 4.40(m, 1H), 3.90–4.20(m, 2H), 3.60(m, 1H), 2.20(m, 1H), 1.40(d, 3H), 1.00–1.25(m, 3H), 1.00(s, 9H) |
| 279 | δ 7.20–7.40(m, 1H), 6.80–6.90(m, 1H), 6.50(m, 1H), 4.00–4.50(m, 3H), 3.45–3.70(m, 1H), 2.10–2.25(m, 1H), 1.40(m, 3H), 1.00–1.20(m, 3H), 1.00(s, 9H) |
| 280 | δ 7.40(m, 2H), 7.00–7.15(m, 1H), 6.70(m, 1H), 4.40(m, 1H), 3.80–4.20(m, 2H), 3.45–3.70(m, 1H), 2.30(s, 3H), 2.10–2.30(m, 1H), 1.50(d, 3H), 1.10–1.20(m, 3H), 1.00(s, 9H) |
| 281 | δ 7.65(m, 1H), 7.50(m, 1H), 7.20(m, 1H), 6.75(m, 1H), 3.90–4.50(m, 3H), 3.45–3.70 (m, 1H), 2.10–2.40(m, 1H), 1.60(m, 3H), 1.00–1.20(m, 3H), 1.00(s, 9H) |
| 283 | δ 1.2(d, 3H), 2.6–2.7(m, 2H), 3.4(m, 1H), 4.4(m, 1H), 5.0–5.3(m, 3H), 5.6–5.85(m, 1H), 6.6(m, 1H), 7.0(m, 1H), 7.3–7.5(m, 5H) |
| 284 | δ 1.25(m, 3H), 2.65(m, 2H), 3.45(m, 1H), 4.4(m, 1H), 5.0–5.3(m, 2H), 5.4(s, 1H), 5.6–5.85(m, 1H), 6.35–6.45(m, 2H), 6.7(m, 1H), 7.3–7.5(m, 5H), 7.5–7.6(m, 1H) |
| 285 | δ 1.25(m, 3H), 2.65(m, 2H), 3.45(m, 1H), 4.4(m, 1H), 5.0–5.2(m, 2H), 5.4(s, 1H), 5.6–5.8(m, 1H), 6.45(m, 1H), 6.65(d, 1H), 7.0(t, 1H), 7.3–7.4(m, 6H), 7.8(d, 1H) |
| 286 | δ 1.0–1.1(m, 3H), 1.25(d, 3H), 1.9–2.05(m, 1H), 3.3–3.4(m, 1H), 4.4(m, 1H), 5.4(m, 1H), 6.2(d, 2H), 6.7(m, 1H), 7.5(m, 5H), 7.5–7.6(m, 1H) |
| 287 | δ 0.9(m, 3H), 1.25(d, 3H), 1.4(m, 2H), 1.8–1.95(m, 2H), 3.4(m, 1H), 4.4(m, 1H), 5.2(s, 1H), 6.6(d, 2H), 6.7(m, 1H), 7.3–7.45(m, 5H), 7.7-7.8(m, 1H) |
| 288 | δ 0.9(m, 3H), 1.25(d, 3H), 1.4(m, 2H), 1.8–1.95(m, 2H), 3.4(m, 1H), 4.4(m, 1H), 5.45(s, 1H), 6.4(m, 1H), 6.65(d, 1H), 7.0(t, 1H), 7.3–7.4(m, 6H), 7.6(d, 1H) |
| 289 | δ 0.95–1.1(m, 6H), 1.25(d, 3H), 2.4(m, 1H), 3.3(m, 1H), 4.4(m, 1H), 5.4(s, 1H), 6.4 (d, 2H), 6.7(t, 1H), 7.4(m, 5H), 7.55(m, 1H) |
| 290 | δ 0.95–1.1(m, 6H), 1.25(d, 3H), 2.4(m, 1H), 3.3(m, 1H), 4.4(m, 1H), 5.45(s, 1H), 6.4(m, 1H), 6.65(d, 1H), 7.0(t, 1H), 7.3–7.4(m, 6H), 7.6(d, 1H) |
| 291 | δ 1.1(s, 9H), 1.25(m, 3H), 3.15(2s, 1H), 4.4(m, 1H), 5.45 and 5.5(2d, 1H), 6.25(d, 1H), 6.65(m, 1H), 7.0(m, 1H), 7.3–7.4(m, 6H), 7.6(d of m, 1H) |
| 292 | 1.15(2s, 9H), 1.4(d, 3H), 3.1(s, 1H), 3.95–4.1(m, 2H), 4.4(m, 1H), 6.2(m, 1H), 6.5 (t, 1H) 6.7(d, 2H), 7.5(m, 1H) |
| 293 | δ 1.0 and 1.1(2t, 3H), 1.25(d, 3H), 1.7–2.1(m, 2H), 3.3–3.4(m, 1H), 4.4(m, 1H), 5.3 (m, 1H), 6.4(m, 2H), 6.7–6.8(m, 1H), 7.0(m, 1H), 7.3–7.4(m, 5H) |
| 294 | δ 1.25(m, 6H), 1.35(d, 3H), 3.2(s, 1H), 4.0(m, 2H), 4.4(m, 1H), 5.1–5.2(m, 2H), 5.8–6.0(m, 1H), 6.15(m, 1H), 6.45(2t, 1H), 6.6–6.7(m, 2H), 7.15(m, 1H) |
| 295 | δ 1.4–1.5(m, 9H), 2.4(2s, 1H), 3.15(2s, 1H), 4.0–4.1(m, 2H), 4.4–4.5(m, 1H), 6.45(t, 1H), 6.4–6.7(m, 3H), 7.15(m, 1H) |
| 297 | δ 0.8–0.9(m, 3H), 1.2–1.4(m, 6H), 1.5–1.7(m, 2H), 3.3(4s, 1H), 3.9–4.1(m, 2H), 4.2 and 4.4(2m, 1H), 5.1–5.4(m, 2H), 5.75–5.9(m, 1H), 6.0–6.2(m, 1H), 6.9–7.1(m, 3H) |
| 302 | δ 1.3–1.4(m 3H), 1.5–1.6(m, 3H), 2.6 2.7(3s, 1H), 3.4–3.4(4s, 1H), 3.9–4.1(m, 2H), 4.2 and 4.4(2m, 1H), 5.2–5.9(m, 3H), 6.1 and 6.2(2m, 1H), 6.9–7.1(m, 3H) |
| 304 | δ 1.0(m, 3H), 1.3(d, 3H), 2.0(m, 2H), 3.23(q, 1H), 4.4(m, 1H), 5.45(m, 1H), 6.5(d, 1H), 6.65(d, 1H), 7.0(t, 1H), 7.3–7.5(m, 6H), 7.6(d, 1H) |
| 305 | δ 7.47(d, 1H), 7.08(dt, 1H), 6.97(d, 1H), 6.30(br dd, 1H), 4.42(m, 1H), 4.12(m, 2H), 3.17(s, 1H), 1.42(d, 3H), 1.20(s, 9H) |
| 306 | δ 7.18(m, 2H), 6.97(t, 1H), 6.80(d, 1H), 6.21(m, 1H), 4.42(m, 1H), 4.00(m, 2H), 3.16(s, 1H), 3.10(m, 1H), 1.60(m, 2H), 1.40(d, 3H), 1.20(m, 12H), 0.85(m, 3H) |
| 307 | δ 7.65(t, 1H), 7.58(t, 1H), 7.35(t, 1H), 6.90(d, 1H), 6.40(dd, 1H), 6.20(br d, 1H), 4.80(m, 1H), 3.20(s, 1H), 1.42(d, 3H), 1.20(s, 9H) |
| 308 | δ 7.40(q, 1H), 7.30(m, 1H), 7.10(t, 1H), 7.05(t, 1H), 6.50(d, 1H), 5.90(m, 1H) 5.63 (q, 1H), 4.90(m, 1H), 3.10(s, 1H), 1.30(d, 3H), 1.20(s, 9H) |
| 309 | δ 7.40(m, 1H), 6.90(m, 1H), 6.85(m, 1H), 6.50(d, 1H), 6.00(br s, 1H), 5.60(m, 1H), 4.82(m, 1H), 3.10(s, 1H), 1.40(d, 3H), 1.20(s, 9H) |
| 311 | δ 7.30(m, 2H), 6.95(m, 3H), 6.00(m, 1H), 4.40(m, 1H), 4.00(m, 2H), 2.20(m, 1H), 1.60(m, 4H) |
| 312 | δ 7.60(d, 1H), 7.50(m, 1H), 7.05(t, 1H), 6.98(t, 1H), 6.15(m, 1H), 4.50(m, 1H), 4.00 (m, 2H), 2.20(m, 2H), 1.50(m, 3H), 1.20(m, 3H) |

INDEX TABLE E-continued

| Cmpd No. | ¹H NMR Data (CDCl₃ solution unless indicated otherwise)[a] |
|---|---|
| 313 | 7.50(m, 1H), 7.25(m, 1H), 6.90(m, 2H), 6.25(m, 1H), 4.40(m, 1H), 4.05(m, 2H), 2.20(m, 1H), 1.60(d, 3H), 1.40(m, 4H) |
| 314 | 7.20(m, 2H), 6.95(t, 1H), 6.90(t, 1H), 6.05(m, 2H), 5.08(m, 2H), 4.42(m, 1H), 4.00 (m, 2H), 3.42(m, 2H), 2.20(m, 1H), 1.60(d, 3H), 1.40(m, 4H) |
| 315 | 7.00(m, 4H), 6.05(m, 1H), 4.40(m, 1H), 4.05(m, 2H), 2.20(m, 1H), 1.60(m, 3H), 1.40(m, 4H) |

[a]¹H NMR data are in ppm downfield from tetramethylsilane. Couplings are designated by(s)-singlet, (d)-doublet, (t)-triplet, (q)-quartet, (m)-multiplet, (dd)-doublet of doublets, (dt)-doublet of triplets, (br s)-broad singlet. A number in front of the coupling indicates more than one set of peaks with this coupling. For example, "2d, 3H" indicates two doublets each with three protons,

BIOLOGICAL EXAMPLES OF THE INVENTION

Test compounds were first dissolved in acetone in an amount equal to 3% of the final volume and then suspended at a concentration of 200 ppm in purified water containing 250 ppm of the surfactant Trem® 014 (polyhydric alcohol esters). The resulting test suspensions were then used in the following tests. Spraying these 200 ppm test suspensions to the point of run-off on the test plants is the equivalent of a rate of 500 g/ha.

Test A

The test suspension was sprayed to the point of run-off on wheat seedlings. The following day the seedlings were inoculated with a spore dust of *Eiysiphe graminis f.* sp. *tritici*, (the causal agent of wheat powdery mildew) and incubated in a growth chamber at 20° C. for 7 days, after which disease ratings were made.

Test B

The test suspension was sprayed to the point of run-off on wheat seedlings. The following day the seedlings were inoculated with a spore suspension of *Puccinia recondita* (the causal agent of wheat leaf rust) and incubated in a saturated atmosphere at 20° C. for 24 h, and then moved to a growth chamber at 20° C. for 6 days, after which disease ratings were made.

Test C

The test suspension was sprayed to the point of run-off on rice seedlings. The following day the seedlings were inoculated with a spore suspension of *Pyricularia oryzae* (the causal agent of rice blast) and incubated in a saturated atmosphere at 27° C. for 24 h, and then moved to a growth chamber at 30° C. for 5 days, after which disease ratings were made.

Test D

The test suspension was sprayed to the point of run-off on tomato seedlings. The following day the seedlings were inoculated with a spore suspension of *Phytophthora infestans* (the causal agent of potato and tomato late blight) and incubated in a saturated atmosphere at 20° C. for 24 h, and then moved to a growth chamber at 20° C. for 5 days, after which disease ratings were made.

Test E

The test suspension was sprayed to the point of run-off on cucumber seedlings. The following day the seedlings were inoculated with a spore suspension of *Botrytis cinerea* (the causal agent of gray mold on many crops) and incubated in a saturated atmosphere at 20° C. for 48 h, and moved to a growth chamber at 20° C. for 5 days, after which disease ratings were made.

Results for Tests A–E are given in Table A. In the table, a rating of 100 indicates 100% disease control and a rating of 0 indicates no disease control (relative to the controls). A dash (-) indicates no test results. ND indicates disease control not determined due to phytotoxicity.

TABLE A

| Cmpd. No | Test A | Test B | Test C | Test D | Test E |
|---|---|---|---|---|---|
| 1a | 60 | 0 | 53 | 0 | 0 |
| 1b | 34 | 11 | 74 | 0 | 0 |
| 1c | 60 | 85 | 73 | 16 | 0 |
| 1d | 92 | 0 | 100 | 0 | 0 |
| 1e | 92 | 0 | 100 | 80 | 47 |
| 2a | 0 | 0 | 0 | 0 | 55 |
| 2b | 0 | 0 | 100 | 0 | 0 |
| 2c | 86 | 0 | 100 | 24 | 0 |
| 3a | 85 | 0 | 94 | 0 | 55 |
| 3b | 0 | 0 | 86 | 32 | 0 |
| 3c | 38 | 0 | 100 | 4 | 0 |
| 3d | 92 | 0 | 100 | 99 | 0 |
| 3e | 86 | 0 | 100 | 68 | 0 |
| 4a | 0 | 67 | 99 | 66 | 0 |
| 4b | 86 | 0 | 99 | 89 | 82 |
| 4c | 35 | 0 | 94 | 0 | 58 |
| 5a | 0 | 68 | 0 | 0 | 0 |
| 5b | 0 | 86 | 100 | 24 | 0 |
| 6a | 0 | 0 | 74 | 0 | 0 |
| 6b | 38 | 68 | 53 | 4 | 0 |
| 6c | 0 | 0 | 97 | 9 | 0 |
| 6d | 77 | 28 | 97 | 0 | 0 |
| 6e | 0 | 0 | 100 | 96 | 70 |
| 7a | 77 | 85 | 91 | 89 | 0 |
| 7b | 77 | 0 | 74 | 89 | 47 |
| 7c | 0 | 0 | 86 | 9 | 45 |
| 7d | 62 | 68 | 99 | 0 | 6 |
| 8a | 0 | 0 | 85 | 0 | 7 |
| 8b | 37 | 0 | 100 | 89 | 47 |
| 8c | 0 | 0 | 100 | 0 | 0 |
| 9a | 0 | 0 | 53 | 0 | 0 |
| 9b | 62 | 68 | 99 | 28 | 0 |
| 9c | 62 | 28 | 100 | 51 | 0 |
| 10a | 0 | 27 | 86 | 23 | 0 |
| 10b | 62 | 67 | 86 | 95 | 0 |
| 10c | 0 | 86 | 53 | 35 | 0 |
| 10d | 77 | 0 | 74 | 35 | 45 |
| 11a | 77 | 0 | 97 | 0 | 82 |
| 11b | 77 | 85 | 99 | 23 | 0 |
| 12a | 86 | 68 | 91 | 0 | 0 |
| 12b | 77 | 0 | 94 | 68 | 0 |
| 13a | 34 | 0 | 51 | 0 | 0 |
| 13b | 0 | 0 | 86 | 4 | 83 |
| 14a | 0 | 0 | 94 | 45 | 58 |
| 14b | 61 | 0 | 86 | 23 | 0 |
| 15a | 0 | 28 | 97 | 92 | 86 |
| 15b | 0 | 0 | 97 | 45 | 0 |

TABLE A-continued

| Cmpd. No | Test A | Test B | Test C | Test D | Test E |
| --- | --- | --- | --- | --- | --- |
| 16 | 0 | 0 | 97 | 48 | 0 |
| 17a | 85 | 67 | 30 | 16 | 0 |
| 17b | 38 | 28 | 100 | 0 | 0 |
| 18a | 0 | 0 | 91 | 0 | 0 |
| 18b | 77 | 0 | 94 | 0 | 0 |
| 19 | 0 | 0 | 97 | 0 | 0 |
| 20a | 63 | 0 | 97 | 70 | 0 |
| 20b | 0 | 0 | 100 | 0 | 0 |
| 21a | 38 | 68 | 99 | 4 | 0 |
| 21b | 37 | 27 | 99 | — | 0 |
| 22 | 0 | 0 | 100 | 0 | 0 |
| 23 | 0 | 0 | 97 | 48 | 0 |
| 24 | 62 | 0 | 53 | 66 | 94 |
| 25a | 95 | 28 | 32 | 0 | 0 |
| 25b | 63 | 0 | 97 | 24 | 0 |
| 26a | 38 | 28 | 97 | 51 | 0 |
| 26b | 38 | 68 | 100 | 81 | 0 |
| 27a | 38 | 0 | 100 | 81 | 0 |
| 27b | 91 | 0 | 100 | 0 | 0 |
| 28a | 38 | 28 | 100 | 68 | 0 |
| 28b | 86 | 28 | 100 | 96 | 0 |
| 29a | 0 | 0 | 74 | 35 | 6 |
| 29b | 0 | 0 | 100 | 23 | 0 |
| 30a | 0 | 0 | 100 | 0 | 0 |
| 30b | 77 | 27 | 97 | 0 | 0 |
| 31a | 62 | 68 | 74 | 51 | 0 |
| 31b | 0 | 0 | 94 | 0 | 0 |
| 32a | 0 | 27 | 91 | 0 | 0 |
| 32b | 0 | 27 | 94 | 23 | 0 |
| 33a | 0 | 0 | 97 | 0 | 0 |
| 33b | 0 | 67 | 100 | 80 | 0 |
| 34 | 62 | 85 | 91 | 0 | 0 |
| 35a | 0 | 0 | 74 | 80 | 0 |
| 35b | 37 | 0 | 91 | 0 | 0 |
| 36a | 0 | 27 | 99 | 89 | 0 |
| 36b | 62 | 27 | 100 | 80 | 0 |
| 37a | 62 | 68 | 100 | 68 | 0 |
| 37b | 77 | 68 | 99 | 96 | 0 |
| 38 | 0 | 28 | 53 | 0 | 22 |
| 39 | 0 | 0 | 86 | 2 | 0 |
| 40 | 21 | 0 | 86 | 0 | 0 |
| 41 | 62 | 0 | 97 | 66 | 47 |
| 42 | 0 | 0 | 53 | 2 | 0 |
| 43 | 0 | 0 | 86 | 66 | 0 |
| 44 | 0 | 0 | 94 | 89 | 0 |
| 45 | 0 | 0 | 86 | 0 | 0 |
| 46 | 0 | 0 | 53 | 66 | 0 |
| 47 | 0 | 0 | 53 | 52 | 0 |
| 48 | 0 | 0 | 91 | 0 | 0 |
| 49 | 0 | 0 | 0 | 0 | 0 |
| 50 | 86 | 28 | 53 | 57 | 0 |
| 51 | 71 | 0 | 53 | 68 | 0 |
| 52 | 71 | 86 | 0 | 81 | 0 |
| 53 | 0 | 0 | 53 | 0 | 0 |
| 54 | 34 | 11 | 32 | 0 | 16 |
| 55 | 0 | 0 | 85 | 0 | 0 |
| 56* | 74 | 0 | 85 | 0 | 0 |
| 57* | 91 | 0 | 85 | 0 | 0 |
| 58* | 57 | 0 | 52 | 0 | 0 |
| 59* | 0 | 0 | 52 | 0 | 0 |
| 60* | 91 | 0 | 0 | 0 | 0 |
| 61* | 74 | 0 | 73 | 0 | 0 |
| 62* | 74 | 0 | 52 | 0 | 0 |
| 63 | 0 | 0 | 0 | 2 | 0 |
| 64 | 0 | 0 | 53 | 2 | 0 |
| 65 | 0 | 0 | 0 | 2 | 0 |
| 66 | 0 | 0 | 0 | 69 | 0 |
| 67 | 0 | 0 | 0 | 92 | 0 |
| 68 | 62 | 27 | 86 | 82 | 0 |
| 69 | 0 | 0 | 53 | 2 | 0 |
| 70 | 63 | 0 | 0 | 13 | 0 |
| 71a | 0 | 0 | 53 | 19 | 0 |
| 71b** | 0 | 0 | 0 | 19 | 0 |
| 72 | 0 | 0 | 91 | 0 | 0 |
| 73 | 30 | 28 | 53 | 0 | 11 |
| 74 | 0 | 86 | 53 | 23 | 0 |
| 75* | 0 | 0 | 52 | 19 | 0 |
| 76* | 0 | 0 | 0 | 19 | 0 |
| 77a | 73 | 28 | 86 | — | 0 |
| 77b* | 33 | 0 | 74 | 0 | 0 |
| 78a | 0 | 93 | 90 | 0 | 74 |
| 78b | 84 | 0 | 99 | — | 0 |
| 79a* | 0 | 0 | 53 | 0 | 0 |
| 79b* | 0 | 0 | 100 | 0 | 0 |
| 80a* | 0 | 0 | 86 | 20 | 0 |
| 80b* | 83 | 0 | 97 | 0 | 0 |
| 81a | 0 | 0 | 0 | 0 | 55 |
| 81b* | 85 | 0 | 74 | 0 | 0 |
| 82a* | 0 | 0 | 53 | 43 | 0 |
| 82b | 31 | 0 | 97 | 15 | 0 |
| 83a* | 0 | 0 | 32 | 0 | 0 |
| 83b* | 52 | 0 | 53 | 0 | 0 |
| 84a* | 29 | 0 | 0 | 20 | 0 |
| 84b* | 57 | 28 | 73 | 75 | 0 |
| 85a | 55 | 0 | 53 | — | 0 |
| 85b* | 0 | 0 | 53 | 0 | 0 |
| 86a* | 0 | 67 | 0 | 0 | 0 |
| 86b* | 52 | 0 | 0 | 28 | 0 |
| 87a* | 0 | 0 | 74 | 0 | 0 |
| 87b* | 52 | 0 | 0 | 0 | 0 |
| 88* | 52 | 0 | 0 | 0 | 0 |
| 89a | 0 | 0 | 74 | 20 | 0 |
| 89b | 26 | 68 | 91 | — | 47 |
| 90 | 84 | 0 | 32 | 0 | 0 |
| 91 | 74 | 0 | 53 | 0 | 0 |
| 92* | 60 | 0 | 0 | 0 | 0 |
| 93* | 57 | 0 | 85 | 19 | 0 |
| 94a | 0 | 0 | 0 | 0 | 0 |
| 94b* | 71 | 0 | 0 | 0 | 0 |
| 95* | 52 | 86 | 94 | 0 | 0 |
| 96* | 0 | 0 | 0 | 90 | 0 |
| 97a* | 0 | 0 | 0 | 20 | 0 |
| 97b* | 71 | 0 | 53 | 0 | 0 |
| 98a | 0 | 0 | 53 | 24 | 0 |
| 98b* | 52 | 0 | 74 | 0 | 0 |
| 99* | 83 | 0 | 0 | 68 | 0 |
| 100* | 52 | 0 | 0 | 0 | 0 |
| 101a | 0 | 0 | 0 | 46 | 22 |
| 101b* | 0 | 0 | 0 | 0 | 0 |
| 102* | 60 | 0 | 0 | 0 | 0 |
| 103 | 0 | 26 | 53 | 0 | 0 |
| 104* | 84 | 0 | 97 | 0 | 0 |
| 105a | 0 | 0 | 53 | 0 | 55 |
| 105b* | 21 | 0 | 74 | 0 | 0 |
| 106* | 84 | 0 | 97 | 19 | 0 |
| 107* | 71 | 0 | 100 | 0 | 0 |
| 108* | 57 | 0 | 94 | 0 | 0 |
| 109* | 52 | 0 | 53 | 0 | 0 |
| 110* | 90 | 0 | 97 | 0 | 0 |
| 111* | 90 | 0 | 0 | 90 | 0 |
| 112* | 71 | 0 | 0 | 0 | 0 |
| 113* | 0 | 0 | 97 | 19 | 0 |
| 114* | 83 | 0 | 0 | 0 | 0 |
| 115* | 52 | 0 | 32 | 0 | 0 |
| 116* | 21 | 0 | 0 | 0 | 0 |
| 117* | 83 | 0 | 74 | 0 | 0 |
| 118* | 83 | 0 | 0 | 0 | 0 |
| 119 | 31 | 0 | 32 | 0 | 0 |
| 120* | 29 | 0 | 52 | 19 | 0 |
| 121* | 71 | 0 | 53 | 0 | 0 |
| 122 | 0 | 0 | 0 | 0 | 0 |
| 123* | 90 | 0 | 53 | 0 | 0 |
| 124* | 83 | 0 | 0 | 0 | 0 |
| 125* | 90 | 0 | 99 | 0 | 0 |
| 126* | 0 | 0 | 73 | 0 | 0 |
| 127* | 0 | 0 | 94 | 19 | 0 |
| 128 | 86 | 0 | 74 | 13 | 0 |
| 129 | 38 | 26 | 74 | 0 | 0 |
| 130 | 0 | 0 | 32 | 2 | 0 |
| 131 | 0 | 0 | 53 | 52 | 0 |

TABLE A-continued

| Cmpd. No | Test A | Test B | Test C | Test D | Test E |
|---|---|---|---|---|---|
| 132 | 0 | 0 | 0 | 2 | 0 |
| 133 | 0 | 0 | 0 | 0 | 0 |
| 134 | 0 | 0 | 0 | 30 | 0 |
| 135 | 0 | 0 | 53 | 2 | 0 |
| 136 | 34 | 0 | 78 | 0 | 0 |
| 137 | 0 | 0 | 53 | 0 | 0 |
| 138 | 0 | 0 | 53 | 13 | 0 |
| 139 | 71 | 0 | 91 | 0 | 0 |
| 140a | 29 | 0 | 90 | 0 | 0 |
| 140b | 63 | 28 | 74 | 38 | 0 |
| 141 | 38 | 68 | 74 | 84 | 0 |
| 143 | 0 | 0 | 53 | 0 | 0 |
| 144 | 0 | 28 | 53 | 0 | 0 |
| 145 | 0 | 9 | 0 | 20 | 0 |
| 146 | 0 | 22 | 0 | 0 | 0 |
| 148 | 0 | 0 | 74 | 0 | 0 |
| 149 | 30 | 27 | 53 | 0 | 0 |
| 150 | 0 | 0 | 60 | 0 | 87 |
| 151 | 0 | 0 | 91 | — | 0 |
| 152 | 55 | 68 | 86 | — | 0 |
| 153 | 92 | 64 | 94 | 92 | 0 |
| 154 | 52 | 0 | 52 | 0 | 0 |
| 155 | 71 | 0 | 86 | 23 | 0 |
| 156* | 0 | 0 | 0 | 0 | 0 |
| 157* | 0 | 0 | 97 | 0 | 0 |
| 158* | 0 | 0 | 52 | 0 | 0 |
| 159 | 0 | 0 | 0 | 0 | 47 |
| 160* | 57 | 86 | 52 | 85 | 0 |
| 161* | 0 | 0 | 0 | 0 | 0 |
| 162 | 0 | 0 | 74 | 95 | 82 |
| 163* | 0 | 0 | 52 | 42 | 0 |
| 164 | 0 | 0 | 72 | 56 | 7 |
| 165a | 86 | 0 | 74 | 23 | 86 |
| 165b | 95 | 0 | 94 | 23 | 95 |
| 166a | 0 | 0 | 99 | 76 | 58 |
| 166b | 0 | 0 | 99 | 0 | 0 |
| 167 | 0 | 0 | 74 | 23 | 0 |
| 168a | 76 | 0 | 74 | 0 | 58 |
| 168b | 95 | 0 | 94 | 45 | 86 |
| 169a | 84 | 27 | 91 | 24 | 0 |
| 169b | 0 | 0 | 97 | 0 | 0 |
| 170a | 35 | 0 | 53 | 0 | 58 |
| 170b | 61 | 68 | 53 | 23 | 95 |
| 171a | 0 | 0 | 86 | 0 | 0 |
| 171b | 91 | 0 | 53 | 0 | 58 |
| 172 | 0 | 0 | 86 | 0 | 95 |
| 173a | 63 | 28 | 52 | 33 | 0 |
| 173b | 0 | 0 | 90 | 91 | 0 |
| 174a | 0 | 0 | 31 | 54 | 0 |
| 174b | 0 | 28 | 52 | 91 | 0 |
| 175* | 0 | 0 | 74 | 33 | 0 |
| 176 | 77 | 0 | 94 | 56 | 6 |
| 177 | 62 | 0 | 94 | 35 | 6 |
| 178 | 0 | 0 | 53 | 0 | 58 |
| 179 | 35 | 0 | 74 | 23 | 58 |
| 180 | 61 | 0 | 74 | 76 | 0 |
| 181a | 0 | 0 | 86 | 56 | 69 |
| 181b | 37 | 0 | 74 | 0 | 90 |
| 182a | 0 | 0 | 0 | 0 | 0 |
| 182b | 0 | 68 | 94 | 0 | 0 |
| 183a | 0 | 28 | 86 | 35 | 0 |
| 183b | 86 | 28 | 94 | 35 | 69 |
| 184a | 62 | 0 | 74 | 0 | 6 |
| 184b | 62 | 0 | 74 | 9 | 45 |
| 185 | 0 | 28 | 86 | 9 | 45 |
| 186 | 0 | 0 | 100 | 0 | 45 |
| 187a | 0 | 28 | 94 | 9 | 6 |
| 187b | 77 | 68 | 94 | 91 | 6 |
| 188a | 0 | 0 | 97 | 56 | 0 |
| 188b | 0 | 0 | 100 | 35 | 45 |
| 189a | 0 | 0 | 97 | 0 | 6 |
| 189b | 0 | 0 | 100 | 35 | 0 |
| 190a | 0 | 0 | 91 | 0 | 6 |
| 190b | 0 | 0 | 94 | 0 | 0 |
| 191a | 0 | 0 | 100 | 25 | 85 |
| 191b | 0 | 0 | 100 | 47 | 55 |
| 191c | 86 | 0 | 100 | 23 | 0 |
| 192a | 0 | 0 | 100 | 0 | 85 |
| 192b | 0 | 0 | 100 | 0 | 0 |
| 193 | 0 | 0 | 100 | 0 | 55 |
| 194 | 0 | 0 | 100 | 0 | 0 |
| 195 | 85 | 0 | 99 | 32 | — |
| 196 | 0 | 0 | 86 | 0 | — |
| 197 | 59 | 0 | 86 | 0 | — |
| 198a | 75 | 28 | 100 | 5 | — |
| 198b | 59 | 28 | 100 | 5 | — |
| 199 | 85 | 68 | 97 | 5 | — |
| 200a | 0 | 0 | 100 | 5 | — |
| 200b | 0 | 0 | 100 | 5 | — |
| 201 | 90 | 0 | 53 | 46 | 0 |
| 202 | 0 | 0 | 53 | 0 | 0 |
| 203 | 0 | 28 | 91 | 0 | 0 |
| 204 | 0 | 0 | 74 | 0 | 0 |
| 205 | 0 | 68 | 74 | 0 | 0 |
| 206 | 0 | 0 | 74 | 0 | 0 |
| 207 | 0 | 0 | 0 | 0 | 0 |
| 208 | 0 | 28 | 94 | 45 | 0 |
| 209 | 0 | 0 | 86 | 0 | 0 |
| 210 | 0 | 0 | 91 | 0 | 0 |
| 211 | 63 | 0 | 100 | 76 | 0 |
| 212 | 0 | 0 | 100 | 23 | 0 |
| 213 | 63 | 0 | 99 | 62 | 0 |
| 214 | 0 | 0 | 100 | 23 | 0 |
| 215a | 63 | 0 | 99 | 45 | 0 |
| 215b | 0 | 28 | 99 | 76 | 83 |
| 216 | 0 | 0 | 99 | 9 | 45 |
| 217 | 0 | 0 | 99 | 0 | 0 |
| 218 | 86 | 68 | 100 | 17 | 0 |
| 219 | 86 | 86 | 99 | 96 | 0 |
| 220 | 0 | 0 | 100 | 85 | 0 |
| 221a | 0 | 0 | 100 | 41 | 0 |
| 221b | 62 | 68 | 100 | 41 | 0 |
| 222 | 62 | 28 | 100 | 41 | 0 |
| 223 | 62 | 28 | 100 | 41 | 0 |
| 224 | 85 | 0 | 100 | 5 | — |
| 225 | 91 | 86 | 100 | 5 | — |
| 226 | 0 | 0 | 100 | 0 | — |
| 227 | 0 | 0 | 100 | 0 | — |
| 228 | 95 | 0 | 52 | 7 | 47 |
| 229a | 0 | 0 | 100 | 0 | 55 |
| 229b | 0 | 0 | 100 | 25 | 95 |
| 230 | 0 | 0 | 53 | 0 | 45 |
| 231 | 0 | 0 | 97 | 0 | 93 |
| 232 | 62 | 0 | 100 | 35 | 69 |
| 233 | 62 | 0 | 94 | 9 | 6 |
| 234 | 0 | 0 | 100 | 0 | 0 |
| 235 | 0 | 0 | 91 | 0 | ND |
| 236 | 77 | 0 | 97 | 0 | 0 |
| 237 | 62 | 0 | 53 | 9 | 0 |
| 238 | 62 | 0 | 74 | 0 | ND |
| 239 | 0 | 0 | 97 | 88 | 0 |
| 240 | 63 | 0 | 94 | 96 | 0 |
| 241 | 38 | 0 | 74 | 74 | 0 |
| 242 | 0 | 0 | 74 | 96 | 0 |
| 243 | 38 | 0 | 74 | 74 | 0 |
| 244 | 86 | 0 | 99 | 74 | 0 |
| 245 | 72 | 0 | 100 | 0 | 0 |
| 246 | 53 | 0 | 97 | 0 | 0 |
| 247 | 53 | 0 | 85 | 0 | 0 |
| 248 | 53 | 0 | 90 | 62 | 83 |
| 249 | 0 | 0 | 94 | 0 | 0 |
| 250 | 0 | 0 | 52 | 0 | 85 |
| 251 | 0 | 0 | 94 | 0 | 0 |
| 252 | 0 | 0 | 99 | 5 | — |
| 253 | 59 | 0 | 100 | 0 | — |
| 254 | 0 | 0 | 53 | 0 | 0 |
| 255 | 28 | 0 | 74 | 0 | 0 |
| 256 | 56 | 0 | 0 | 0 | 0 |
| 257 | 0 | 0 | 0 | 0 | 0 |
| 258 | 74 | 27 | 94 | 0 | 0 |
| 259 | 84 | 0 | 91 | 0 | 48 |

TABLE A-continued

| Cmpd. No | Test A | Test B | Test C | Test D | Test E |
|---|---|---|---|---|---|
| 260 | 0 | 0 | 74 | 24 | 83 |
| 261 | 0 | 0 | 100 | 54 | 0 |
| 262 | 98 | 0 | 53 | 99 | 0 |
| 263 | 86 | 0 | 86 | 33 | 0 |
| 264 | 0 | 0 | 90 | 54 | 94 |
| 265 | 77 | 0 | 91 | 96 | 0 |
| 266 | 63 | 0 | 91 | 74 | 0 |
| 267a | 78 | 0 | 97 | 0 | 55 |
| 267b | 92 | 0 | 100 | 0 | 55 |
| 268 | 38 | 0 | 91 | 88 | 0 |
| 269 | 98 | 0 | 94 | 74 | 0 |
| 270 | 77 | 0 | 91 | 96 | 0 |
| 271 | 77 | 0 | 94 | 96 | 0 |
| 272 | 76 | 0 | 53 | 63 | 0 |
| 273 | 86 | 0 | 53 | 23 | 0 |
| 274 | 61 | 28 | 74 | 23 | 58 |
| 275 | 0 | 0 | 53 | 0 | 99 |
| 276 | 0 | 0 | 0 | 0 | 94 |
| 277 | 0 | 0 | 0 | 0 | 0 |
| 278 | 56 | 67 | 32 | 0 | 94 |
| 279 | 56 | 0 | 0 | 0 | 0 |
| 280 | 56 | 0 | 74 | 0 | 0 |
| 281 | 56 | 0 | 53 | 0 | 0 |
| 282 | 0 | 0 | 100 | 24 | 0 |
| 283 | 0 | 0 | 99 | 0 | 0 |
| 284 | 0 | 0 | 99 | 0 | 0 |
| 285 | 59 | 0 | 97 | 0 | 0 |
| 286 | 76 | 0 | 99 | 0 | 0 |
| 287 | 0 | 0 | 97 | 23 | 0 |
| 288 | 33 | 0 | 86 | 0 | 0 |
| 289 | 0 | 0 | 90 | 45 | 0 |
| 290 | 59 | 0 | 90 | 0 | 0 |
| 291 | 0 | 0 | 90 | 0 | 0 |
| 292 | 0 | 0 | 99 | 46 | 0 |
| 293 | 0 | 0 | 100 | 23 | 0 |
| 294 | 0 | 0 | 99 | 24 | 0 |
| 295 | 0 | 0 | 100 | 0 | 0 |
| 296 | 0 | 0 | 100 | 24 | 0 |
| 297 | 0 | 0 | 100 | 46 | 0 |
| 298 | 62 | 0 | 99 | 99 | 0 |
| 301 | 62 | 0 | 100 | 24 | 0 |
| 302 | 0 | 0 | 99 | 24 | 0 |
| 303 | 0 | 0 | 99 | 100 | 0 |
| 304 | 0 | 0 | 97 | 0 | 0 |
| 305 | 0 | 0 | 53 | 0 | 0 |
| 306 | 0 | 67 | 99 | 0 | 94 |
| 307 | 36 | 0 | 94 | 0 | 0 |
| 308 | 86 | 28 | 100 | 45 | 0 |
| 309 | 86 | 0 | 91 | 23 | 0 |
| 310 | 84 | 25 | 53 | 0 | 18 |
| 311 | 84 | 0 | 0 | 0 | 0 |
| 312 | 0 | 0 | 0 | 82 | 0 |
| 313 | 0 | 0 | 26 | 32 | 47 |
| 314 | 0 | 0 | 72 | 0 | 0 |
| 315 | 60 | 99 | 51 | 16 | 0 |
| 316 | 0 | 0 | 53 | 0 | 0 |
| 317* | 57 | 0 | 85 | 19 | 0 |
| 318* | 90 | 0 | 53 | 0 | 0 |
| 320 | 59 | 68 | 100 | 0 | — |

*Tested at 40 ppm.
**Tested at 100 ppm.

What is claimed is:

1. A compound selected from the formula I

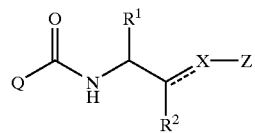

wherein

Q is

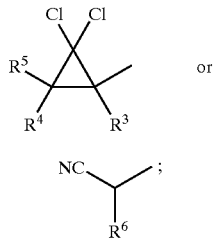

Z is

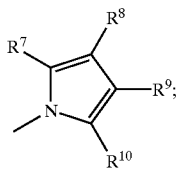

X is —O—, —CH($R^{11}$)— or =C($R^{11}$)—;

$R^1$ is H or $CH_3$;

$R^2$ is H or $CH_3$;

$R^3$ is H, $C_1$–$C_3$ alkyl optionally substituted with halogen or CN;

$R^4$ is H or $C_1$–$C_2$ alkyl; or $R^3$ and $R^4$ can be taken together as —$CH_2CH_2CH_2$— or —$CH_2CH_2CH_2CH_2$—;

$R^5$ is H, $C_1$–$C_2$ alkyl optionally substituted with halogen or CN;

$R^6$ is $C_2$–$C_6$ alkyl, $C_2$–$C_6$ alkenyl, $C_2$–$C_6$ alkynyl or $C_3$–$C_6$ cycloalkyl each optionally substituted with halogen or CN;

$R^7$ is H, CN, halogen, $C_1$–$C_4$ haloalkyl, $C_1$–$C_4$ alkyl, $C_2$–$C_4$ alkenyl or $C_2$–$C_4$ alkynyl each optionally substituted with halogen or CN;

$R^8$, $R^9$ and $R^{10}$ are each independently H, halogen, CN, $C_1$–$C_3$ alkyl, $C_1$–$C_3$ haloalkyl, $SCF_2H$, $SCF_3$ or $Si(CH_3)_3$; and $R^{11}$ is H, $C_1$–$C_5$ alkyl, $C_2$–$C_5$ alkenyl or $C_2$–$C_5$ alkynyl.

2. A compound of claim 1 wherein:

Q is Q-1;

$R^1$ is $CH_3$;

$R^2$ is H;

$R^3$ is $CH_2CH_3$; and $R^4$ is $CH_3$.

3. A compound of claim 2 wherein $R^7$ is H, halogen, CN, $C_1$–$C_4$ alkyl or $C_2$–$C_4$ alkenyl;

$R^8$ is fixed in the 4 position and is H or F; and $R^9$ is fixed in the 5 position.

4. A compound of claim 1 wherein

Q is Q-2;

$R^1$ is $CH_3$;

$R^2$ is H or phenyl optionally substituted with halogen, cyano, $C_1$–$C_2$ alkyl or $C_1$–$C_2$ alkoxy; and $R^6$ is $C_2$–$C_6$ alkyl or $C_2$–$C_6$ alkenyl each optionally substituted with halogen.

5. A compound of claim 4 wherein
R$^7$ is H, halogen, CN, C$_1$–C$_4$ alkyl or C$_2$–C$_4$ alkenyl;
R$^8$ is fixed in the 4 position and is H or F; and
R$^9$ is fixed in the 5 position.

6. A fungicidal composition comprising a fungicidally effective amount of a compound of claim 1 and at least one of a surfactant, a solid diluent or a liquid diluent.

7. A method for controlling plant diseases caused by fungal plant pathogens comprising applying to the plant or portion thereof, or to the plant seed or seedling, a fungicidally effective amount of a compound of claim 1.

8. A fungicidal composition comprising the compound of claim 1.

9. The composition of claim 8 wherein the composition is in a form selected from the group consisting of liquid, powder, emollient, aerosol, and granules.

10. A method of treating a plant for a fungal pathogen wherein the method comprises
   a. contacting at least a portion of a plant with an effective amount of the composition of claim 9.

* * * * *